US012390521B2

(12) United States Patent
Reeder et al.

(10) Patent No.: US 12,390,521 B2
(45) Date of Patent: Aug. 19, 2025

(54) CANINE DISTEMPER VACCINES AND METHODS OF TREATMENT USING THE SAME

(71) Applicant: THE WISTAR INSTITUTE OF ANATOMY AND BIOLOGY, Philadelphia, PA (US)

(72) Inventors: Sophia Reeder, Philadelphia, PA (US); Emma Reuschel, Philadelphia, PA (US); David Weiner, Merion, PA (US)

(73) Assignee: The Wistar Institute of Anatomy and Biology, Philadelphia, PA (US)

( * ) Notice: Subject to any disclaimer, the term of this patent is extended or adjusted under 35 U.S.C. 154(b) by 789 days.

(21) Appl. No.: 17/287,698

(22) PCT Filed: Oct. 25, 2019

(86) PCT No.: PCT/US2019/058023

§ 371 (c)(1),
(2) Date: Apr. 22, 2021

(87) PCT Pub. No.: WO2020/086939

PCT Pub. Date: Apr. 30, 2020

(65) Prior Publication Data

US 2021/0401970 A1 Dec. 30, 2021

Related U.S. Application Data

(60) Provisional application No. 62/751,002, filed on Oct. 26, 2018.

(51) Int. Cl.

| | |
|---|---|
| ***A61K 39/175*** | (2006.01) |
| ***A61K 39/00*** | (2006.01) |
| ***A61K 48/00*** | (2006.01) |
| ***A61P 31/14*** | (2006.01) |

(52) U.S. Cl.

CPC ........ *A61K 39/175* (2013.01); *A61K 48/0066* (2013.01); *A61P 31/14* (2018.01); *A61K 2039/525* (2013.01)

(58) Field of Classification Search

CPC .............. A61K 39/175; A61K 48/0066; A61K 2039/525; A61K 2039/53; A61K 2039/545; A61K 2039/552; A61K 2039/572; A61K 2039/575; A61K 39/12; A61P 31/14; C12N 2760/18434

See application file for complete search history.

(56) References Cited

U.S. PATENT DOCUMENTS

| | | | | |
|---|---|---|---|---|
| 5,756,102 | A * | 5/1998 | Paoletti | A61P 31/12 435/235.1 |
| 6,309,647 | B1 | 10/2001 | Paoletti | |
| 9,139,620 | B2 | 9/2015 | Yuen | |
| 2016/0199483 | A1 | 7/2016 | Audonnet | |
| 2024/0066081 | A1 * | 2/2024 | Russell | C12N 7/00 |

FOREIGN PATENT DOCUMENTS

| | | |
|---|---|---|
| WO | 2017087550 | 5/2017 |
| WO | 2018212842 | 11/2018 |
| WO | WO-2023111728 A1 * | 6/2023 |

OTHER PUBLICATIONS

Gustafsson C, Govindarajan S, Minshull J. Codon bias and heterologous protein expression. Trends Biotechnol. Jul. 2004;22(7):346-53. (Year: 2004).*

* cited by examiner

*Primary Examiner* — Rachel B Gill

(74) *Attorney, Agent, or Firm* — Riverside Law LLP

(57) ABSTRACT

The present invention relates to compositions and methods for treating and/or preventing Canine Distemper Virus (CDV) in mammals susceptible to CDV.

20 Claims, 7 Drawing Sheets

Specification includes a Sequence Listing.

SEQUENCE LISTING

```
<160> NUMBER OF SEQ ID NOS: 21

<210> SEQ ID NO 1
<211> LENGTH: 1818
<212> TYPE: DNA
<213> ORGANISM: Artificial Sequence
<220> FEATURE:
<223> OTHER INFORMATION: Consensus H antigen

<400> SEQUENCE: 1

ctcagctacc aggacaaggt cggagccttc tacaaggaca acgccagggc caacagctcc     60

aagctgagcc tcgtgacgga ggaacaggga ggaagaaggc cccccctacct gctcttcgtc    120

ctgctcatcc tgctcgtggg aatcctggcc ctgctcgcca tcacgggcgt ccggttccac    180

caggtgagca catccaacat ggagttcagc aggctgctca aggaggacat ggaaaagtcc    240

gaggccgtgc accaccaggt catcgacgtc ctcacgcccc tgttcaagat catcggagac    300

gaaatcggcc tgcgcctccc ccagaagctg aacgagatca agcagttcat cctccagaag    360

accaacttct tcaaccccaa ccgggagttc gacttcaggg acctgcactg gtgcatcaac    420

ccccccctcca agatcaaggt caacttcacg aactactgtg acacaatcgg cgtgcggaag    480

agcatcgcct ccgccgccaa ccccatcctg ctcagcgccc tgtccggagg aagaggcgac    540

atcttccccc cctacaggtg cagcggagcc accacgtccg tgggaagagt cttccccctc    600

agcgtgtccc tgagcatgtc cctcatcagc agaacatccg agatcatcaa catgctgacc    660

gccatcagcg acggagtcta cggcaagaca tacctgctcg tgcccgacta catcgaggga    720

gaattcgaca cccagaagat ccgcgtgttc gaaatcggct tcatcaagag atggctcaac    780

gacatgcccc tgctccagac aaccaactac atggtgctgc ccgagaactc caaggccaag    840

gtctgcacca tcgccgtggg agaactgacg ctcgccagcc tgtgtgtcga cgagtccacg    900

gtgctgctct accacgacag caacggcagc caggacggca tcctggtggt cacactcgga    960

atcttcggag ccacccccat ggaccaggtg gaggaagtca tccccgtggc ccaccccagc   1020

gtggagaaga tccacatcac caaccaccgg ggcttcatca aggacagcat cgccacgtgg   1080

atggtccccg ccctggtgtc cgaaaagcag gaggaacaga agaactgcct ggagagcgcc   1140

tgtcagcgca agtcctaccc catgtgcaac cagaccagct gggaaccctt cggaggagga   1200

cagctgccct cctacggaag actgacgctc cccctggacc ccagcatcga cctccagctg   1260

aacatctcct tcacatacgg ccccgtgatc ctcaacggag acggcatgga ctactacgag   1320

agccccctgc tcgactccgg atggctgacg atccccccca agaacggaac agtgctcggc   1380

ctgatcaaca aggccagccg gggagaccag ttcaccgtca tcccccacgt gctgacgttc   1440

gcccccaggg aaagctccgg caactgttac ctccccatcc agacgagcca gatcatggac   1500

aaggacgtgc tgaccgagtc caacctcgtg gtcctgccca cgcagaactt ccgctacgtg   1560

atcgccacat acgacatcag cagaggcgac cacgccatcg tctactacgt gtacgacccc   1620
```

-continued

```
atccggacaa tctcctacac ctaccccttc aggctgacga caaagggccg ccccgacttc   1680

ctcagaatcg agtgcttcgt gtgggacgac gacctctggt gtcaccagtt ctaccggttc   1740

gaagccgaca tcaccaacag caccacgtcc gtcgagaacc tggtgcgcat cagattcagc   1800

tgtaacaggt ccaagccc                                                 1818


<210> SEQ ID NO 2
<211> LENGTH: 606
<212> TYPE: PRT
<213> ORGANISM: Artificial Sequence
<220> FEATURE:
<223> OTHER INFORMATION: Consensus H antigen

<400> SEQUENCE: 2

Leu Ser Tyr Gln Asp Lys Val Gly Ala Phe Tyr Lys Asp Asn Ala Arg
1               5                   10                  15

Ala Asn Ser Ser Lys Leu Ser Leu Val Thr Glu Glu Gln Gly Gly Arg
            20                  25                  30

Arg Pro Pro Tyr Leu Leu Phe Val Leu Leu Ile Leu Leu Val Gly Ile
        35                  40                  45

Leu Ala Leu Leu Ala Ile Thr Gly Val Arg Phe His Gln Val Ser Thr
    50                  55                  60

Ser Asn Met Glu Phe Ser Arg Leu Leu Lys Glu Asp Met Glu Lys Ser
65                  70                  75                  80

Glu Ala Val His His Gln Val Ile Asp Val Leu Thr Pro Leu Phe Lys
                85                  90                  95

Ile Ile Gly Asp Glu Ile Gly Leu Arg Leu Pro Gln Lys Leu Asn Glu
            100                 105                 110

Ile Lys Gln Phe Ile Leu Gln Lys Thr Asn Phe Phe Asn Pro Asn Arg
        115                 120                 125

Glu Phe Asp Phe Arg Asp Leu His Trp Cys Ile Asn Pro Pro Ser Lys
    130                 135                 140

Ile Lys Val Asn Phe Thr Asn Tyr Cys Asp Thr Ile Gly Val Arg Lys
145                 150                 155                 160

Ser Ile Ala Ser Ala Ala Asn Pro Ile Leu Leu Ser Ala Leu Ser Gly
                165                 170                 175

Gly Arg Gly Asp Ile Phe Pro Pro Tyr Arg Cys Ser Gly Ala Thr Thr
            180                 185                 190

Ser Val Gly Arg Val Phe Pro Leu Ser Val Ser Leu Ser Met Ser Leu
        195                 200                 205

Ile Ser Arg Thr Ser Glu Ile Ile Asn Met Leu Thr Ala Ile Ser Asp
    210                 215                 220

Gly Val Tyr Gly Lys Thr Tyr Leu Leu Val Pro Asp Tyr Ile Glu Gly
225                 230                 235                 240

Glu Phe Asp Thr Gln Lys Ile Arg Val Phe Glu Ile Gly Phe Ile Lys
                245                 250                 255

Arg Trp Leu Asn Asp Met Pro Leu Leu Gln Thr Thr Asn Tyr Met Val
            260                 265                 270

Leu Pro Glu Asn Ser Lys Ala Lys Val Cys Thr Ile Ala Val Gly Glu
        275                 280                 285

Leu Thr Leu Ala Ser Leu Cys Val Asp Glu Ser Thr Val Leu Leu Tyr
    290                 295                 300

His Asp Ser Asn Gly Ser Gln Asp Gly Ile Leu Val Val Thr Leu Gly
305                 310                 315                 320

Ile Phe Gly Ala Thr Pro Met Asp Gln Val Glu Glu Val Ile Pro Val
```

```
                325                 330                 335

Ala His Pro Ser Val Glu Lys Ile His Ile Thr Asn His Arg Gly Phe
            340                 345                 350

Ile Lys Asp Ser Ile Ala Thr Trp Met Val Pro Ala Leu Val Ser Glu
        355                 360                 365

Lys Gln Glu Glu Gln Lys Asn Cys Leu Glu Ser Ala Cys Gln Arg Lys
    370                 375                 380

Ser Tyr Pro Met Cys Asn Gln Thr Ser Trp Glu Pro Phe Gly Gly Gly
385                 390                 395                 400

Gln Leu Pro Ser Tyr Gly Arg Leu Thr Leu Pro Leu Asp Pro Ser Ile
                405                 410                 415

Asp Leu Gln Leu Asn Ile Ser Phe Thr Tyr Gly Pro Val Ile Leu Asn
            420                 425                 430

Gly Asp Gly Met Asp Tyr Tyr Glu Ser Pro Leu Leu Asp Ser Gly Trp
        435                 440                 445

Leu Thr Ile Pro Pro Lys Asn Gly Thr Val Leu Gly Leu Ile Asn Lys
    450                 455                 460

Ala Ser Arg Gly Asp Gln Phe Thr Val Ile Pro His Val Leu Thr Phe
465                 470                 475                 480

Ala Pro Arg Glu Ser Ser Gly Asn Cys Tyr Leu Pro Ile Gln Thr Ser
                485                 490                 495

Gln Ile Met Asp Lys Asp Val Leu Thr Glu Ser Asn Leu Val Val Leu
            500                 505                 510

Pro Thr Gln Asn Phe Arg Tyr Val Ile Ala Thr Tyr Asp Ile Ser Arg
        515                 520                 525

Gly Asp His Ala Ile Val Tyr Tyr Val Tyr Asp Pro Ile Arg Thr Ile
    530                 535                 540

Ser Tyr Thr Tyr Pro Phe Arg Leu Thr Thr Lys Gly Arg Pro Asp Phe
545                 550                 555                 560

Leu Arg Ile Glu Cys Phe Val Trp Asp Asp Leu Trp Cys His Gln
                565                 570                 575

Phe Tyr Arg Phe Glu Ala Asp Ile Thr Asn Ser Thr Thr Ser Val Glu
            580                 585                 590

Asn Leu Val Arg Ile Arg Phe Ser Cys Asn Arg Ser Lys Pro
        595                 600                 605


<210> SEQ ID NO 3
<211> LENGTH: 1878
<212> TYPE: DNA
<213> ORGANISM: Artificial Sequence
<220> FEATURE:
<223> OTHER INFORMATION: Consensus H antigen operably linked to an IgE
      leader sequence

<400> SEQUENCE: 3

atggactgga catggatcct cttcctcgtc gccgccgcca cacgggtgca cagcctcagc      60

taccaggaca aggtcggagc cttctacaag gacaacgcca gggccaacag ctccaagctg     120

agcctcgtga cggaggaaca gggaggaaga aggcccccct acctgctctt cgtcctgctc     180

atcctgctcg tgggaatcct ggccctgctc gccatcacgg gcgtccggtt ccaccaggtg     240

agcacatcca acatggagtt cagcaggctg ctcaaggagg acatggaaaa gtccgaggcc     300

gtgcaccacc aggtcatcga cgtcctcacg cccctgttca agatcatcgg agacgaaatc     360

ggcctgcgcc tcccccagaa gctgaacgag atcaagcagt tcatcctcca gaagaccaac     420

ttcttcaacc ccaaccggga gttcgacttc agggacctgc actggtgcat caacccccc      480
```

```
tccaagatca aggtcaactt cacgaactac tgtgacacaa tcggcgtgcg gaagagcatc    540

gcctccgccg ccaaccccat cctgctcagc gccctgtccg gaggaagagg cgacatcttc    600

ccccccctaca ggtgcagcgg agccaccacg tccgtgggaa gagtcttccc cctcagcgtg    660

tccctgagca tgtccctcat cagcagaaca tccgagatca tcaacatgct gaccgccatc    720

agcgacggag tctacggcaa gacatacctg ctcgtgcccg actacatcga gggagaattc    780

gacacccaga agatccgcgt gttcgaaatc ggcttcatca agagatggct caacgacatg    840

cccctgctcc agacaaccaa ctacatggtg ctgcccgaga actccaaggc caaggtctgc    900

accatcgccg tgggagaact gacgctcgcc agcctgtgtg tcgacgagtc cacggtgctg    960

ctctaccacg acagcaacgg cagccaggac ggcatcctgg tggtcacact cggaatcttc   1020

ggagccaccc ccatggacca ggtggaggaa gtcatccccg tggcccaccc cagcgtggag   1080

aagatccaca tcaccaacca ccggggcttc atcaaggaca gcatcgccac gtggatggtc   1140

cccgccctgg tgtccgaaaa gcaggaggaa cagaagaact gcctggagag cgcctgtcag   1200

cgcaagtcct accccatgtg caaccagacc agctgggaac ccttcggagg aggacagctg   1260

ccctcctacg gaagactgac gctcccccctg gaccccagca tcgacctcca gctgaacatc   1320

tccttcacat acggccccgt gatcctcaac ggagacggca tggactacta cgagagcccc   1380

ctgctcgact ccggatggct gacgatcccc cccaagaacg gaacagtgct cggcctgatc   1440

aacaaggcca gccggggaga ccagttcacc gtcatccccc acgtgctgac gttcgccccc   1500

agggaaagct ccggcaactg ttacctcccc atccagacga gccagatcat ggacaaggac   1560

gtgctgaccg agtccaacct cgtggtcctg cccacgcaga acttccgcta cgtgatcgcc   1620

acatacgaca tcagcagagg cgaccacgcc atcgtctact acgtgtacga ccccatccgg   1680

acaatctcct acacctaccc cttcaggctg acgacaaagg gccgccccga cttcctcaga   1740

atcgagtgct tcgtgtggga cgacgacctc tggtgtcacc agttctaccg gttcgaagcc   1800

gacatcacca acagcaccac gtccgtcgag aacctggtgc gcatcagatt cagctgtaac   1860

aggtccaagc cctgataa                                                1878
```

<210> SEQ ID NO 4
<211> LENGTH: 624
<212> TYPE: PRT
<213> ORGANISM: Artificial Sequence
<220> FEATURE:
<223> OTHER INFORMATION: Consensus H antigen operably linked to an IgE leader sequence

<400> SEQUENCE: 4

```
Met Asp Trp Thr Trp Ile Leu Phe Leu Val Ala Ala Ala Thr Arg Val
1               5                   10                  15

His Ser Leu Ser Tyr Gln Asp Lys Val Gly Ala Phe Tyr Lys Asp Asn
            20                  25                  30

Ala Arg Ala Asn Ser Ser Lys Leu Ser Leu Val Thr Glu Glu Gln Gly
        35                  40                  45

Gly Arg Arg Pro Pro Tyr Leu Leu Phe Val Leu Leu Ile Leu Leu Val
    50                  55                  60

Gly Ile Leu Ala Leu Leu Ala Ile Thr Gly Val Arg Phe His Gln Val
65                  70                  75                  80

Ser Thr Ser Asn Met Glu Phe Ser Arg Leu Leu Lys Glu Asp Met Glu
                85                  90                  95

Lys Ser Glu Ala Val His His Gln Val Ile Asp Val Leu Thr Pro Leu
```

-continued

```
            100                 105                 110

Phe Lys Ile Ile Gly Asp Glu Ile Gly Leu Arg Leu Pro Gln Lys Leu
        115                 120                 125

Asn Glu Ile Lys Gln Phe Ile Leu Gln Lys Thr Asn Phe Phe Asn Pro
    130                 135                 140

Asn Arg Glu Phe Asp Phe Arg Asp Leu His Trp Cys Ile Asn Pro Pro
145                 150                 155                 160

Ser Lys Ile Lys Val Asn Phe Thr Asn Tyr Cys Asp Thr Ile Gly Val
                165                 170                 175

Arg Lys Ser Ile Ala Ser Ala Ala Asn Pro Ile Leu Leu Ser Ala Leu
            180                 185                 190

Ser Gly Gly Arg Gly Asp Ile Phe Pro Pro Tyr Arg Cys Ser Gly Ala
        195                 200                 205

Thr Thr Ser Val Gly Arg Val Phe Pro Leu Ser Val Ser Leu Ser Met
    210                 215                 220

Ser Leu Ile Ser Arg Thr Ser Glu Ile Ile Asn Met Leu Thr Ala Ile
225                 230                 235                 240

Ser Asp Gly Val Tyr Gly Lys Thr Tyr Leu Leu Val Pro Asp Tyr Ile
                245                 250                 255

Glu Gly Glu Phe Asp Thr Gln Lys Ile Arg Val Phe Glu Ile Gly Phe
            260                 265                 270

Ile Lys Arg Trp Leu Asn Asp Met Pro Leu Leu Gln Thr Thr Asn Tyr
        275                 280                 285

Met Val Leu Pro Glu Asn Ser Lys Ala Lys Val Cys Thr Ile Ala Val
    290                 295                 300

Gly Glu Leu Thr Leu Ala Ser Leu Cys Val Asp Glu Ser Thr Val Leu
305                 310                 315                 320

Leu Tyr His Asp Ser Asn Gly Ser Gln Asp Gly Ile Leu Val Val Thr
                325                 330                 335

Leu Gly Ile Phe Gly Ala Thr Pro Met Asp Gln Val Glu Glu Val Ile
            340                 345                 350

Pro Val Ala His Pro Ser Val Glu Lys Ile His Ile Thr Asn His Arg
        355                 360                 365

Gly Phe Ile Lys Asp Ser Ile Ala Thr Trp Met Val Pro Ala Leu Val
    370                 375                 380

Ser Glu Lys Gln Glu Glu Gln Lys Asn Cys Leu Glu Ser Ala Cys Gln
385                 390                 395                 400

Arg Lys Ser Tyr Pro Met Cys Asn Gln Thr Ser Trp Glu Pro Phe Gly
                405                 410                 415

Gly Gly Gln Leu Pro Ser Tyr Gly Arg Leu Thr Leu Pro Leu Asp Pro
            420                 425                 430

Ser Ile Asp Leu Gln Leu Asn Ile Ser Phe Thr Tyr Gly Pro Val Ile
        435                 440                 445

Leu Asn Gly Asp Gly Met Asp Tyr Tyr Glu Ser Pro Leu Leu Asp Ser
    450                 455                 460

Gly Trp Leu Thr Ile Pro Pro Lys Asn Gly Thr Val Leu Gly Leu Ile
465                 470                 475                 480

Asn Lys Ala Ser Arg Gly Asp Gln Phe Thr Val Ile Pro His Val Leu
                485                 490                 495

Thr Phe Ala Pro Arg Glu Ser Ser Gly Asn Cys Tyr Leu Pro Ile Gln
            500                 505                 510

Thr Ser Gln Ile Met Asp Lys Asp Val Leu Thr Glu Ser Asn Leu Val
        515                 520                 525
```

```
Val Leu Pro Thr Gln Asn Phe Arg Tyr Val Ile Ala Thr Tyr Asp Ile
    530                 535                 540

Ser Arg Gly Asp His Ala Ile Val Tyr Tyr Val Tyr Asp Pro Ile Arg
545                 550                 555                 560

Thr Ile Ser Tyr Thr Tyr Pro Phe Arg Leu Thr Thr Lys Gly Arg Pro
                565                 570                 575

Asp Phe Leu Arg Ile Glu Cys Phe Val Trp Asp Asp Asp Leu Trp Cys
            580                 585                 590

His Gln Phe Tyr Arg Phe Glu Ala Asp Ile Thr Asn Ser Thr Thr Ser
        595                 600                 605

Val Glu Asn Leu Val Arg Ile Arg Phe Ser Cys Asn Arg Ser Lys Pro
    610                 615                 620
```

```
<210> SEQ ID NO 5
<211> LENGTH: 1869
<212> TYPE: DNA
<213> ORGANISM: Artificial Sequence
<220> FEATURE:
<223> OTHER INFORMATION: Optimized H IgE leader sequence

<400> SEQUENCE: 5

atggactgga catggattct gtttttggtc gccgccgcca caagagtgca tagcctccct     60

tatcaagaca aggtcggggc attctacaag gacaacgcca gagccaattc cactaaactg    120

agcctcgtga ccgaaggcca cggcggaaga aggccaccct acctgctctt cgtgctgctc    180

atcctgctcg tggggattct ggccctgctc gccatcacag gcgtgagatt ccatcaggtg    240

tccactagca acatggagtt ttctaggctg ctcaaggagg atatggaaaa atcagaggcc    300

gtgcaccatc aagtgatcga cgtgctcact cccctgttca agatcattgg cgatgaaatt    360

ggactgaggc tccctcaaaa gctgaacgag atcaaacagt ttattctcca aaagacaaat    420

ttctttaacc caaacagaga attcgacttt agggatctgc actggtgcat caaccctcca    480

tccacagtga aggtgaactt cactaattat tgtgagtcta tcggcattag aaaagccatc    540

gcctcagccg ccaatccaat tctgctctcc gccctgagcg ggggcagagg agacatcttc    600

ccaccacaca ggtgctctgg cgccaccaca tcagtgggaa aggtgtttcc tctctccgtg    660

tccctgtcca tgagcctcat ttctaggact tcagaagtga tcaacatgct gaccgccatt    720

tccgatggag tgtacgggaa aacatatctg ctcgtgccag acgatatcga gagagaattt    780

gacactagag aaattagggt gttcgagatc gggtttatta agaggtggct gaatgatatg    840

cctctgctcc agactaccaa ctacatggtg ctcccaaaaa atagcaaggc caaagtgtgc    900

accatcgccg tgggagagct gacactcgcc tctctgtgcg tggaggaatc aaccgtgctg    960

ctctatcacg actccagcgg gtcccaagat ggcatcctgg tggtgactct cgggattttc   1020

tgggccaccc ccatggacca catcgaggaa gtgattcctg tggcccatcc aagcatgaag   1080

aaaatccaca ttactaacca tagagggttt atcaaggatt ccattgcaac ctggatggtg   1140

cccgccctgg caagcgaaaa gcaggaggaa caaaaaggct gcctggagtc tgcctgtcag   1200

aggaaaacat accctatgtg caatcaagcc tcttgggaac ccttcggagg gagacagctg   1260

ccttcatatg gaaggctgac cctcccactg gacgcatccg tggatctcca actgaacatc   1320

agctttacat acggaccagt gattctcaat ggcgacggaa tggattacta tgagtcccca   1380

ctgctgaaca gcgggtggct gacaatccca cccaaggacg gaactatctc tgggctgatc   1440

aacaaggccg ggagaggcga tcagttcacc gtgctgccac acgtgctcac atttgccccc   1500
```

```
agggaatctt caggcaactg ttatctgcct atccagacct cacaaattag agacagggat   1560

gtgctgatcg agtccaatat tgtggtgctc ccaacccaaa gcatcagata cgtgattgcc   1620

acatatgaca tctctaggtc agaccacgcc atcgtgtact acgtgtacga ccctatcaga   1680

accattagct atacacatcc attcagactg acaactaagg gaagacccga tttcctcagg   1740

atcgaatgct tcgtgtggga cgataacctg tggtgtcatc agttctacag atttgaggcc   1800

gacatcgcaa atagcacaac ctccgtggaa aacttggtca ggattagatt ctcatgtaac   1860

agatgataa                                                           1869


<210> SEQ ID NO 6
<211> LENGTH: 621
<212> TYPE: PRT
<213> ORGANISM: Artificial Sequence
<220> FEATURE:
<223> OTHER INFORMATION: Optimized H IgE leader sequence

<400> SEQUENCE: 6

Met Asp Trp Thr Trp Ile Leu Phe Leu Val Ala Ala Ala Thr Arg Val
1               5                   10                  15

His Ser Leu Pro Tyr Gln Asp Lys Val Gly Ala Phe Tyr Lys Asp Asn
            20                  25                  30

Ala Arg Ala Asn Ser Thr Lys Leu Ser Leu Val Thr Glu Gly His Gly
        35                  40                  45

Gly Arg Arg Pro Pro Tyr Leu Leu Phe Val Leu Leu Ile Leu Leu Val
    50                  55                  60

Gly Ile Leu Ala Leu Leu Ala Ile Thr Gly Val Arg Phe His Gln Val
65                  70                  75                  80

Ser Thr Ser Asn Met Glu Phe Ser Arg Leu Leu Lys Glu Asp Met Glu
                85                  90                  95

Lys Ser Glu Ala Val His His Gln Val Ile Asp Val Leu Thr Pro Leu
            100                 105                 110

Phe Lys Ile Ile Gly Asp Glu Ile Gly Leu Arg Leu Pro Gln Lys Leu
        115                 120                 125

Asn Glu Ile Lys Gln Phe Ile Leu Gln Lys Thr Asn Phe Phe Asn Pro
    130                 135                 140

Asn Arg Glu Phe Asp Phe Arg Asp Leu His Trp Cys Ile Asn Pro Pro
145                 150                 155                 160

Ser Thr Val Lys Val Asn Phe Thr Asn Tyr Cys Glu Ser Ile Gly Ile
                165                 170                 175

Arg Lys Ala Ile Ala Ser Ala Ala Asn Pro Ile Leu Leu Ser Ala Leu
            180                 185                 190

Ser Gly Gly Arg Gly Asp Ile Phe Pro Pro His Arg Cys Ser Gly Ala
        195                 200                 205

Thr Thr Ser Val Gly Lys Val Phe Pro Leu Ser Val Ser Leu Ser Met
    210                 215                 220

Ser Leu Ile Ser Arg Thr Ser Glu Val Ile Asn Met Leu Thr Ala Ile
225                 230                 235                 240

Ser Asp Gly Val Tyr Gly Lys Thr Tyr Leu Leu Val Pro Asp Asp Ile
                245                 250                 255

Glu Arg Glu Phe Asp Thr Arg Glu Ile Arg Val Phe Glu Ile Gly Phe
            260                 265                 270

Ile Lys Arg Trp Leu Asn Asp Met Pro Leu Leu Gln Thr Thr Asn Tyr
        275                 280                 285

Met Val Leu Pro Lys Asn Ser Lys Ala Lys Val Cys Thr Ile Ala Val
```

```
    290                 295                 300

Gly Glu Leu Thr Leu Ala Ser Leu Cys Val Glu Glu Ser Thr Val Leu
305                 310                 315                 320

Leu Tyr His Asp Ser Ser Gly Ser Gln Asp Gly Ile Leu Val Val Thr
                325                 330                 335

Leu Gly Ile Phe Trp Ala Thr Pro Met Asp His Ile Glu Glu Val Ile
            340                 345                 350

Pro Val Ala His Pro Ser Met Lys Lys Ile His Ile Thr Asn His Arg
        355                 360                 365

Gly Phe Ile Lys Asp Ser Ile Ala Thr Trp Met Val Pro Ala Leu Ala
    370                 375                 380

Ser Glu Lys Gln Glu Glu Gln Lys Gly Cys Leu Glu Ser Ala Cys Gln
385                 390                 395                 400

Arg Lys Thr Tyr Pro Met Cys Asn Gln Ala Ser Trp Glu Pro Phe Gly
                405                 410                 415

Gly Arg Gln Leu Pro Ser Tyr Gly Arg Leu Thr Leu Pro Leu Asp Ala
            420                 425                 430

Ser Val Asp Leu Gln Leu Asn Ile Ser Phe Thr Tyr Gly Pro Val Ile
        435                 440                 445

Leu Asn Gly Asp Gly Met Asp Tyr Tyr Glu Ser Pro Leu Leu Asn Ser
    450                 455                 460

Gly Trp Leu Thr Ile Pro Pro Lys Asp Gly Thr Ile Ser Gly Leu Ile
465                 470                 475                 480

Asn Lys Ala Gly Arg Gly Asp Gln Phe Thr Val Leu Pro His Val Leu
                485                 490                 495

Thr Phe Ala Pro Arg Glu Ser Ser Gly Asn Cys Tyr Leu Pro Ile Gln
            500                 505                 510

Thr Ser Gln Ile Arg Asp Arg Asp Val Leu Ile Glu Ser Asn Ile Val
        515                 520                 525

Val Leu Pro Thr Gln Ser Ile Arg Tyr Val Ile Ala Thr Tyr Asp Ile
    530                 535                 540

Ser Arg Ser Asp His Ala Ile Val Tyr Tyr Val Tyr Asp Pro Ile Arg
545                 550                 555                 560

Thr Ile Ser Tyr Thr His Pro Phe Arg Leu Thr Thr Lys Gly Arg Pro
                565                 570                 575

Asp Phe Leu Arg Ile Glu Cys Phe Val Trp Asp Asp Asn Leu Trp Cys
            580                 585                 590

His Gln Phe Tyr Arg Phe Glu Ala Asp Ile Ala Asn Ser Thr Thr Ser
        595                 600                 605

Val Glu Asn Leu Val Arg Ile Arg Phe Ser Cys Asn Arg
    610                 615                 620
```

<210> SEQ ID NO 7
<211> LENGTH: 1566
<212> TYPE: DNA
<213> ORGANISM: Artificial Sequence
<220> FEATURE:
<223> OTHER INFORMATION: Consensus N antigen, no leader sequence

<400> SEQUENCE: 7

```
gcctctctgc tcaagtcact gacactcttt aaaagaacta gggatcagcc acccctggca     60

tccgggagcg gcggagccat tagaggcatc aagcacgtga tcattgtgct cattccagga    120

gactccagca tcgtgaccag atccaggctg ctcgatagac tggtgaggct cgtgggggac    180

cctgagatca acggaccaaa gctgacaggc atcctgattt ccatcctgag cctctttgtg    240
```

```
gaatccccag ggcagctgat ccaaagaatc attgacgatc ccgacgtgtc catcaagctc    300
gtggaagtga tcccttctat caattcagtg tgcggactga ccttcgcctc cagaggcgcc    360
tccctcgata gcgaggcaga cgaattcttt aagatcgtgg acgagggatc aaaagcccag    420
gggcaactgg gctggctcga aaacaaggat attgtggaca tcgaggtgga cgatgccgaa    480
cagttcaata ttctgctcgc ctccatcctg gcccaaattt ggattctgct cgccaaagca    540
gtgactgcac cagataccgc agcagacagc gagatgagaa ggtggatcaa gtacactcag    600
caaagaaggg tggtgggcga gttcagaatg aacaaaattt ggctggatat cgtgagaaat    660
aggatcgccg aagacctgtc tctcagaagg ttcatggtgg ccctgattct cgatatcaag    720
agatcacccg gaaacaaacc taggatcgcc gagatgattt gtgatatcga caattacatt    780
gtggaagccg ggctggcctc ttttattctc actatcaagt tcggcatcga gaccatgtat    840
cccgccctgg gcctccatga gttttccgga gaactgacca caattgaaag cctgatgatg    900
ctctaccagc aaatgggcga gaccgcccca tatatggtca tcctggagaa ctccgtgcag    960
aacaagttct ccgccggatc atacccccctg ctctggagct atgccatggg cgtgggagtg   1020
gagctggaaa actctatggg cggcctgaac ttcggcagat catactttga tcctgcctat   1080
ttcaggctgg gccaggagat ggtgagaagg agcgccggaa aggtgtcttc agccctggcc   1140
gccgaactcg gaatcactaa ggaggaagcc caactggtgt ccgagattgc cagcaaaact   1200
accgaagaca gaaccatcag gacagccggg cctaaacagt ctcaaattac ctttctgcac   1260
tccgagagaa gcgaagtgac caaccagcaa cctccaacaa tcaacaagag gtcagaaaac   1320
cagggagggg ataaataccc aattcacttc aacgacgaaa gattcccagg gtatacaccc   1380
gatgtgaatt ccagcgagtg gtctgaatca agatacgaca cacagactat ccaagacgat   1440
ggcaatgacg atgacagaaa aagcatggag gccattgcca agatgaggat gctgacaaaa   1500
atgctctctc aacccggaac ttcagaggaa tcttcaccag tgtacaacga cagagaactg   1560
ctcaat                                                               1566
```

<210> SEQ ID NO 8
<211> LENGTH: 522
<212> TYPE: PRT
<213> ORGANISM: Artificial Sequence
<220> FEATURE:
<223> OTHER INFORMATION: Consensus N antigen, no leader sequence

<400> SEQUENCE: 8

```
Ala Ser Leu Leu Lys Ser Leu Thr Leu Phe Lys Arg Thr Arg Asp Gln
1               5                   10                  15

Pro Pro Leu Ala Ser Gly Ser Gly Gly Ala Ile Arg Gly Ile Lys His
            20                  25                  30

Val Ile Ile Val Leu Ile Pro Gly Asp Ser Ser Ile Val Thr Arg Ser
        35                  40                  45

Arg Leu Leu Asp Arg Leu Val Arg Leu Val Gly Asp Pro Glu Ile Asn
    50                  55                  60

Gly Pro Lys Leu Thr Gly Ile Leu Ile Ser Ile Leu Ser Leu Phe Val
65                  70                  75                  80

Glu Ser Pro Gly Gln Leu Ile Gln Arg Ile Ile Asp Asp Pro Asp Val
                85                  90                  95

Ser Ile Lys Leu Val Glu Val Ile Pro Ser Ile Asn Ser Val Cys Gly
            100                 105                 110

Leu Thr Phe Ala Ser Arg Gly Ala Ser Leu Asp Ser Glu Ala Asp Glu
```

```
        115                 120                 125

Phe Phe Lys Ile Val Asp Glu Gly Ser Lys Ala Gln Gly Gln Leu Gly
    130                 135                 140

Trp Leu Glu Asn Lys Asp Ile Val Asp Ile Glu Val Asp Asp Ala Glu
145                 150                 155                 160

Gln Phe Asn Ile Leu Leu Ala Ser Ile Leu Ala Gln Ile Trp Ile Leu
                165                 170                 175

Leu Ala Lys Ala Val Thr Ala Pro Asp Thr Ala Ala Asp Ser Glu Met
            180                 185                 190

Arg Arg Trp Ile Lys Tyr Thr Gln Gln Arg Arg Val Val Gly Glu Phe
        195                 200                 205

Arg Met Asn Lys Ile Trp Leu Asp Ile Val Arg Asn Arg Ile Ala Glu
    210                 215                 220

Asp Leu Ser Leu Arg Arg Phe Met Val Ala Leu Ile Leu Asp Ile Lys
225                 230                 235                 240

Arg Ser Pro Gly Asn Lys Pro Arg Ile Ala Glu Met Ile Cys Asp Ile
                245                 250                 255

Asp Asn Tyr Ile Val Glu Ala Gly Leu Ala Ser Phe Ile Leu Thr Ile
            260                 265                 270

Lys Phe Gly Ile Glu Thr Met Tyr Pro Ala Leu Gly Leu His Glu Phe
        275                 280                 285

Ser Gly Glu Leu Thr Thr Ile Glu Ser Leu Met Met Leu Tyr Gln Gln
    290                 295                 300

Met Gly Glu Thr Ala Pro Tyr Met Val Ile Leu Glu Asn Ser Val Gln
305                 310                 315                 320

Asn Lys Phe Ser Ala Gly Ser Tyr Pro Leu Leu Trp Ser Tyr Ala Met
                325                 330                 335

Gly Val Gly Val Glu Leu Glu Asn Ser Met Gly Gly Leu Asn Phe Gly
            340                 345                 350

Arg Ser Tyr Phe Asp Pro Ala Tyr Phe Arg Leu Gly Gln Glu Met Val
        355                 360                 365

Arg Arg Ser Ala Gly Lys Val Ser Ser Ala Leu Ala Ala Glu Leu Gly
    370                 375                 380

Ile Thr Lys Glu Glu Ala Gln Leu Val Ser Glu Ile Ala Ser Lys Thr
385                 390                 395                 400

Thr Glu Asp Arg Thr Ile Arg Thr Ala Gly Pro Lys Gln Ser Gln Ile
                405                 410                 415

Thr Phe Leu His Ser Glu Arg Ser Glu Val Thr Asn Gln Gln Pro Pro
            420                 425                 430

Thr Ile Asn Lys Arg Ser Glu Asn Gln Gly Gly Asp Lys Tyr Pro Ile
        435                 440                 445

His Phe Asn Asp Glu Arg Phe Pro Gly Tyr Thr Pro Asp Val Asn Ser
    450                 455                 460

Ser Glu Trp Ser Glu Ser Arg Tyr Asp Thr Gln Thr Ile Gln Asp Asp
465                 470                 475                 480

Gly Asn Asp Asp Asp Arg Lys Ser Met Glu Ala Ile Ala Lys Met Arg
                485                 490                 495

Met Leu Thr Lys Met Leu Ser Gln Pro Gly Thr Ser Glu Glu Ser Ser
            500                 505                 510

Pro Val Tyr Asn Asp Arg Glu Leu Leu Asn
        515                 520

<210> SEQ ID NO 9
```

<211> LENGTH: 1626
<212> TYPE: DNA
<213> ORGANISM: Artificial Sequence
<220> FEATURE:
<223> OTHER INFORMATION: Consensus N antigen operably linked to IgE leader sequence

<400> SEQUENCE: 9

```
atggactgga cctggatcct gttcctcgtc gccgccgcca cccgcgtgca ctccgcctcc     60

ctcctcaaga gcctcaccct gttcaagcgg accagggacc agcccccct ggccagcggc    120

tccggaggag ccatccgggg aatcaagcac gtgatcatcg tcctcatccc cggcgacagc    180

tccatcgtga cgcgcagcag actgctcgac cgcctggtga gactcgtcgg agaccccgag    240

atcaacggcc ccaagctgac aggaatcctc atcagcatcc tgtccctctt cgtggagagc    300

cccggccagc tgatccagag gatcatcgac gaccccgacg tgtccatcaa gctcgtggag    360

gtcatcccca gcatcaactc cgtctgcgga ctgacattcg ccagccgggg agccagcctc    420

gactccgagg ccgacgaatt cttcaagatc gtggacgagg gctccaaggc ccagggacag    480

ctgggatggc tcgaaaacaa ggacatcgtg gacatcgagg tcgacgacgc cgaacagttc    540

aacatcctgc tcgccagcat cctggcccag atctggattc tgctcgccaa ggccgtgaca    600

gcccccgaca ccgccgccga ctccgagatg agaaggtgga tcaagtacac gcagcagcgc    660

agagtggtcg gcgaattcag gatgaacaag atctggctgg acatcgtgcg gaacaggatc    720

gccgaggacc tgagcctccg gaggttcatg gtcgccctga tcctcgacat caagcgctcc    780

cccggcaaca agcccagaat cgccgagatg atctgtgaca tcgacaacta catcgtggaa    840

gccggcctgg ccagcttcat cctcaccatc aagttcggaa tcgagacgat gtaccccgcc    900

ctgggactcc acgagttcag cggagaactg accacgatcg agtccctgat gatgctctac    960

cagcagatgg gcgagaccgc cccctacatg gtcatcctcg aaaacagcgt ccagaacaag   1020

ttcagcgccg gcagctaccc cctgctctgg tcctacgcca tgggcgtggg agtcgagctg   1080

gaaaacagca tgggcggact caacttcggc cggagctact tcgaccccgc ctacttcagg   1140

ctgggacagg agatggtgcg cagatccgcc ggaaaggtca gctccgccct ggccgccgaa   1200

ctcggcatca ccaaggagga agcccagctg gtgagcgaga tcgcctccaa gacaaccgaa   1260

gacagaacca tcaggacggc cggacccaag cagagccaga tcacgttcct gcacagcgag   1320

cggtccgaag tcacgaacca gcagcccccc acaatcaaca agaggtccga gaaccagggc   1380

ggagacaagt accccatcca cttcaacgac gaacgcttcc ccggctacac gcccgacgtg   1440

aacagctccg agtggagcga atcccggtac gacacgcaga caatccagga cgacggcaac   1500

gacgacgacc gcaagagcat ggaggccatc gccaagatga gaatgctgac aaagatgctc   1560

agccagcccg gaacctccga ggaaagctcc cccgtgtaca acgaccggga gctgctcaac   1620

tgataa                                                              1626
```

<210> SEQ ID NO 10
<211> LENGTH: 540
<212> TYPE: PRT
<213> ORGANISM: Artificial Sequence
<220> FEATURE:
<223> OTHER INFORMATION: Consensus N antigen operably linked to IgE leader sequence

<400> SEQUENCE: 10

```
Met Asp Trp Thr Trp Ile Leu Phe Leu Val Ala Ala Ala Thr Arg Val
1               5                   10                  15
```

```
His Ser Ala Ser Leu Leu Lys Ser Leu Thr Leu Phe Lys Arg Thr Arg
            20                  25                  30

Asp Gln Pro Pro Leu Ala Ser Gly Ser Gly Gly Ala Ile Arg Gly Ile
        35                  40                  45

Lys His Val Ile Ile Val Leu Ile Pro Gly Asp Ser Ser Ile Val Thr
    50                  55                  60

Arg Ser Arg Leu Leu Asp Arg Leu Val Arg Leu Val Gly Asp Pro Glu
65                  70                  75                  80

Ile Asn Gly Pro Lys Leu Thr Gly Ile Leu Ile Ser Ile Leu Ser Leu
                85                  90                  95

Phe Val Glu Ser Pro Gly Gln Leu Ile Gln Arg Ile Ile Asp Asp Pro
            100                 105                 110

Asp Val Ser Ile Lys Leu Val Glu Val Ile Pro Ser Ile Asn Ser Val
        115                 120                 125

Cys Gly Leu Thr Phe Ala Ser Arg Gly Ala Ser Leu Asp Ser Glu Ala
    130                 135                 140

Asp Glu Phe Phe Lys Ile Val Asp Glu Gly Ser Lys Ala Gln Gly Gln
145                 150                 155                 160

Leu Gly Trp Leu Glu Asn Lys Asp Ile Val Asp Ile Glu Val Asp Asp
                165                 170                 175

Ala Glu Gln Phe Asn Ile Leu Leu Ala Ser Ile Leu Ala Gln Ile Trp
            180                 185                 190

Ile Leu Leu Ala Lys Ala Val Thr Ala Pro Asp Thr Ala Ala Asp Ser
        195                 200                 205

Glu Met Arg Arg Trp Ile Lys Tyr Thr Gln Gln Arg Arg Val Val Gly
    210                 215                 220

Glu Phe Arg Met Asn Lys Ile Trp Leu Asp Ile Val Arg Asn Arg Ile
225                 230                 235                 240

Ala Glu Asp Leu Ser Leu Arg Arg Phe Met Val Ala Leu Ile Leu Asp
                245                 250                 255

Ile Lys Arg Ser Pro Gly Asn Lys Pro Arg Ile Ala Glu Met Ile Cys
            260                 265                 270

Asp Ile Asp Asn Tyr Ile Val Glu Ala Gly Leu Ala Ser Phe Ile Leu
        275                 280                 285

Thr Ile Lys Phe Gly Ile Glu Thr Met Tyr Pro Ala Leu Gly Leu His
    290                 295                 300

Glu Phe Ser Gly Glu Leu Thr Thr Ile Glu Ser Leu Met Met Leu Tyr
305                 310                 315                 320

Gln Gln Met Gly Glu Thr Ala Pro Tyr Met Val Ile Leu Glu Asn Ser
                325                 330                 335

Val Gln Asn Lys Phe Ser Ala Gly Ser Tyr Pro Leu Leu Trp Ser Tyr
            340                 345                 350

Ala Met Gly Val Gly Val Glu Leu Glu Asn Ser Met Gly Gly Leu Asn
        355                 360                 365

Phe Gly Arg Ser Tyr Phe Asp Pro Ala Tyr Phe Arg Leu Gly Gln Glu
    370                 375                 380

Met Val Arg Arg Ser Ala Gly Lys Val Ser Ser Ala Leu Ala Ala Glu
385                 390                 395                 400

Leu Gly Ile Thr Lys Glu Glu Ala Gln Leu Val Ser Glu Ile Ala Ser
                405                 410                 415

Lys Thr Thr Glu Asp Arg Thr Ile Arg Thr Ala Gly Pro Lys Gln Ser
            420                 425                 430

Gln Ile Thr Phe Leu His Ser Glu Arg Ser Glu Val Thr Asn Gln Gln
```

```
        435                 440                 445

Pro Pro Thr Ile Asn Lys Arg Ser Glu Asn Gln Gly Gly Asp Lys Tyr
    450                 455                 460

Pro Ile His Phe Asn Asp Glu Arg Phe Pro Gly Tyr Thr Pro Asp Val
465                 470                 475                 480

Asn Ser Ser Glu Trp Ser Glu Ser Arg Tyr Asp Thr Gln Thr Ile Gln
                485                 490                 495

Asp Asp Gly Asn Asp Asp Asp Arg Lys Ser Met Glu Ala Ile Ala Lys
            500                 505                 510

Met Arg Met Leu Thr Lys Met Leu Ser Gln Pro Gly Thr Ser Glu Glu
        515                 520                 525

Ser Ser Pro Val Tyr Asn Asp Arg Glu Leu Leu Asn
    530                 535                 540


<210> SEQ ID NO 11
<211> LENGTH: 1626
<212> TYPE: DNA
<213> ORGANISM: Artificial Sequence
<220> FEATURE:
<223> OTHER INFORMATION: Optimized N IgE leader sequence

<400> SEQUENCE: 11

atggattgga cttggattct gttcctggtg gcagcagcaa ccagagtgca ctctgcctca      60

ctgctcaaga gcctgactct cttcaaaaga accagggatc agccacccct ggcatccggg     120

agcggcggag ccattagggg catcaagcat gtgatcattg tgctcattcc aggagactcc     180

agcatcgtga ctagatctag gctgctcgat agactggtga ggctcgtggg ggaccctaag     240

atcaacggac caaaactgac cggcatcctg atttccatcc tgagcctctt tgtggagagc     300

ccagggcagc tgatccaaag aatcattgac gatcccgacg tgtccatcaa gctcgtggaa     360

gtgattcctt ctatcaactc agcctgcgga ctgaccttcg cctccagagg cgcctccctc     420

gatagcgagg cagacgaatt ctttaagatc gtggatgagg gatctaaagc ccaggggcaa     480

ctgggctggc tcgaaaataa ggatattgtg gacatcgagg tggacaacgc cgaacagttt     540

aatattctgc tcgcctcaat cctggcccaa atttggattc tgctcgccaa agcagtgaca     600

gcaccagata ctgcagcaga ctccgagatg agaaggtgga ttaagtacac acagcaaaga     660

agggtggtgg gcgagttcag aatgaacaaa atttggctgg atatcgtgag aaataggatc     720

gccgaggacc tgtcactcag aaggttcatg gtggccctga ttctcgatat caagagatcc     780

cccggaaaca aacctaggat cgccgagatg atttgtgata tcgacaatta cattgtggaa     840

gccgggctgg ccagctttat tctcacaatc aagttcggca tcgagactat gtatcccgcc     900

ctgggcctcc acgagttttc aggagaactg accacaattg aatccctgat gatgctctac     960

cagcaaatgg gcgagacagc ccatatatg gtcatcctgg agaacagcgt gcagaacaag    1020

ttctccgccg gatcataccc cctgctctgg tcttatgcca tgggcgtggg agtggagctg    1080

gaaaacagca tgggcggcct gaacttcggc agatcttact ttgatcctgc ctatttcagg    1140

ctgggccagg agatggtgag aaggtcagcc ggaaaggtgt cttcagccct ggccgccgaa    1200

ctcggaatca ctaaggagga agcccaactg gtgtctgaga ttgcctcaaa aactaccgaa    1260

gacagaacca tcagggccac agggcctaaa cagtcccaaa ttacctttct gcactccgag    1320

agaagcgaag tggccaatca gcaacctcca acaatcaaca agaggtcaga aaaccaggga    1380

ggggataaat acccaattca tttctccgac gaaagactgc cagggtatac acccgatgtg    1440

aactccagcg agtggtctga atcaagatac gacactcaga tcattcaaga cgatggcaat    1500
```

```
gacgatgaca gaaagtcaat ggaagccatc gccaagatga ggatgctgac caaaatgctc   1560

tcccaacccg gaacatccga ggataacagc ccagtgtact ctgacaaaga actgctcaat   1620

tgataa                                                              1626


<210> SEQ ID NO 12
<211> LENGTH: 540
<212> TYPE: PRT
<213> ORGANISM: Artificial Sequence
<220> FEATURE:
<223> OTHER INFORMATION: Optimized N IgE leader sequence

<400> SEQUENCE: 12

Met Asp Trp Thr Trp Ile Leu Phe Leu Val Ala Ala Ala Thr Arg Val
1               5                   10                  15

His Ser Ala Ser Leu Leu Lys Ser Leu Thr Leu Phe Lys Arg Thr Arg
            20                  25                  30

Asp Gln Pro Pro Leu Ala Ser Gly Ser Gly Gly Ala Ile Arg Gly Ile
        35                  40                  45

Lys His Val Ile Ile Val Leu Ile Pro Gly Asp Ser Ser Ile Val Thr
    50                  55                  60

Arg Ser Arg Leu Leu Asp Arg Leu Val Arg Leu Val Gly Asp Pro Lys
65                  70                  75                  80

Ile Asn Gly Pro Lys Leu Thr Gly Ile Leu Ile Ser Ile Leu Ser Leu
                85                  90                  95

Phe Val Glu Ser Pro Gly Gln Leu Ile Gln Arg Ile Ile Asp Asp Pro
            100                 105                 110

Asp Val Ser Ile Lys Leu Val Glu Val Ile Pro Ser Ile Asn Ser Ala
        115                 120                 125

Cys Gly Leu Thr Phe Ala Ser Arg Gly Ala Ser Leu Asp Ser Glu Ala
    130                 135                 140

Asp Glu Phe Phe Lys Ile Val Asp Glu Gly Ser Lys Ala Gln Gly Gln
145                 150                 155                 160

Leu Gly Trp Leu Glu Asn Lys Asp Ile Val Asp Ile Glu Val Asp Asn
                165                 170                 175

Ala Glu Gln Phe Asn Ile Leu Leu Ala Ser Ile Leu Ala Gln Ile Trp
            180                 185                 190

Ile Leu Leu Ala Lys Ala Val Thr Ala Pro Asp Thr Ala Ala Asp Ser
        195                 200                 205

Glu Met Arg Arg Trp Ile Lys Tyr Thr Gln Gln Arg Arg Val Val Gly
    210                 215                 220

Glu Phe Arg Met Asn Lys Ile Trp Leu Asp Ile Val Arg Asn Arg Ile
225                 230                 235                 240

Ala Glu Asp Leu Ser Leu Arg Arg Phe Met Val Ala Leu Ile Leu Asp
                245                 250                 255

Ile Lys Arg Ser Pro Gly Asn Lys Pro Arg Ile Ala Glu Met Ile Cys
            260                 265                 270

Asp Ile Asp Asn Tyr Ile Val Glu Ala Gly Leu Ala Ser Phe Ile Leu
        275                 280                 285

Thr Ile Lys Phe Gly Ile Glu Thr Met Tyr Pro Ala Leu Gly Leu His
    290                 295                 300

Glu Phe Ser Gly Glu Leu Thr Thr Ile Glu Ser Leu Met Met Leu Tyr
305                 310                 315                 320

Gln Gln Met Gly Glu Thr Ala Pro Tyr Met Val Ile Leu Glu Asn Ser
                325                 330                 335
```

```
Val Gln Asn Lys Phe Ser Ala Gly Ser Tyr Pro Leu Leu Trp Ser Tyr
            340                 345                 350

Ala Met Gly Val Gly Val Glu Leu Glu Asn Ser Met Gly Gly Leu Asn
        355                 360                 365

Phe Gly Arg Ser Tyr Phe Asp Pro Ala Tyr Phe Arg Leu Gly Gln Glu
    370                 375                 380

Met Val Arg Arg Ser Ala Gly Lys Val Ser Ser Ala Leu Ala Ala Glu
385                 390                 395                 400

Leu Gly Ile Thr Lys Glu Glu Ala Gln Leu Val Ser Glu Ile Ala Ser
                405                 410                 415

Lys Thr Thr Glu Asp Arg Thr Ile Arg Ala Thr Gly Pro Lys Gln Ser
            420                 425                 430

Gln Ile Thr Phe Leu His Ser Glu Arg Ser Glu Val Ala Asn Gln Gln
        435                 440                 445

Pro Pro Thr Ile Asn Lys Arg Ser Glu Asn Gln Gly Gly Asp Lys Tyr
    450                 455                 460

Pro Ile His Phe Ser Asp Glu Arg Leu Pro Gly Tyr Thr Pro Asp Val
465                 470                 475                 480

Asn Ser Ser Glu Trp Ser Glu Ser Arg Tyr Asp Thr Gln Ile Ile Gln
                485                 490                 495

Asp Asp Gly Asn Asp Asp Asp Arg Lys Ser Met Glu Ala Ile Ala Lys
            500                 505                 510

Met Arg Met Leu Thr Lys Met Leu Ser Gln Pro Gly Thr Ser Glu Asp
        515                 520                 525

Asn Ser Pro Val Tyr Ser Asp Lys Glu Leu Leu Asn
    530                 535                 540
```

```
<210> SEQ ID NO 13
<211> LENGTH: 1581
<212> TYPE: DNA
<213> ORGANISM: Artificial Sequence
<220> FEATURE:
<223> OTHER INFORMATION: Consensus F antigen

<400> SEQUENCE: 13

cagatccact ggaacaatct gagcacaatt ggcatcattg gaactgactc tgtgcactat     60

aagatcatga ctaggccatc ccatcaatac ctcgtgatca agctcatgcc caacgtgagc    120

ctgattgata attgtacaaa ggccgaactc ggcgagtatg aaaaactgct caactctgtg    180

ctggagccca tcaatcaggc cctgactctc atgaccaaca atgtgaaacc tctgcagtct    240

gtgggatcag ggagaaggca aagaaggttc gcaggagtgg tgctggcagg agccgccctc    300

ggagtggcaa cagcagcaca gatcactgca ggaattgccc tgcatcaatc aaacctcaat    360

gcccaggcca tccaatccct gagaaccagc ctcgaacaat ctaacaaggc catcgaggaa    420

attagggagg ccacacaaga aactgtgatt gccgtgcagg gagtgcaaga ctacgtgaac    480

aatgaactgg tgccagccat gcagcacatg tcctgtgagc tcgtggggca aagactgggc    540

ctcaaactgc tcaggtacta tacagaactg ctctcaatct ttgggccttc cctgagagat    600

ccaatttcag ccgagatctc cattcaggcc ctgagctatg ccctcggcgg agagatccat    660

aagattctgg aaaaactcgg gtacagcggc aatgacatga tcgccattct ggagtctaga    720

ggaatcaaga ccaaaattac acacgtggat ctccctggga agctgatcat tctctccatc    780

agctatccaa ccctgtctga ggtgaaaggc gtgatcgtgc ataggctcga agccgtgagc    840

tacaacattg gctctcagga gtggtacacc acagtgccca agtatgtggc cacaaacgga    900
```

```
tacctgatct ctaatttcga cgagtcttca tgcgtgttcg tgtccgaatc agccatttgt    960

tcccaaaata gcctgtatcc catgtcacct atcctccagc aatgcattag aggggatacc   1020

tccagctgtg ccaggaccct ggtgtcagga acaatgggga acaagttcat cctctccaaa   1080

ggcaacattg tggccaattg cgccagcatc ctgtgcaagt gttactccac aagcactatc   1140

attaatcagt ctcctgacaa actgctcacc tttattgcct cagacacatg tccactggtg   1200

gaaatcgatg gcgtgaccat tcaagtgggc ggcagacagt accccgacat ggtgtatgaa   1260

tcaaaggtgg ccctgggacc tgccatctcc ctggagaggc tcgatgtggg aacaaacctg   1320

gggaatgccc tgaagaaact cgacgatgcc aaggtgctga tcgattcttc aaaccagatc   1380

ctggagaccg tgaaaagatc cagcttcaat tttggctctc tgctctcagt gcccatcctg   1440

atttgcacag ccctcgccct gctcctgctc atctattgct gtaaaagaag gtacagacaa   1500

actttcaagc acaacaccaa agtggaccca accttcaagc ccgatctgac cggaacatct   1560

aaatcatacg tgaggagcct c                                              1581


<210> SEQ ID NO 14
<211> LENGTH: 527
<212> TYPE: PRT
<213> ORGANISM: Artificial Sequence
<220> FEATURE:
<223> OTHER INFORMATION: Consensus F antigen

<400> SEQUENCE: 14

Gln Ile His Trp Asn Asn Leu Ser Thr Ile Gly Ile Ile Gly Thr Asp
1               5                   10                  15

Ser Val His Tyr Lys Ile Met Thr Arg Pro Ser His Gln Tyr Leu Val
            20                  25                  30

Ile Lys Leu Met Pro Asn Val Ser Leu Ile Asp Asn Cys Thr Lys Ala
        35                  40                  45

Glu Leu Gly Glu Tyr Glu Lys Leu Leu Asn Ser Val Leu Glu Pro Ile
    50                  55                  60

Asn Gln Ala Leu Thr Leu Met Thr Asn Asn Val Lys Pro Leu Gln Ser
65                  70                  75                  80

Val Gly Ser Gly Arg Arg Gln Arg Arg Phe Ala Gly Val Val Leu Ala
                85                  90                  95

Gly Ala Ala Leu Gly Val Ala Thr Ala Ala Gln Ile Thr Ala Gly Ile
            100                 105                 110

Ala Leu His Gln Ser Asn Leu Asn Ala Gln Ala Ile Gln Ser Leu Arg
        115                 120                 125

Thr Ser Leu Glu Gln Ser Asn Lys Ala Ile Glu Glu Ile Arg Glu Ala
    130                 135                 140

Thr Gln Glu Thr Val Ile Ala Val Gln Gly Val Gln Asp Tyr Val Asn
145                 150                 155                 160

Asn Glu Leu Val Pro Ala Met Gln His Met Ser Cys Glu Leu Val Gly
                165                 170                 175

Gln Arg Leu Gly Leu Lys Leu Leu Arg Tyr Tyr Thr Glu Leu Leu Ser
            180                 185                 190

Ile Phe Gly Pro Ser Leu Arg Asp Pro Ile Ser Ala Glu Ile Ser Ile
        195                 200                 205

Gln Ala Leu Ser Tyr Ala Leu Gly Gly Glu Ile His Lys Ile Leu Glu
    210                 215                 220

Lys Leu Gly Tyr Ser Gly Asn Asp Met Ile Ala Ile Leu Glu Ser Arg
225                 230                 235                 240
```

```
Gly Ile Lys Thr Lys Ile Thr His Val Asp Leu Pro Gly Lys Leu Ile
                245                 250                 255

Ile Leu Ser Ile Ser Tyr Pro Thr Leu Ser Glu Val Lys Gly Val Ile
            260                 265                 270

Val His Arg Leu Glu Ala Val Ser Tyr Asn Ile Gly Ser Gln Glu Trp
        275                 280                 285

Tyr Thr Thr Val Pro Lys Tyr Val Ala Thr Asn Gly Tyr Leu Ile Ser
    290                 295                 300

Asn Phe Asp Glu Ser Ser Cys Val Phe Val Ser Glu Ser Ala Ile Cys
305                 310                 315                 320

Ser Gln Asn Ser Leu Tyr Pro Met Ser Pro Ile Leu Gln Gln Cys Ile
                325                 330                 335

Arg Gly Asp Thr Ser Ser Cys Ala Arg Thr Leu Val Ser Gly Thr Met
            340                 345                 350

Gly Asn Lys Phe Ile Leu Ser Lys Gly Asn Ile Val Ala Asn Cys Ala
        355                 360                 365

Ser Ile Leu Cys Lys Cys Tyr Ser Thr Ser Thr Ile Ile Asn Gln Ser
    370                 375                 380

Pro Asp Lys Leu Leu Thr Phe Ile Ala Ser Asp Thr Cys Pro Leu Val
385                 390                 395                 400

Glu Ile Asp Gly Val Thr Ile Gln Val Gly Gly Arg Gln Tyr Pro Asp
                405                 410                 415

Met Val Tyr Glu Ser Lys Val Ala Leu Gly Pro Ala Ile Ser Leu Glu
            420                 425                 430

Arg Leu Asp Val Gly Thr Asn Leu Gly Asn Ala Leu Lys Lys Leu Asp
        435                 440                 445

Asp Ala Lys Val Leu Ile Asp Ser Ser Asn Gln Ile Leu Glu Thr Val
    450                 455                 460

Lys Arg Ser Ser Phe Asn Phe Gly Ser Leu Leu Ser Val Pro Ile Leu
465                 470                 475                 480

Ile Cys Thr Ala Leu Ala Leu Leu Leu Leu Ile Tyr Cys Cys Lys Arg
                485                 490                 495

Arg Tyr Arg Gln Thr Phe Lys His Asn Thr Lys Val Asp Pro Thr Phe
            500                 505                 510

Lys Pro Asp Leu Thr Gly Thr Ser Lys Ser Tyr Val Arg Ser Leu
        515                 520                 525
```

<210> SEQ ID NO 15
<211> LENGTH: 1992
<212> TYPE: DNA
<213> ORGANISM: Artificial Sequence
<220> FEATURE:
<223> OTHER INFORMATION: Consensus F antigen operably linked to endo leader sequence

<400> SEQUENCE: 15

```
atgcacaaca agatcccaaa gaaatccaaa cctctgccac acacaagaca ggaccccctc      60

cagcaacatt ccactaagag cgccgaaact aaaaccagcc agggcagaca ttctatcact     120

tcagcccaaa ggtcaaccca ccatggaccc agaacatccg ataggcctgt gcactatatc     180

atgaacagaa ctaggtcctg caagcagacc tcccatagaa gcgacaatat tccaccccac     240

agggatcatg agggcatcat tcaccatact cctgaatctg tgacccaagg agcctccagc     300

tggttcaaga gaaggcagtc aaacgccact aattctgggt cacaatgcac ctggctggtg     360

ctctggtgta tcggcattgc cagcctgttt ctctgctcta aagcccagat ccactggaac     420
```

```
aatctgagca caattggcat cattggaact gactctgtgc actataagat catgactagg    480

ccatcccatc aatacctcgt gatcaagctc atgcccaacg tgagcctgat tgataattgt    540

acaaaggccg aactcggcga gtatgaaaaa ctgctcaact ctgtgctgga gcccatcaat    600

caggccctga ctctcatgac caacaatgtg aaacctctgc agtctgtggg atcagggaga    660

aggcaaagaa ggttcgcagg agtggtgctg gcaggagccg ccctcggagt ggcaacagca    720

gcacagatca ctgcaggaat tgccctgcat caatcaaacc tcaatgccca ggccatccaa    780

tccctgagaa ccagcctcga acaatctaac aaggccatcg aggaaattag ggaggccaca    840

caagaaactg tgattgccgt gcagggagtg caagactacg tgaacaatga actggtgcca    900

gccatgcagc acatgtcctg tgagctcgtg gggcaaagac tgggcctcaa actgctcagg    960

tactatacag aactgctctc aatctttggg ccttccctga gagatccaat ttcagccgag   1020

atctccattc aggccctgag ctatgccctc ggcggagaga tccataagat tctggaaaaa   1080

ctcgggtaca gcggcaatga catgatcgcc attctggagt ctagaggaat caagaccaaa   1140

attacacacg tggatctccc tgggaagctg atcattctct ccatcagcta tccaaccctg   1200

tctgaggtga aaggcgtgat cgtgcatagg ctcgaagccg tgagctacaa cattggctct   1260

caggagtggt acaccacagt gcccaagtat gtggccacaa acggatacct gatctctaat   1320

ttcgacgagt cttcatgcgt gttcgtgtcc gaatcagcca tttgttccca aaatagcctg   1380

tatcccatgt cacctatcct ccagcaatgc attagagggg atacctccag ctgtgccagg   1440

accctggtgt caggaacaat ggggaacaag ttcatcctct ccaaaggcaa cattgtggcc   1500

aattgcgcca gcatcctgtg caagtgttac tccacaagca ctatcattaa tcagtctcct   1560

gacaaactgc tcacctttat tgcctcagac acatgtccac tggtggaaat cgatggcgtg   1620

accattcaag tgggcggcag acagtacccc gacatggtgt atgaatcaaa ggtggccctg   1680

ggacctgcca tctccctgga gaggctcgat gtgggaacaa acctggggaa tgccctgaag   1740

aaactcgacg atgccaaggt gctgatcgat tcttcaaacc agatcctgga gaccgtgaaa   1800

agatccagct tcaattttgg ctctctgctc tcagtgccca tcctgatttg cacagccctc   1860

gccctgctcc tgctcatcta ttgctgtaaa agaaggtaca gacaaacttt caagcacaac   1920

accaaagtgg acccaacctt caagcccgat ctgaccggaa catctaaatc atacgtgagg   1980

agcctctgat aa                                                       1992
```

```
<210> SEQ ID NO 16
<211> LENGTH: 662
<212> TYPE: PRT
<213> ORGANISM: Artificial Sequence
<220> FEATURE:
<223> OTHER INFORMATION: Consensus F antigen operably linked to endo
      leader sequence

<400> SEQUENCE: 16

Met His Asn Lys Ile Pro Lys Lys Ser Lys Pro Leu Pro His Thr Arg
1               5                   10                  15

Gln Asp Pro Leu Gln Gln His Ser Thr Lys Ser Ala Glu Thr Lys Thr
            20                  25                  30

Ser Gln Gly Arg His Ser Ile Thr Ser Ala Gln Arg Ser Thr His His
        35                  40                  45

Gly Pro Arg Thr Ser Asp Arg Pro Val His Tyr Ile Met Asn Arg Thr
    50                  55                  60

Arg Ser Cys Lys Gln Thr Ser His Arg Ser Asp Asn Ile Pro Pro His
```

```
65                  70                  75                  80

Arg Asp His Glu Gly Ile Ile His His Thr Pro Glu Ser Val Thr Gln
                85                  90                  95

Gly Ala Ser Ser Trp Phe Lys Arg Arg Gln Ser Asn Ala Thr Asn Ser
            100                 105                 110

Gly Ser Gln Cys Thr Trp Leu Val Leu Trp Cys Ile Gly Ile Ala Ser
        115                 120                 125

Leu Phe Leu Cys Ser Lys Ala Gln Ile His Trp Asn Asn Leu Ser Thr
    130                 135                 140

Ile Gly Ile Ile Gly Thr Asp Ser Val His Tyr Lys Ile Met Thr Arg
145                 150                 155                 160

Pro Ser His Gln Tyr Leu Val Ile Lys Leu Met Pro Asn Val Ser Leu
                165                 170                 175

Ile Asp Asn Cys Thr Lys Ala Glu Leu Gly Glu Tyr Glu Lys Leu Leu
            180                 185                 190

Asn Ser Val Leu Glu Pro Ile Asn Gln Ala Leu Thr Leu Met Thr Asn
        195                 200                 205

Asn Val Lys Pro Leu Gln Ser Val Gly Ser Gly Arg Arg Gln Arg Arg
    210                 215                 220

Phe Ala Gly Val Val Leu Ala Gly Ala Ala Leu Gly Val Ala Thr Ala
225                 230                 235                 240

Ala Gln Ile Thr Ala Gly Ile Ala Leu His Gln Ser Asn Leu Asn Ala
                245                 250                 255

Gln Ala Ile Gln Ser Leu Arg Thr Ser Leu Glu Gln Ser Asn Lys Ala
            260                 265                 270

Ile Glu Glu Ile Arg Glu Ala Thr Gln Glu Thr Val Ile Ala Val Gln
        275                 280                 285

Gly Val Gln Asp Tyr Val Asn Asn Glu Leu Val Pro Ala Met Gln His
    290                 295                 300

Met Ser Cys Glu Leu Val Gly Gln Arg Leu Gly Leu Lys Leu Leu Arg
305                 310                 315                 320

Tyr Tyr Thr Glu Leu Leu Ser Ile Phe Gly Pro Ser Leu Arg Asp Pro
                325                 330                 335

Ile Ser Ala Glu Ile Ser Ile Gln Ala Leu Ser Tyr Ala Leu Gly Gly
            340                 345                 350

Glu Ile His Lys Ile Leu Glu Lys Leu Gly Tyr Ser Gly Asn Asp Met
        355                 360                 365

Ile Ala Ile Leu Glu Ser Arg Gly Ile Lys Thr Lys Ile Thr His Val
    370                 375                 380

Asp Leu Pro Gly Lys Leu Ile Ile Leu Ser Ile Ser Tyr Pro Thr Leu
385                 390                 395                 400

Ser Glu Val Lys Gly Val Ile Val His Arg Leu Glu Ala Val Ser Tyr
                405                 410                 415

Asn Ile Gly Ser Gln Glu Trp Tyr Thr Thr Val Pro Lys Tyr Val Ala
            420                 425                 430

Thr Asn Gly Tyr Leu Ile Ser Asn Phe Asp Glu Ser Ser Cys Val Phe
        435                 440                 445

Val Ser Glu Ser Ala Ile Cys Ser Gln Asn Ser Leu Tyr Pro Met Ser
    450                 455                 460

Pro Ile Leu Gln Gln Cys Ile Arg Gly Asp Thr Ser Ser Cys Ala Arg
465                 470                 475                 480

Thr Leu Val Ser Gly Thr Met Gly Asn Lys Phe Ile Leu Ser Lys Gly
                485                 490                 495
```

```
Asn Ile Val Ala Asn Cys Ala Ser Ile Leu Cys Lys Cys Tyr Ser Thr
            500                 505                 510

Ser Thr Ile Ile Asn Gln Ser Pro Asp Lys Leu Leu Thr Phe Ile Ala
        515                 520                 525

Ser Asp Thr Cys Pro Leu Val Glu Ile Asp Gly Val Thr Ile Gln Val
    530                 535                 540

Gly Gly Arg Gln Tyr Pro Asp Met Val Tyr Glu Ser Lys Val Ala Leu
545                 550                 555                 560

Gly Pro Ala Ile Ser Leu Glu Arg Leu Asp Val Gly Thr Asn Leu Gly
                565                 570                 575

Asn Ala Leu Lys Lys Leu Asp Asp Ala Lys Val Leu Ile Asp Ser Ser
            580                 585                 590

Asn Gln Ile Leu Glu Thr Val Lys Arg Ser Ser Phe Asn Phe Gly Ser
        595                 600                 605

Leu Leu Ser Val Pro Ile Leu Ile Cys Thr Ala Leu Ala Leu Leu Leu
    610                 615                 620

Leu Ile Tyr Cys Cys Lys Arg Arg Tyr Arg Gln Thr Phe Lys His Asn
625                 630                 635                 640

Thr Lys Val Asp Pro Thr Phe Lys Pro Asp Leu Thr Gly Thr Ser Lys
                645                 650                 655

Ser Tyr Val Arg Ser Leu
            660
```

<210> SEQ ID NO 17
<211> LENGTH: 1641
<212> TYPE: DNA
<213> ORGANISM: Artificial Sequence
<220> FEATURE:
<223> OTHER INFORMATION: Consensus F antigen operably linked to IgE leader sequence

<400> SEQUENCE: 17

```
atggactgga cttggattct gttcctggtg gcagcagcaa ccagagtgca ctcacagatc     60

cactggaaca atctgagcac aattggcatc attggaactg actctgtgca ctataagatc    120

atgactaggc catcccatca atacctcgtg atcaagctca tgcccaacgt gagcctgatt    180

gataattgta caaaggccga actcggcgag tatgaaaaac tgctcaactc tgtgctggag    240

cccatcaatc aggccctgac tctcatgacc aacaatgtga aacctctgca gtctgtggga    300

tcagggagaa ggcaaagaag gttcgcagga gtggtgctgg caggagccgc cctcggagtg    360

gcaacagcag cacagatcac tgcaggaatt gccctgcatc aatcaaacct caatgcccag    420

gccatccaat ccctgagaac cagcctcgaa caatctaaca aggccatcga ggaaattagg    480

gaggccacac aagaaactgt gattgccgtg cagggagtgc aagactacgt gaacaatgaa    540

ctggtgccag ccatgcagca catgtcctgt gagctcgtgg ggcaaagact gggcctcaaa    600

ctgctcaggt actatacaga actgctctca atctttgggc cttccctgag agatccaatt    660

tcagccgaga tctccattca ggccctgagc tatgccctcg gcggagagat ccataagatt    720

ctggaaaaac tcgggtacag cggcaatgac atgatcgcca ttctggagtc tagaggaatc    780

aagaccaaaa ttacacacgt ggatctccct gggaagctga tcattctctc catcagctat    840

ccaaccctgt ctgaggtgaa aggcgtgatc gtgcataggc tcgaagccgt gagctacaac    900

attggctctc aggagtggta caccacagtg cccaagtatg tggccacaaa cggatacctg    960

atctctaatt tcgacgagtc ttcatgcgtg ttcgtgtccg aatcagccat ttgttcccaa   1020
```

```
aatagcctgt atcccatgtc acctatcctc cagcaatgca ttagagggga tacctccagc   1080

tgtgccagga ccctggtgtc aggaacaatg gggaacaagt tcatcctctc caaaggcaac   1140

attgtggcca attgcgccag catcctgtgc aagtgttact ccacaagcac tatcattaat   1200

cagtctcctg acaaactgct cacctttatt gcctcagaca catgtccact ggtggaaatc   1260

gatggcgtga ccattcaagt gggcggcaga cagtaccccg acatggtgta tgaatcaaag   1320

gtggccctgg gacctgccat ctccctggag aggctcgatg tgggaacaaa cctggggaat   1380

gccctgaaga aactcgacga tgccaaggtg ctgatcgatt cttcaaacca gatcctggag   1440

accgtgaaaa gatccagctt caattttggc tctctgctct cagtgcccat cctgatttgc   1500

acagccctcg ccctgctcct gctcatctat tgctgtaaaa gaaggtacag acaaactttc   1560

aagcacaaca ccaaagtgga cccaaccttc aagcccgatc tgaccggaac atctaaatca   1620

tacgtgagga gcctctgata a                                             1641
```

```
<210> SEQ ID NO 18
<211> LENGTH: 545
<212> TYPE: PRT
<213> ORGANISM: Artificial Sequence
<220> FEATURE:
<223> OTHER INFORMATION: Consensus F antigen operably linked to IgE
      leader sequence

<400> SEQUENCE: 18

Met Asp Trp Thr Trp Ile Leu Phe Leu Val Ala Ala Ala Thr Arg Val
1               5                   10                  15

His Ser Gln Ile His Trp Asn Asn Leu Ser Thr Ile Gly Ile Ile Gly
            20                  25                  30

Thr Asp Ser Val His Tyr Lys Ile Met Thr Arg Pro Ser His Gln Tyr
        35                  40                  45

Leu Val Ile Lys Leu Met Pro Asn Val Ser Leu Ile Asp Asn Cys Thr
    50                  55                  60

Lys Ala Glu Leu Gly Glu Tyr Glu Lys Leu Leu Asn Ser Val Leu Glu
65                  70                  75                  80

Pro Ile Asn Gln Ala Leu Thr Leu Met Thr Asn Asn Val Lys Pro Leu
                85                  90                  95

Gln Ser Val Gly Ser Gly Arg Arg Gln Arg Arg Phe Ala Gly Val Val
            100                 105                 110

Leu Ala Gly Ala Ala Leu Gly Val Ala Thr Ala Ala Gln Ile Thr Ala
        115                 120                 125

Gly Ile Ala Leu His Gln Ser Asn Leu Asn Ala Gln Ala Ile Gln Ser
    130                 135                 140

Leu Arg Thr Ser Leu Glu Gln Ser Asn Lys Ala Ile Glu Glu Ile Arg
145                 150                 155                 160

Glu Ala Thr Gln Glu Thr Val Ile Ala Val Gln Gly Val Gln Asp Tyr
                165                 170                 175

Val Asn Asn Glu Leu Val Pro Ala Met Gln His Met Ser Cys Glu Leu
            180                 185                 190

Val Gly Gln Arg Leu Gly Leu Lys Leu Leu Arg Tyr Tyr Thr Glu Leu
        195                 200                 205

Leu Ser Ile Phe Gly Pro Ser Leu Arg Asp Pro Ile Ser Ala Glu Ile
    210                 215                 220

Ser Ile Gln Ala Leu Ser Tyr Ala Leu Gly Gly Glu Ile His Lys Ile
225                 230                 235                 240

Leu Glu Lys Leu Gly Tyr Ser Gly Asn Asp Met Ile Ala Ile Leu Glu
```

```
                245                 250                 255

Ser Arg Gly Ile Lys Thr Lys Ile Thr His Val Asp Leu Pro Gly Lys
            260                 265                 270

Leu Ile Ile Leu Ser Ile Ser Tyr Pro Thr Leu Ser Glu Val Lys Gly
        275                 280                 285

Val Ile Val His Arg Leu Glu Ala Val Ser Tyr Asn Ile Gly Ser Gln
    290                 295                 300

Glu Trp Tyr Thr Thr Val Pro Lys Tyr Val Ala Thr Asn Gly Tyr Leu
305                 310                 315                 320

Ile Ser Asn Phe Asp Glu Ser Ser Cys Val Phe Val Ser Glu Ser Ala
                325                 330                 335

Ile Cys Ser Gln Asn Ser Leu Tyr Pro Met Ser Pro Ile Leu Gln Gln
            340                 345                 350

Cys Ile Arg Gly Asp Thr Ser Ser Cys Ala Arg Thr Leu Val Ser Gly
        355                 360                 365

Thr Met Gly Asn Lys Phe Ile Leu Ser Lys Gly Asn Ile Val Ala Asn
    370                 375                 380

Cys Ala Ser Ile Leu Cys Lys Cys Tyr Ser Thr Ser Thr Ile Ile Asn
385                 390                 395                 400

Gln Ser Pro Asp Lys Leu Leu Thr Phe Ile Ala Ser Asp Thr Cys Pro
                405                 410                 415

Leu Val Glu Ile Asp Gly Val Thr Ile Gln Val Gly Gly Arg Gln Tyr
            420                 425                 430

Pro Asp Met Val Tyr Glu Ser Lys Val Ala Leu Gly Pro Ala Ile Ser
        435                 440                 445

Leu Glu Arg Leu Asp Val Gly Thr Asn Leu Gly Asn Ala Leu Lys Lys
    450                 455                 460

Leu Asp Asp Ala Lys Val Leu Ile Asp Ser Ser Asn Gln Ile Leu Glu
465                 470                 475                 480

Thr Val Lys Arg Ser Ser Phe Asn Phe Gly Ser Leu Leu Ser Val Pro
                485                 490                 495

Ile Leu Ile Cys Thr Ala Leu Ala Leu Leu Leu Leu Ile Tyr Cys Cys
            500                 505                 510

Lys Arg Arg Tyr Arg Gln Thr Phe Lys His Asn Thr Lys Val Asp Pro
        515                 520                 525

Thr Phe Lys Pro Asp Leu Thr Gly Thr Ser Lys Ser Tyr Val Arg Ser
    530                 535                 540

Leu
545
```

<210> SEQ ID NO 19
<211> LENGTH: 1641
<212> TYPE: DNA
<213> ORGANISM: Artificial Sequence
<220> FEATURE:
<223> OTHER INFORMATION: Optimized F with IgE leader sequence

<400> SEQUENCE: 19

```
atggactgga catggattct gttcctggtg gccgccgcca ctagagtgca cagccagatc     60

cattgggaca acctgagcac tattggcatc attggaaccg ataatgtgca ctataagatc    120

atgacaaggc cctctcatca atacctcgtg atcaagctca ttcctaacgc ctcactcatt    180

gagaattgta ctaaggccga actgggagag tatgaaaaac tgctcaacag cgtgctggaa    240

cctatcaatc aggccctgac actcatgact aagaacgtga aaccactgca gtctctcgga    300
```

```
tcagggagaa ggcaaagaag gtttgccgga gtggtgctgg caggagtggc cctcggagtg    360
gcaaccgcag cacagatcac agcaggaatt gccctgcacc aaagcaacct caatgcccag    420
gccatccaat ccctgaggac aagcctggag cagtctaata aggccatcga ggaaattaga    480
gaggccaccc aagaaacagt gattgccgtg caggggggtgc aagactacgt gaacaatgaa    540
ctcgtgccag ccatgcagca catgtcttgc gagctggtgg ggcaaaggct gggcctcagg    600
ctgctcagat actataccga actgctctca atcttcggcc catccctgag agatcccatt    660
tcagccgaga tctccattca ggccctgatc tatgccctcg gcggagagat ccataagatt    720
ctggaaaaac tcgggtactc tggctcagac atgatcgcca ttctggaatc tagaggaatc    780
aagactaaaa ttacccacgt ggatctgcct gggaagttta tcattctctc catcagctat    840
cccactctgt cagaggtgaa aggcgtgatc gtgcataggc tggaagccgt gagctacaac    900
attggatctc aggagtggta cactaccgtg cccagatata tcgccaccaa cggctacctc    960
atttccaatt tcgacgagtc ttcatgcgtg ttcgtgtccg aatcagccat ctgttcccaa   1020
aatagcctgt atcctatgag cccactgctc cagcaatgca ttaggggcga tacatccagc   1080
tgtgccagaa ctctcgtgag cggaaccatg ggaacaagt tcatcctgtc taaaggaaac   1140
attgtggcca attgcgcctc aatcctctgc aagtgttact ccaccagcac aatcattaat   1200
cagtccccag acaaactgct gaccttcatc gccagcgaca cttgtcccct ggtggaaatc   1260
gatggagcca ccattcaagt gggcggcaga cagtaccctg atatggtgta tgagggcaag   1320
gtggccctcg gaccagccat ctccctggac agactcgatg tgggaacaaa cctggggaat   1380
gccctgaaga aactcgacga tgccaaagtg ctcatcgatt cttcaaacca gattctggag   1440
actgtgagaa ggtccagctt caattttgga tctctgctct cagtgcccat cctgtcttgt   1500
accgccctcg ccctgctcct gctcatctac tgctgtaaaa gaaggtacca gcaaacactg   1560
aagcaacata ctaaagtgga ccccgccttc aagcctgatc tcactgggac ctctaaatca   1620
tatgtgagat cactgtgata a                                             1641
```

<210> SEQ ID NO 20
<211> LENGTH: 545
<212> TYPE: PRT
<213> ORGANISM: Artificial Sequence
<220> FEATURE:
<223> OTHER INFORMATION: Optimized F with IgE leader sequence

<400> SEQUENCE: 20

```
Met Asp Trp Thr Trp Ile Leu Phe Leu Val Ala Ala Ala Thr Arg Val
1               5                   10                  15

His Ser Gln Ile His Trp Asp Asn Leu Ser Thr Ile Gly Ile Ile Gly
            20                  25                  30

Thr Asp Asn Val His Tyr Lys Ile Met Thr Arg Pro Ser His Gln Tyr
        35                  40                  45

Leu Val Ile Lys Leu Ile Pro Asn Ala Ser Leu Ile Glu Asn Cys Thr
    50                  55                  60

Lys Ala Glu Leu Gly Glu Tyr Glu Lys Leu Leu Asn Ser Val Leu Glu
65                  70                  75                  80

Pro Ile Asn Gln Ala Leu Thr Leu Met Thr Lys Asn Val Lys Pro Leu
                85                  90                  95

Gln Ser Leu Gly Ser Gly Arg Arg Gln Arg Arg Phe Ala Gly Val Val
            100                 105                 110

Leu Ala Gly Val Ala Leu Gly Val Ala Thr Ala Ala Gln Ile Thr Ala
        115                 120                 125
```

```
Gly Ile Ala Leu His Gln Ser Asn Leu Asn Ala Gln Ala Ile Gln Ser
    130                 135                 140

Leu Arg Thr Ser Leu Glu Gln Ser Asn Lys Ala Ile Glu Glu Ile Arg
145                 150                 155                 160

Glu Ala Thr Gln Glu Thr Val Ile Ala Val Gln Gly Val Gln Asp Tyr
                165                 170                 175

Val Asn Asn Glu Leu Val Pro Ala Met Gln His Met Ser Cys Glu Leu
            180                 185                 190

Val Gly Gln Arg Leu Gly Leu Arg Leu Leu Arg Tyr Tyr Thr Glu Leu
        195                 200                 205

Leu Ser Ile Phe Gly Pro Ser Leu Arg Asp Pro Ile Ser Ala Glu Ile
    210                 215                 220

Ser Ile Gln Ala Leu Ile Tyr Ala Leu Gly Gly Glu Ile His Lys Ile
225                 230                 235                 240

Leu Glu Lys Leu Gly Tyr Ser Gly Ser Asp Met Ile Ala Ile Leu Glu
                245                 250                 255

Ser Arg Gly Ile Lys Thr Lys Ile Thr His Val Asp Leu Pro Gly Lys
            260                 265                 270

Phe Ile Ile Leu Ser Ile Ser Tyr Pro Thr Leu Ser Glu Val Lys Gly
        275                 280                 285

Val Ile Val His Arg Leu Glu Ala Val Ser Tyr Asn Ile Gly Ser Gln
    290                 295                 300

Glu Trp Tyr Thr Thr Val Pro Arg Tyr Ile Ala Thr Asn Gly Tyr Leu
305                 310                 315                 320

Ile Ser Asn Phe Asp Glu Ser Ser Cys Val Phe Val Ser Glu Ser Ala
                325                 330                 335

Ile Cys Ser Gln Asn Ser Leu Tyr Pro Met Ser Pro Leu Leu Gln Gln
            340                 345                 350

Cys Ile Arg Gly Asp Thr Ser Ser Cys Ala Arg Thr Leu Val Ser Gly
        355                 360                 365

Thr Met Gly Asn Lys Phe Ile Leu Ser Lys Gly Asn Ile Val Ala Asn
    370                 375                 380

Cys Ala Ser Ile Leu Cys Lys Cys Tyr Ser Thr Ser Thr Ile Ile Asn
385                 390                 395                 400

Gln Ser Pro Asp Lys Leu Leu Thr Phe Ile Ala Ser Asp Thr Cys Pro
                405                 410                 415

Leu Val Glu Ile Asp Gly Ala Thr Ile Gln Val Gly Gly Arg Gln Tyr
            420                 425                 430

Pro Asp Met Val Tyr Glu Gly Lys Val Ala Leu Gly Pro Ala Ile Ser
        435                 440                 445

Leu Asp Arg Leu Asp Val Gly Thr Asn Leu Gly Asn Ala Leu Lys Lys
    450                 455                 460

Leu Asp Asp Ala Lys Val Leu Ile Asp Ser Ser Asn Gln Ile Leu Glu
465                 470                 475                 480

Thr Val Arg Arg Ser Ser Phe Asn Phe Gly Ser Leu Leu Ser Val Pro
                485                 490                 495

Ile Leu Ser Cys Thr Ala Leu Ala Leu Leu Leu Leu Ile Tyr Cys Cys
            500                 505                 510

Lys Arg Arg Tyr Gln Gln Thr Leu Lys Gln His Thr Lys Val Asp Pro
        515                 520                 525

Ala Phe Lys Pro Asp Leu Thr Gly Thr Ser Lys Ser Tyr Val Arg Ser
    530                 535                 540
```

-continued

```
Leu
545


<210> SEQ ID NO 21
<211> LENGTH: 18
<212> TYPE: PRT
<213> ORGANISM: Artificial Sequence
<220> FEATURE:
<223> OTHER INFORMATION: immunoglobulin E (IgE) leader

<400> SEQUENCE: 21

Met Asp Trp Thr Trp Ile Leu Phe Leu Val Ala Ala Ala Thr Arg Val
1               5                   10                  15

His Ser
```

CANINE DISTEMPER VACCINES AND METHODS OF TREATMENT USING THE SAME

CROSS REFERENCE TO RELATED APPLICATIONS

This application is the U.S. national phase application filed under 35 U.S.C. § 371 claiming benefit to International Patent Application No. PCT/US2019/058023, filed Oct. 25, 2019, which is entitled to priority of U.S. Provisional Application Ser. No. 62/751,002, filed Oct. 26, 2018, each of which is incorporated by reference herein in its entirety.

REFERENCE TO A "SEQUENCE LISTING," A TABLE, OR A COMPUTER PROGRAM LISTING APPENDIX SUBMITTED AS AN ASCII TEXT FILE

The present application hereby incorporates by reference the entire contents of the text file named "206193-0008-00US Sequence Listing_ST25.txt" in ASCII format. The text file containing the Sequence Listing of the present application was created on Apr. 21, 2021 and is 75,189 bytes in size.

TECHNICAL FIELD

Disclosed herein are compositions and methods for treating canine distemper virus (CDV) infection and in particular, vaccines that treat and provide protection against CDV.

BACKGROUND

Canine Distemper is a viral disease caused by Canine Distemper Virus (CDV), a single stranded RNA virus of the family Paramyxoviridae which is highly contagious by inhalation or by contact with infected bodily fluids. Canine distemper affects many animal families, including Canidae, Mustelidae, Ailuridae, Ursidae, and large Felidae. CDV has high morbidity, affecting multiple body systems, including the lymphoid, epithelial, and nervous tissues. Symptoms include lymphoid depletion (causing immunosuppression and leading to secondary infections), interstitial pneumonia, encephalitis with demyelination, and hyperkeratosis of the nose and foot pads. CDV presents a major threat to endangered animal populations. There have been several documented instances of free-ranging large felids succumbing to the disease, often in large numbers, after exposure to an animal with uncontrolled infection. In the context of conservation and zoos, there is a persistent concern regarding endangered animals contracting CDV infection from interloping wild dogs, raccoons, and foxes. "Exotic" animals such as large felids and mustelids are extremely susceptible to CDV infection, so much so that it is dangerous for them to receive the modified-live vaccine that is commercially available for domestic dogs. In lieu of the MLV, exotic animals in zoos often receive a canarypox vectored vaccine Purevax, which was designed for domestic ferrets. However, data has shown that large felids and red pandas often require 3 or more vaccinations with Purevax before seroconversion and this is a limited vaccine. Development of a more robust vaccine would be important for protection of potentially many species.

Accordingly, there is a need in the art for the development of compositions and methods for the prevention and/or treatment of CDV. The present invention satisfies this unmet need.

SUMMARY OF THE INVENTION

In one embodiment, the invention relates to an immunogenic composition comprising a nucleic acid molecule encoding at least one Canine Distemper Virus (CDV) antigen.

In one embodiment, the CDV antigen is a hemagglutinin glycoprotein (H) antigen, a nucleoprotein (N) antigen, a fusion glycoprotein (F) antigen, or any a combination thereof.

In one embodiment, the nucleic acid molecule encodes a peptide comprising an amino acid sequence having at least about 90% identity over an entire length of the amino acid sequence of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18 or SEQ ID NO:20. In one embodiment, the nucleic acid molecule encodes an immunogenic fragment comprising at least about 90% identity over at least 60% of the amino acid sequence of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18 or SEQ ID NO:20. In one embodiment, the nucleic acid molecule encodes the amino acid sequence of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18 or SEQ ID NO:20. In one embodiment, the nucleic acid molecule encodes an immunogenic fragment comprising at least 60% of the amino acid sequence of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18 or SEQ ID NO:20.

In one embodiment, the nucleic acid molecule is a DNA molecule or a RNA molecule.

In one embodiment, the nucleic acid molecule comprises a nucleotide sequence having at least about 90% identity over an entire length of a nucleotide sequence of SEQ ID NO:1, SEQ ID NO:2, SEQ ID NO:5, SEQ ID NO:7, SEQ ID NO:9, SEQ ID NO:11, SEQ ID NO:13, SEQ ID NO:15, SEQ ID NO:17 or SEQ ID NO:19. In one embodiment, the nucleic acid molecule comprises an immunogenic fragment of a nucleotide sequence having at least about 90% identity over at least 60% of the nucleotide sequence of SEQ ID NO:1, SEQ ID NO:2, SEQ ID NO:5, SEQ ID NO:7, SEQ ID NO:9, SEQ ID NO:11, SEQ ID NO:13, SEQ ID NO:15, SEQ ID NO:17 or SEQ ID NO:19. In one embodiment, the nucleic acid molecule comprises a nucleotide sequence of SEQ ID NO:1, SEQ ID NO:2, SEQ ID NO:5, SEQ ID NO:7, SEQ ID NO:9, SEQ ID NO:11, SEQ ID NO:13, SEQ ID NO:15, SEQ ID NO:17 or SEQ ID NO:19. In one embodiment, the nucleic acid molecule comprises an immunogenic fragment of a nucleotide sequence of SEQ ID NO:1, SEQ ID NO:2, SEQ ID NO: 5, SEQ ID NO:7, SEQ ID NO:9, SEQ ID NO:11, SEQ ID NO:13, SEQ ID NO:15, SEQ ID NO:17 or SEQ ID NO:19.

In one embodiment, the nucleic acid molecule comprises an expression vector.

In one embodiment, the nucleic acid molecule is incorporated into a viral particle.

In one embodiment, the immunogenic composition comprising a nucleic acid molecule encoding at least one CDV antigen further comprises a pharmaceutically acceptable excipient. In one embodiment, the immunogenic composition comprising a nucleic acid molecule encoding at least one CDV antigen further comprises an adjuvant.

In one embodiment, the invention relates to a nucleic acid molecule encoding at least one CDV antigen. In one embodiment, the nucleic acid molecule encodes a peptide comprising an amino acid sequence having at least about 90% identity over an entire length of the amino acid sequence of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18 or SEQ ID NO:20. In one embodiment, the nucleic acid molecule encodes an immunogenic fragment comprising at least about 90% identity over at least 60% of the amino acid sequence of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18 or SEQ ID NO:20. In one embodiment, the nucleic acid molecule encodes the amino acid sequence of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18 or SEQ ID NO:20. In one embodiment, the nucleic acid molecule encodes an immunogenic fragment comprising at least 60% of the amino acid sequence of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18 or SEQ ID NO:20.

In one embodiment, the nucleic acid molecule is a DNA molecule or an RNA molecule.

In one embodiment, the nucleic acid molecule comprises a nucleotide sequence having at least about 90% identity over an entire length of a nucleotide sequence of SEQ ID NO:1, SEQ ID NO:2, SEQ ID NO:5, SEQ ID NO:7, SEQ ID NO:9, SEQ ID NO:11, SEQ ID NO:13, SEQ ID NO:15, SEQ ID NO:17 or SEQ ID NO:19. In one embodiment, the nucleic acid molecule comprises an immunogenic fragment of a nucleotide sequence having at least about 90% identity over at least 60% of the nucleotide sequence of SEQ ID NO:1, SEQ ID NO:2, SEQ ID NO:5, SEQ ID NO:7, SEQ ID NO:9, SEQ ID NO:11, SEQ ID NO:13, SEQ ID NO:15, SEQ ID NO:17 or SEQ ID NO:19. In one embodiment, the nucleic acid molecule comprises a nucleotide sequence of SEQ ID NO:1, SEQ ID NO:2, SEQ ID NO:5, SEQ ID NO:7, SEQ ID NO:9, SEQ ID NO:11, SEQ ID NO:13, SEQ ID NO:15, SEQ ID NO:17 or SEQ ID NO:19. In one embodiment, the nucleic acid molecule comprises an immunogenic fragment of a nucleotide sequence of SEQ ID NO:1, SEQ ID NO:2, SEQ ID NO: 5, SEQ ID NO:7, SEQ ID NO:9, SEQ ID NO:11, SEQ ID NO:13, SEQ ID NO:15, SEQ ID NO:17 or SEQ ID NO:19.

In one embodiment, the encoded peptide is operably linked to at least one regulatory sequence. In one embodiment, the regulatory sequence is a start codon, an IgE leader sequence, a stop codon, or any combination thereof.

In one embodiment, the nucleic acid molecule comprises an expression vector.

In one embodiment, the nucleic acid molecule comprises a viral particle.

In one embodiment, the invention relates to an immunogenic composition comprising at least one CDV antigen. In one embodiment, the CDV antigen comprises an amino acid sequence having at least about 90% identity over an entire length of the amino acid sequence of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18 or SEQ ID NO:20. In one embodiment, the CDV antigen comprises an immunogenic fragment comprising at least about 90% identity over at least 60% of the amino acid sequence of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18 or SEQ ID NO:20. In one embodiment, the CDV antigen comprises the amino acid sequence as selected from the group consisting of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18 or SEQ ID NO:20. In one embodiment, the CDV antigen comprises an immunogenic fragment comprising at least 60% of the amino acid sequence of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18 or SEQ ID NO:20.

In one embodiment, the invention relates to a CDV antigenic peptide. In one embodiment, the peptide comprises an amino acid sequence having at least about 90% identity over an entire length of the amino acid sequence of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18 or SEQ ID NO:20. In one embodiment, the peptide comprises an immunogenic fragment comprising at least about 90% identity over at least 60% of the amino acid sequence of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18 or SEQ ID NO:20. In one embodiment, the peptide comprises the amino acid sequence selected from the group consisting of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18 or SEQ ID NO:20. In one embodiment, the peptide comprises, an immunogenic fragment comprising at least 60% of the amino acid sequence of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18 or SEQ ID NO:20.

In one embodiment, the invention relates to a method of inducing an immune response against a CDV antigen in a subject in need thereof, the method comprising administering an immunogenic composition comprising a nucleic acid molecule encoding at least one CDV antigen to the subject.

In one embodiment, the invention relates to a method of inducing an immune response against a CDV antigen in a subject in need thereof, the method comprising administering a nucleic acid molecule encoding at least one CDV antigen to the subject.

In one embodiment, the invention relates to a method of inducing an immune response against a CDV antigen in a subject in need thereof, the method comprising administering an immunogenic composition comprising at least one CDV antigen to the subject.

In one embodiment, the method of administering includes at least one of electroporation and injection.

In one embodiment, the invention relates to a method of treating or preventing CDV in subject in need thereof, the method comprising administering an immunogenic composition comprising a nucleic acid molecule encoding at least one CDV antigen to the subject.

In one embodiment, the invention relates to a method of treating or preventing CDV in subject in need thereof, the method comprising administering a nucleic acid molecule encoding at least one CDV antigen to the subject.

In one embodiment, the invention relates to a method of treating or preventing CDV in subject in need thereof, the method comprising administering an immunogenic composition comprising at least one CDV antigen to the subject.

In one embodiment, the method of administering includes at least one of electroporation and injection.

In one embodiment, the subject is a member of the Canidae, Ailuridae, Mustelidae, Procyonidae, Hyaenidae, Ursidae, Viverridae, Felidae, or Tayassuidae family.

BRIEF DESCRIPTION OF THE DRAWINGS

FIG. 1, comprising FIG. 1A depicts the DNA vaccination optimization strategy.

FIG. 1B depicts highly efficient DNA vaccine delivery by electroporation to enhance DNA vaccine elicited immune responses.

FIG. 3, comprising FIG. 3A depicts the vaccination schedule used for the experiments. FIG. 3B depicts exemplary images showing that the CDV antigens were expressed in-vitro.

DETAILED DESCRIPTION

Figure 1A:
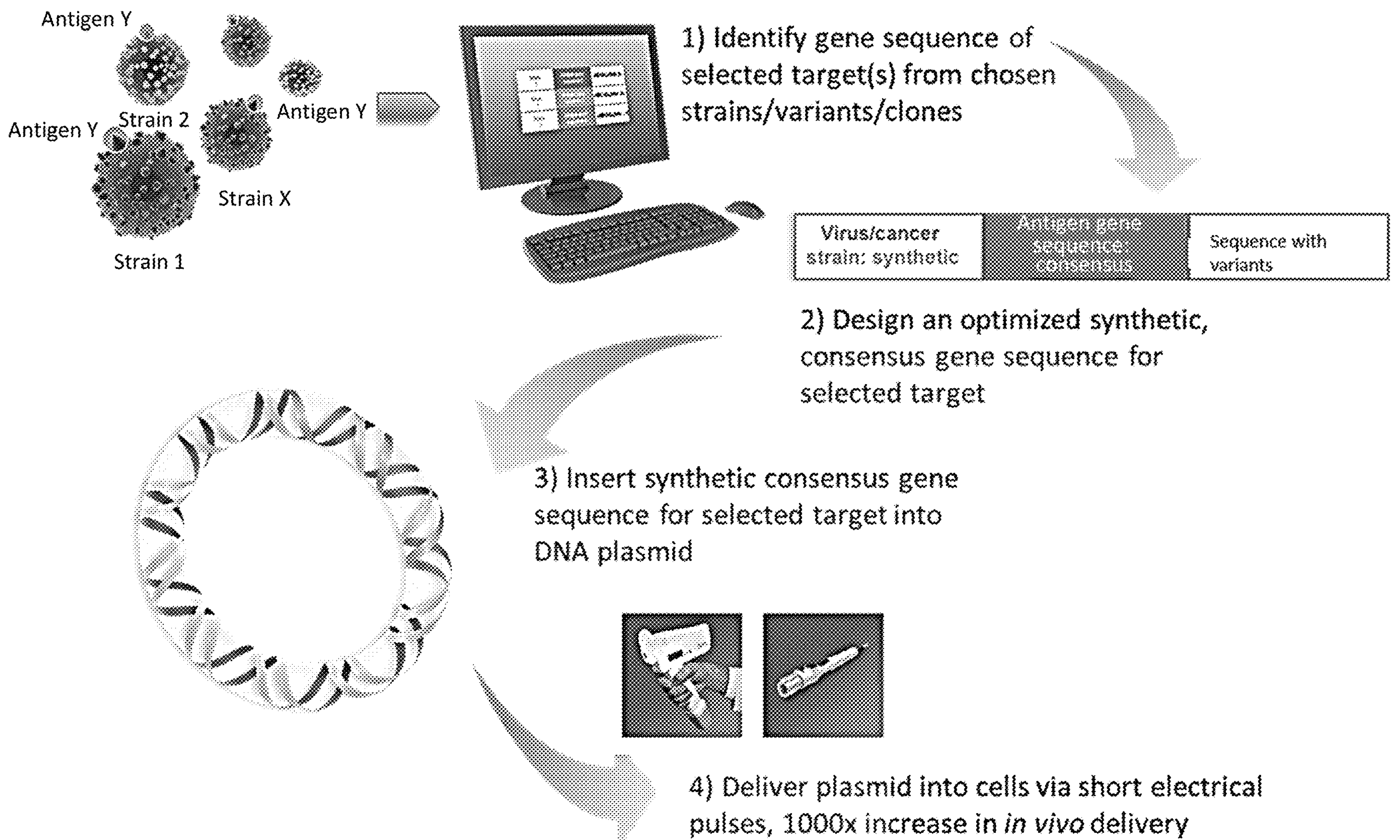
FIG. 1A and FIG. 1B, depicts schematic diagrams of the vaccine design and delivery.

The present invention is directed to a vaccine for use in treating or preventing CDV in mammals. Optimized CDV antigens and antigen consensus sequences have been designed for multiple CDV antigens to be used in the vaccine to allow for vaccine-mediated prevention and treatment of CDV. The vaccine of the invention can be used along with any combination of additional agents for the treatment or prevention of CDV in a subject in need thereof.

In one embodiment, the invention includes a nucleic acid vaccine against CDV. In one embodiment, the vaccine comprises at least one plasmid encoding one or more optimized or optimized consensus CDV antigen. In one embodiment, the CDV antigen is a hemagglutinin glycoprotein (H) antigen. In one embodiment, the CDV antigen is a nucleoprotein (N) antigen. In one embodiment, the CDV antigen is a fusion glycoprotein (F) antigen.

As a vaccine candidate, an enhanced DNA (DNA)-based platform provides many advantages in genetic optimization and delivery techniques. As such, each CDV antigen can be genetically-optimized, subcloned into modified mammalian expression vectors, and then delivered using in vivo electroporation (EP).

Vaccination in preclinical rodent studies was highly potent, as vaccination with synthetic consensus CDV antigen constructs generates robust immune responses.

In various embodiments, the invention provides coding sequences for optimized and consensus CDV antigens. Coding sequences for H, N and F antigens are provided. In some embodiments, the strategy employs coding sequences for a single CDV antigen. In some embodiments, the strategy employs coding sequences for multiple CDV antigens.

As a candidate for vaccines, DNA vaccines exhibit a multitude of advantages including rapid and inexpensive up-scale production, stability at room temperature, and ease of transport, all of which further enhance this platform from an economic and geographic perspective. Due to the synthetic nature of the plasmids, antigen sequences can be quickly and easily modified in response to newly emergent strains and/or expanded to include additional vaccine components.

Optimization of plasmid DNA vectors and their encoded antigen genes have led to increases in in vivo immunogenicity. Cellular uptake and subsequent antigen expression are substantially amplified when highly-concentrated plasmid vaccine formulations are administered with in vivo electroporation, a technology that uses brief square-wave electric pulses within the vaccination site to drive plasmids into transiently permeabilized cells. In theory, a cocktail of DNA plasmids could be assembled for directing an immune response against multiple variable antigens. Immunity can be further directed by co-delivery with plasmid molecular adjuvants encoding species-specific cytokine genes as well as 'consensus-engineering' of the antigen amino acid sequences to help bias vaccine-induced immunity towards particular strains.

1. DEFINITIONS

Unless otherwise defined, all technical and scientific terms used herein have the same meaning as commonly understood by one of ordinary skill in the art. In case of conflict, the present document, including definitions, will control. Exemplary methods and materials are described below, although methods and materials similar or equivalent to those described herein can be used in practice or testing of the present invention. All publications, patent applications, patents and other references mentioned herein are incorporated by reference in their entirety. The materials, methods, and examples disclosed herein are illustrative only and not intended to be limiting. The terminology used herein is for the purpose of describing particular embodiments only and is not intended to be limiting.

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "and" and "the" include plural references unless the context clearly dictates otherwise. The present disclosure also contemplates other embodiments "comprising," "consisting of" and "consisting essentially of" the embodiments or elements presented herein, whether explicitly set forth or not.

"Adjuvant" as used herein means any molecule added to the DNA plasmid vaccines described herein to enhance the immunogenicity of the antigens encoded by the DNA plasmids and the encoding nucleic acid sequences described hereinafter.

"Antibody" as used herein means an antibody of classes IgG, IgM, IgA, IgD or IgE, or fragments, or derivatives thereof, including Fab, F(ab')2, Fd, and single chain antibodies, diabodies, bispecific antibodies, bifunctional antibodies and derivatives thereof. The antibody can be an antibody isolated from the serum sample of mammal, a polyclonal antibody, affinity purified antibody, or mixtures thereof which exhibits sufficient binding specificity to a desired epitope or a sequence derived therefrom.

"Coding sequence" or "encoding nucleic acid" as used herein means the nucleic acids (RNA or DNA molecule) that comprise a nucleotide sequence which encodes a protein. The coding sequence can further include initiation and termination signals operably linked to regulatory elements including a promoter and polyadenylation signal capable of directing expression in the cells of an individual or mammal to which the nucleic acid is administered.

"Complement" or "complementary" as used herein means a nucleic acid can mean Watson-Crick (e.g., A-T/U and C-G) or Hoogsteen base pairing between nucleotides or nucleotide analogs of nucleic acid molecules.

"Consensus" or "consensus sequence" as used herein means a polypeptide sequence based on analysis of an alignment of multiple sequences for the same gene from different organisms. Nucleic acid sequences that encode a consensus polypeptide sequence can be prepared. Vaccines comprising proteins that comprise consensus sequences and/or nucleic acid molecules that encode such proteins can be used to induce broad immunity against an antigen. "Constant current" as used herein to define a current that is received or experienced by a tissue, or cells defining said tissue, over the duration of an electrical pulse delivered to same tissue. The electrical pulse is delivered from the electroporation devices described herein. This current remains at a constant amperage in said tissue over the life of an electrical pulse because the electroporation device provided herein has a feedback element, preferably having instantaneous feedback. The feedback element can measure the resistance of the tissue (or cells) throughout the duration of the pulse and cause the electroporation device to alter its electrical energy output (e.g., increase voltage) so current in same tissue remains constant throughout the electrical pulse (on the order of microseconds), and from pulse to pulse. In some embodiments, the feedback element comprises a controller.

"Current feedback" or "feedback" as used herein may be used interchangeably and may mean the active response of the provided electroporation devices, which comprises measuring the current in tissue between electrodes and altering the energy output delivered by the EP device accordingly in order to maintain the current at a constant level. This constant level is preset by a user prior to initiation of a pulse sequence or electrical treatment. The feedback may be accomplished by the electroporation component, e.g., controller, of the electroporation device, as the electrical circuit therein is able to continuously monitor the current in tissue between electrodes and compare that monitored current (or current within tissue) to a preset current and continuously make energy-output adjustments to maintain the monitored current at preset levels. The feedback loop may be instantaneous as it is an analog closed-loop feedback.

"Decentralized current" as used herein may mean the pattern of electrical currents delivered from the various needle electrode arrays of the electroporation devices described herein, wherein the patterns minimize, or preferably eliminate, the occurrence of electroporation related heat stress on any area of tissue being electroporated.

"Electroporation," "electro-permeabilization," or "electro-kinetic enhancement" ("EP") as used interchangeably herein means the use of a transmembrane electric field pulse to induce microscopic pathways (pores) in a bio-membrane; their presence allows biomolecules such as plasmids, oligonucleotides, siRNA, drugs, ions, and water to pass from one side of the cellular membrane to the other.

"Fragment" or "immunogenic fragment" as used herein with respect to nucleic acid sequences means a nucleic acid sequence or a portion thereof, that encodes a polypeptide capable of eliciting an immune response in a mammal. The fragments can be DNA fragments selected from at least one of the various nucleotide sequences that encode protein fragments set forth below. Fragments can comprise at least 10%, at least 20%, at least 30%, at least 40%, at least 50%, at least 60%, at least 70%, at least 80%, at least 90%, or at least 95% of one or more of the nucleic acid sequences set forth below. In some embodiments, fragments can comprise at least 20 nucleotides or more, at least 30 nucleotides or more, at least 40 nucleotides or more, at least 50 nucleotides or more, at least 60 nucleotides or more, at least 70 nucleotides or more, at least 80 nucleotides or more, at least 90 nucleotides or more, at least 100 nucleotides or more, at least 150 nucleotides or more, at least 200 nucleotides or more, at least 250 nucleotides or more, at least 300 nucleotides or more, at least 350 nucleotides or more, at least 400 nucleotides or more, at least 450 nucleotides or more, at least 500 nucleotides or more, at least 550 nucleotides or more, at least 600 nucleotides or more, at least 650 nucleotides or more, at least 700 nucleotides or more, at least 750 nucleotides or more, at least 800 nucleotides or more, at least 850 nucleotides or more, at least 900 nucleotides or more, at least 950 nucleotides or more, or at least 1000 nucleotides or more of at least one of the nucleic acid sequences set forth below.

"Fragment" or "immunogenic fragment" with respect to polypeptide sequences means a polypeptide capable of eliciting an immune response in a mammal. The fragments can be polypeptide fragments selected from at least one of the various amino acids sequences below. Fragments of proteins can comprise at least 10%, at least 20%, at least 30%, at least 40%, at least 50%, at least 60%, at least 70%, at least 80%, at least 90% or at least 95% of a protein. In some embodiments, fragments of proteins can comprise at least 20 amino acids or more, at least 30 amino acids or more, at least 40 amino acids or more, at least 50 amino acids or more, at least 60 amino acids or more, at least 70 amino acids or more, at least 80 amino acids or more, at least 90 amino acids or more, at least 100 amino acids or more, at least 110 amino acids or more, at least 120 amino acids or more, at least 130 amino acids or more, at least 140 amino acids or more, at least 150 amino acids or more, at least 160 amino acids or more, at least 170 amino acids or more, at least 180 amino acids or more of a polypeptide sequence disclosed herein.

"Fragment" or "immunogenic fragment" may mean a percentage of a full length polypeptide sequence or nucleotide sequence. Fragments may comprise 20% or more, 25% or more, 30% or more, 35% or more, 40% or more, 45% or more, 50% or more, 55% or more, 60% or more, 65% or more, 70% or more, 75% or more, 80% or more, 85% or more, 90% or more, 91% or more, 92% or more, 93% or more, 94% or more, 95% or more, 96% or more, 97% or more, 98% or more, 99% or more percent of the full length of the parental nucleotide sequence or amino acid sequence or variant thereof.

As used herein, the term "genetic construct" refers to the DNA or RNA molecules that comprise a nucleotide sequence which encodes a protein. The coding sequence includes initiation and termination signals operably linked to regulatory elements including a promoter and polyadenylation signal capable of directing expression in the cells of the individual to whom the nucleic acid molecule is administered. As used herein, the term "expressible form" refers to gene constructs that contain the necessary regulatory elements operably linked to a coding sequence that encodes a protein such that when present in the cell of the individual, the coding sequence will be expressed.

The term "homology," as used herein, refers to a degree of complementarity. There can be partial homology or complete homology (i.e., identity). A partially complementary sequence that at least partially inhibits a completely complementary sequence from hybridizing to a target nucleic acid is referred to using the functional term "substantially homologous." When used in reference to a double-stranded nucleic acid sequence such as a cDNA or genomic clone, the term "substantially homologous," as used herein, refers to a probe that can hybridize to a strand of the double-stranded nucleic acid sequence under conditions of low stringency. When used in reference to a single-stranded nucleic acid sequence, the term "substantially homologous," as used herein, refers to a probe that can hybridize to (i.e., is the complement of) the single-stranded nucleic acid template sequence under conditions of low stringency.

"Identical" or "identity" as used herein in the context of two or more nucleic acids or polypeptide sequences means that the sequences have a specified percentage of residues that are the same over a specified region. The percentage can be calculated by optimally aligning the two sequences, comparing the two sequences over the specified region, determining the number of positions at which the identical residue occurs in both sequences to yield the number of matched positions, dividing the number of matched positions by the total number of positions in the specified region, and multiplying the result by 100 to yield the percentage of sequence identity. In cases where the two sequences are of different lengths or the alignment produces one or more staggered ends and the specified region of comparison includes only a single sequence, the residues of single sequence are included in the denominator but not the numerator of the calculation. When comparing DNA and RNA, thymine (T) and uracil (U) can be considered equivalent. Identity can be performed manually or by using a computer sequence algorithm such as BLAST or BLAST 2.0.

"Impedance" as used herein may be used when discussing the feedback mechanism and can be converted to a current value according to Ohm's law, thus enabling comparisons with the preset current.

"Immune response" as used herein means the activation of a host's immune system, e.g., that of a mammal, in response to the introduction of antigen. The immune response can be in the form of a cellular or humoral response, or both.

"Nucleic acid" or "oligonucleotide" or "polynucleotide" as used herein means at least two nucleotides covalently linked together. The depiction of a single strand also defines the sequence of the complementary strand. Thus, a nucleic acid also encompasses the complementary strand of a depicted single strand. Many variants of a nucleic acid can be used for the same purpose as a given nucleic acid. Thus, a nucleic acid also encompasses substantially identical nucleic acids and complements thereof. A single strand provides a probe that can hybridize to a target sequence under stringent hybridization conditions. Thus, a nucleic acid also encompasses a probe that hybridizes under stringent hybridization conditions.

Nucleic acids can be single stranded or double stranded, or can contain portions of both double stranded and single stranded sequence. The nucleic acid can be DNA, both genomic and cDNA, RNA, or a hybrid, where the nucleic acid can contain combinations of deoxyribo- and ribonucleotides, and combinations of bases including uracil, adenine, thymine, cytosine, guanine, inosine, xanthine hypoxanthine, isocytosine and isoguanine. Nucleic acids can be obtained by chemical synthesis methods or by recombinant methods.

"Operably linked" as used herein means that expression of a gene is under the control of a promoter with which it is spatially connected. A promoter can be positioned 5' (upstream) or 3' (downstream) of a gene under its control. The distance between the promoter and a gene can be approximately the same as the distance between that promoter and the gene it controls in the gene from which the promoter is derived. As is known in the art, variation in this distance can be accommodated without loss of promoter function.

A "peptide," "protein," or "polypeptide" as used herein can mean a linked sequence of amino acids and can be natural, synthetic, or a modification or combination of natural and synthetic.

"Promoter" as used herein means a synthetic or naturally-derived molecule which is capable of conferring, activating or enhancing expression of a nucleic acid in a cell. A promoter can comprise one or more specific transcriptional regulatory sequences to further enhance expression and/or to alter the spatial expression and/or temporal expression of same. A promoter can also comprise distal enhancer or repressor elements, which can be located as much as several thousand base pairs from the start site of transcription. A promoter can be derived from sources including viral, bacterial, fungal, plants, insects, and animals. A promoter can regulate the expression of a gene component constitutively, or differentially with respect to the cell, tissue or organ in which expression occurs or, with respect to the developmental stage at which expression occurs, or in response to external stimuli such as physiological stresses, pathogens, metal ions, or inducing agents. Representative examples of promoters include the bacteriophage T7 promoter, bacteriophage T3 promoter, SP6 promoter, lac operator-promoter, tac promoter, SV40 late promoter, SV40 early promoter, RSV-LTR promoter, CMV IE promoter, SV40 early promoter or SV40 late promoter and the CMV IE promoter.

"Signal peptide" and "leader sequence" are used interchangeably herein and refer to an amino acid sequence that can be linked at the amino terminus of a protein set forth herein. Signal peptides/leader sequences typically direct localization of a protein. Signal peptides/leader sequences used herein may facilitate secretion of the protein from the cell in which it is produced. Signal peptides/leader sequences are often cleaved from the remainder of the protein, often referred to as the mature protein, upon secretion from the cell. Signal peptides/leader sequences are linked at the amino terminus (i.e., N terminus) of the protein.

"Stringent hybridization conditions" as used herein means conditions under which a first nucleic acid sequence (e.g., probe) will hybridize to a second nucleic acid sequence (e.g., target), such as in a complex mixture of nucleic acids. Stringent conditions are sequence-dependent and will be different in different circumstances. Stringent conditions can be selected to be about 5-10° C. lower than the thermal melting point (Tm) for the specific sequence at a defined ionic strength pH. The Tm can be the temperature (under defined ionic strength, pH, and nucleic concentration) at which 50% of the probes complementary to the target hybridize to the target sequence at equilibrium (as the target sequences are present in excess, at Tm, 50% of the probes are occupied at equilibrium). Stringent conditions can be those in which the salt concentration is less than about 1.0 M sodium ion, such as about 0.01-1.0 M sodium ion concentration (or other salts) at pH 7.0 to 8.3 and the temperature is at least about 30° C. for short probes (e.g., about 10-50 nucleotides) and at least about 60° C. for long probes (e.g., greater than about 50 nucleotides). Stringent conditions can also be achieved with the addition of destabilizing agents such as formamide. For selective or specific hybridization, a positive signal can be at least 2 to 10 times background hybridization. Exemplary stringent hybridization conditions include the following: 50% formamide, 5×SSC, and 1% SDS, incubating at 42° C., or, 5×SSC, 1% SDS, incubating at 65° C., with wash in 0.2×SSC, and 0.1% SDS at 65° C.

"Subject" as used herein can mean a mammal that is capable of being immunized with the vaccines described herein. The mammal can be, for example, a human, chimpanzee, dog, cat, horse, cow, mouse, or rat. In some embodiments, the subject may be a species in a family in the order Carnivora (e.g. Canidae, Ailuridae, Mustelidae, Procyonidae, Hyaenidae, Ursidae, Viverridae, and Felidae), a tayassuidae (e.g., a peccary or javelina), a marine mammal, or a mammal that is susceptible to CDV.

"Substantially complementary" as used herein means that a first sequence is at least 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98% or 99% identical to the complement of a second sequence over a region of 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100, 180, 270, 360, 450, 540, or more nucleotides or amino acids, or that the two sequences hybridize under stringent hybridization conditions.

"Substantially identical" as used herein means that a first and second sequence are at least 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98% or 99% identical over a region of 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100, 180, 270, 360, 450, 540 or more nucleotides or amino acids, or with respect to nucleic acids, if the first sequence is substantially complementary to the complement of the second sequence.

"Treatment" or "treating" as used herein can mean protecting an animal from a disease through means of preventing, suppressing, repressing, or completely eliminating the disease. Preventing the disease involves administering a vaccine of the present invention to an animal prior to onset of the disease. Suppressing the disease involves administering a vaccine of the present invention to an animal after induction of the disease but before its clinical appearance. Repressing the disease involves administering a vaccine of the present invention to an animal after clinical appearance of the disease.

"Variant" used herein with respect to a nucleic acid means (i) a portion or fragment of a referenced nucleotide sequence; (ii) the complement of a referenced nucleotide sequence or portion thereof; (iii) a nucleic acid that is substantially identical to a referenced nucleic acid or the complement thereof; or (iv) a nucleic acid that hybridizes under stringent conditions to the referenced nucleic acid, complement thereof, or a sequence substantially identical thereto.

"Variant" with respect to a peptide or polypeptide refers to a peptide or polypeptide that differs in amino acid sequence by the insertion, deletion, or conservative substitution of amino acids, but retain at least one biological activity. Variant can also mean a protein with an amino acid sequence that is substantially identical to a referenced protein with an amino acid sequence that retains at least one biological activity. A conservative substitution of an amino acid, i.e., replacing an amino acid with a different amino acid of similar properties (e.g., hydrophilicity, degree and distribution of charged regions) is recognized in the art as typically involving a minor change. These minor changes can be identified, in part, by considering the hydropathic index of amino acids, as understood in the art, for example, see Kyte et al., J. Mol. Biol. 157:105-132 (1982). The hydropathic index of an amino acid is based on a consideration of its hydrophobicity and charge. It is known in the art that amino acids of similar hydropathic indexes can be substituted and still retain protein function. In one aspect, amino acids having hydropathic indexes of ±2 are substituted. The hydrophilicity of amino acids can also be used to reveal substitutions that would result in proteins retaining biological function. A consideration of the hydrophilicity of amino acids in the context of a peptide permits calculation of the greatest local average hydrophilicity of that peptide, a useful measure that has been reported to correlate well with antigenicity and immunogenicity. U.S. Pat. No. 4,554,101, incorporated fully herein by reference. Substitution of amino acids having similar hydrophilicity values can result in peptides retaining biological activity, for example immunogenicity, as is understood in the art. Substitutions can be performed with amino acids having hydrophilicity values within ±2 of each other. Both the hyrophobicity index and the hydrophilicity value of amino acids are influenced by the particular side chain of that amino acid. Consistent with that observation, amino acid substitutions that are compatible with biological function are understood to depend on the relative similarity of the amino acids, and particularly the side chains of those amino acids, as revealed by the hydrophobicity, hydrophilicity, charge, size, and other properties.

A variant may be a nucleic acid sequence that is substantially identical over the full-length of the full gene sequence or a fragment thereof. The nucleic acid sequence may be 80%, 81%, 82%, 83%, 84%, 85%, 86%, 87%, 88%, 89%, 90%, 91%, 92%, 93%, 94%, 95%, 96%, 97%, 98%, 99%, or 100% identical over the full-length of the gene sequence or a fragment thereof. A variant may be an amino acid sequence that is substantially identical over the full-length of the amino acid sequence or fragment thereof. The amino acid sequence may be 80%, 81%, 82%, 83%, 84%, 85%, 86%, 87%, 88%, 89%, 90%, 91%, 92%, 93%, 94%, 95%, 96%, 97%, 98%, 99%, or 100% identical over the full-length of the amino acid sequence or a fragment thereof.

"Vector" as used herein means a nucleic acid sequence containing an origin of replication. A vector can be a viral vector, bacteriophage, bacterial artificial chromosome or yeast artificial chromosome. A vector can be a DNA or RNA vector. A vector can be a self-replicating extrachromosomal vector, and for example, may be a DNA plasmid. The vector can contain or include one or more heterologous nucleic acid sequences.

For recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the numbers 6.0, 6.1, 6.2, 6.3, 6.4, 6.5, 6.6, 6.7, 6.8, 6.9, and 7.0 are explicitly contemplated.

2. VACCINE

The invention provides an optimized sequence encoding a CDV antigen. In one embodiment, the CDV antigen encoded by the optimized sequence is capable of eliciting an immune response in a mammal. In one embodiment, the CDV antigen encoded by the optimized sequence can comprise an epitope(s) that makes it particularly effective as an immunogen against which an immune response can be induced.

In one embodiment, the optimized sequence can be a consensus sequence derived from two or more CDV antigens. The optimized consensus sequence can comprise a consensus sequence and/or modification(s) for improved expression. Modification can include codon optimization, RNA optimization, addition of a kozak sequence for increased translation initiation, and/or the addition of an immunoglobulin leader sequence to increase immunogenicity. The CDV antigen encoded by the optimized sequence can comprise a signal peptide such as an immunoglobulin signal peptide, for example, but not limited to, an immunoglobulin E (IgE) or immunoglobulin (IgG) signal peptide. In some embodiments, the antigen encoded by the optimized sequence can comprise a hemagglutinin (HA) tag. The antigen encoded by the optimized sequence can be designed to elicit stronger cellular and/or humoral immune responses than a corresponding non-optimized antigen.

Provided herein are CDV antigens that can be used to induce immunity against CDV in subjects susceptible to CDV infection. In one embodiment, the present invention provides an immunogenic composition comprising one or more nucleic acid molecules that are capable of generating in a mammal an immune response against a CDV antigen. The present invention also provides isolated nucleic acid molecules that are capable of generating in a mammal an immune response against a CDV antigen. In one embodiment, the nucleic acid molecule comprises an optimized nucleotide sequence encoding the CDV antigen. In one embodiment, the CDV antigen is a consensus CDV antigen.

In some embodiments, the induced or elicited immune response can be a cellular, humoral, or both cellular and humoral immune response. In some embodiments, the induced or elicited cellular immune response can include induction or secretion of interferon-gamma (IFN-γ) and/or tumor necrosis factor alpha (TNF-α).

The vaccine can increase a cellular immune response in a subject administered the vaccine by about 2-fold to about 6000-fold, about 3-fold to about 6000-fold, about 4-fold to about 6000-fold, about 5-fold to about 6000-fold, about 6-fold to about 6000-fold, about 7-fold to about 6000-fold, about 8-fold to about 6000-fold, about 9-fold to about 6000-fold, about 10-fold to about 6000-fold, about 15-fold to about 6000-fold, about 10-fold to about 6000-fold, about 25-fold to about 6000-fold, about 30-fold to about 6000-fold, about 35-fold to about 6000-fold, about 40-fold to about 6000-fold, about 45-fold to about 6000-fold, about 50-fold to about 6000-fold, about 2-fold to about 5500-fold, about 2-fold to about 5000-fold, about 2-fold to about 4500-fold, about 100-fold to about 6000-fold, about 150-fold to about 6000-fold, about 200-fold to about 6000-fold, about 250-fold to about 6000-fold, or about 300-fold to about 6000-fold as compared to a cellular immune response in a subject not administered the vaccine. In some embodiments the vaccine can increase the cellular immune response in the subject administered the vaccine by about 2-fold, 3-fold, 4-fold, 5-fold, 6-fold, 7-fold, 8-fold, 9-fold, 10-fold, 15-fold, 20-fold, 25-fold, 30-fold, 35-fold, 40-fold, 45-fold, 50-fold, 100-fold, 150-fold, 200-fold, 250-fold, 300-fold, 350-fold, 400-fold, 450-fold, 500-fold, 550-fold, 600-fold, 650-fold, 700-fold, 750-fold, 800-fold, 850-fold, 900-fold, 950-fold, 1000-fold, 1100-fold, 1200-fold, 1300-fold, 1400-fold, 1500-fold, 1600-fold, 1700-fold, 1800-fold, 1900-fold, 2000-fold, 2100-fold, 2200-fold, 2300-fold, 2400-fold, 2500-fold, 2600-fold, 2700-fold, 2800-fold, 2900-fold, 3000-fold, 3100-fold, 3200-fold, 3300-fold, 3400-fold, 3500-fold, 3600-fold, 3700-fold, 3800-fold, 3900-fold, 4000-fold, 4100-fold, 4200-fold, 4300-fold, 4400-fold, 4500-fold, 4600-fold, 4700-fold, 4800-fold, 4900-fold, 5000-fold, 5100-fold, 5200-fold, 5300-fold, 5400-fold, 5500-fold, 5600-fold, 5700-fold, 5800-fold, 5900-fold, or 6000-fold as compared to the cellular immune response in the subject not administered the vaccine.

The vaccine can increase interferon gamma (IFN-γ) levels in a subject administered the vaccine by about 2-fold to about 6000-fold, about 3-fold to about 6000-fold, about 4-fold to about 6000-fold, about 5-fold to about 6000-fold, about 6-fold to about 6000-fold, about 7-fold to about 6000-fold, about 8-fold to about 6000-fold, about 9-fold to about 6000-fold, about 10-fold to about 6000-fold, about 15-fold to about 6000-fold, about 10-fold to about 6000-fold, about 25-fold to about 6000-fold, about 30-fold to about 6000-fold, about 35-fold to about 6000-fold, about 40-fold to about 6000-fold, about 45-fold to about 6000-fold, 50-fold to about 6000-fold, about 2-fold to about 5500-fold, about 2-fold to about 5000-fold, about 2-fold to about 4500-fold, about 100-fold to about 6000-fold, about 150-fold to about 6000-fold, about 200-fold to about 6000-fold, about 250-fold to about 6000-fold, or about 300-fold to about 6000-fold as compared to IFN-γ levels in a subject not administered the vaccine. In some embodiments the vaccine can increase IFN-γ levels in the subject administered the vaccine by about 2-fold, 3-fold, 4-fold, 5-fold, 6-fold, 7-fold, 8-fold, 9-fold, 10-fold, 15-fold, 20-fold, 25-fold, 30-fold, 35-fold, 40-fold, 45-fold, 50-fold, 100-fold, 150-fold, 200-fold, 250-fold, 300-fold, 350-fold, 400-fold, 450-fold, 500-fold, 550-fold, 600-fold, 650-fold, 700-fold, 750-fold, 800-fold, 850-fold, 900-fold, 950-fold, 1000-fold, 1100-fold, 1200-fold, 1300-fold, 1400-fold, 1500-fold, 1600-fold, 1700-fold, 1800-fold, 1900-fold, 2000-fold, 2100-fold, 2200-fold, 2300-fold, 2400-fold, 2500-fold, 2600-fold, 2700-fold, 2800-fold, 2900-fold, 3000-fold, 3100-fold, 3200-fold, 3300-fold, 3400-fold, 3500-fold, 3600-fold, 3700-fold, 3800-fold, 3900-fold, 4000-fold, 4100-fold, 4200-fold, 4300-fold, 4400-fold, 4500-fold, 4600-fold, 4700-fold, 4800-fold, 4900-fold, 5000-fold, 5100-fold, 5200-fold, 5300-fold, 5400-fold, 5500-fold, 5600-fold, 5700-fold, 5800-fold, 5900-fold, or 6000-fold as compared to IFN-γ levels in the subject not administered the vaccine.

The vaccine can be a DNA vaccine. DNA vaccines are disclosed in U.S. Pat. Nos. 5,593,972, 5,739,118, 5,817,637, 5,830,876, 5,962,428, 5,981,505, 5,580,859, 5,703,055, and 5,676,594, which are incorporated herein fully by reference. The DNA vaccine can further comprise elements or reagents that inhibit it from integrating into the chromosome.

The vaccine can be an RNA of the one or more CDV antigens. The RNA vaccine can be introduced into the cell.

The vaccine can be an attenuated live vaccine, a vaccine using recombinant vectors to deliver antigen, subunit vaccines, and glycoprotein vaccines, for example, but not limited, the vaccines described in U.S. Pat. Nos. 4,510,245; 4,797,368; 4,722,848; 4,790,987; 4,920,209; 5,017,487; 5,077,044; 5,110,587; 5,112,749; 5,174,993; 5,223,424; 5,225,336; 5,240,703; 5,242,829; 5,294,441; 5,294,548; 5,310,668; 5,387,744; 5,389,368; 5,424,065; 5,451,499; 5,453,364; 5,462,734; 5,470,734; 5,474,935; 5,482,713; 5,591,439; 5,643,579; 5,650,309; 5,698,202; 5,955,088; 6,034,298; 6,042,836; 6,156,319 and 6,589,529, which are each incorporated herein by reference.

The vaccine of the present invention can have features required of effective vaccines such as being safe so that the vaccine itself does not cause illness or death; being protective against illness; inducing neutralizing antibody; inducing protective T cell responses; and providing ease of administration, few side effects, biological stability, and low cost per dose. The vaccine can accomplish some or all of these features by comprising the CDV antigen of the invention.

The synthetic consensus antigen can be a nucleic acid sequence, an amino acid sequence, or a combination thereof. The at least one CDV antigen can be a nucleic acid sequence, an amino acid sequence, or a combination thereof. The nucleic acid sequence can be DNA, RNA, cDNA, a variant thereof, a fragment thereof, or a combination thereof. The nucleic acid sequence can also include additional sequences that encode linker or tag sequences that are linked to the antigen by a peptide bond. The amino acid sequence can be a protein, a peptide, a variant thereof, a fragment thereof, or a combination thereof. The CDV antigen can be a recombinant CDV antigen.

One manner for designing the nucleic acid and its encoded amino acid sequence of the CDV antigen is by creating an optimized consensus CDV antigen that has at least 85% and up to 99% amino acid sequence identity to its corresponding native CDV antigen; at least 90% and up to 98% sequence identity; at least 93% and up to 98% sequence identity; or at least 95% and up to 98% sequence identity. In some embodiments, the optimized consensus CDV antigen has 95%, 96%, 97%, 98%, or 99% amino acid sequence identity to its corresponding native CDV antigen. The native CDV antigen is the antigen normally associated with CDV. Depending upon the CDV antigen, the consensus sequence of the CDV antigen can be across viral strains or serotypes.

a. CDV Antigen

The vaccine of the present invention can comprise at least one synthetic consensus CDV antigen, a fragment thereof, or a variant thereof.

The nucleic acid sequence encoding the CDV antigen or consensus CDV antigen can be optimized with regards to codon usage and corresponding RNA transcripts. The nucleic acid encoding the CDV antigen or consensus CDV antigen can be codon and RNA optimized for expression in mammals. In some embodiments, the nucleic acid sequence encoding the CDV antigen or consensus CDV antigen can include a Kozak sequence to increase the efficiency of translation. The nucleic acid encoding the CDV antigen or consensus CDV antigen can include or be operably linked to one or multiple stop codons (e.g., encoded by a sequence such as TGA or TGATAA) to increase the efficiency of translation termination.

The nucleic acid encoding the CDV antigen or consensus CDV antigen can also encode an immunoglobulin E (IgE) leader sequence. The nucleic acid encoding the CDV antigen or consensus CDV antigen can further encode the IgE leader sequence such that the amino acid sequence of the IgE leader sequence is linked to the amino acid sequence of the CDV antigen or consensus CDV antigen by a peptide bond, respectively. In some embodiments, the nucleic acid encoding the CDV antigen or consensus CDV antigen is free of or does not contain a nucleotide sequence encoding the IgE leader sequence.

Consensus amino acid sequences for CDV antigens include SEQ ID NO:2, SEQ ID NO:4, SEQ ID NO:8, SEQ ID NO:10, SEQ ID NO:14, SEQ ID NO:16, SEQ ID NO:18 and variants thereof and fragments of SEQ ID NO:2, SEQ ID NO:4, SEQ ID NO:8, SEQ ID NO:10, SEQ ID NO:14, SEQ ID NO:16, SEQ ID NO:18 and variants thereof Δn exemplary amino acid sequence of a synthetic consensus H antigen is provided as SEQ ID NO:2. An exemplary amino acid sequence of a synthetic consensus N antigen is provided as SEQ ID NO: 8. An exemplary amino acid sequence of a synthetic consensus F antigen is provided as SEQ ID NO:14.

Amino acid sequences for optimized CDV antigens operably linked to IgE leader sequences include SEQ ID NO:6, SEQ ID NO:12, and SEQ ID NO:20 and variants thereof. An exemplary amino acid sequence of an optimized H antigen is provided as SEQ ID NO:6. An exemplary amino acid sequence of an optimized N antigen is provided as SEQ ID NO:12. An exemplary amino acid sequence of an optimized F antigen is provided as SEQ ID NO:20.

In one embodiment, the invention provides compositions comprising a nucleic acid molecule comprising a nucleotide sequence that encodes a synthetic consensus CDV antigen. In one embodiment, a nucleotide sequence which encodes a synthetic consensus H antigen is provided as SEQ ID NO:1, which encodes SEQ ID NO:2. In one embodiment, a nucleotide sequence which encodes a synthetic consensus N antigen is provided as SEQ ID NO:7, which encodes SEQ ID NO:8. In one embodiment, a nucleotide sequence which encodes a synthetic consensus F antigen is provided as SEQ ID NO:13, which encodes SEQ ID NO:14.

In various embodiments, the invention provides compositions comprising a combination of two or more synthetic consensus CDV antigens. In one embodiment, the composition comprises at least two of a synthetic consensus H antigen, a synthetic consensus N antigen and a synthetic consensus F antigen. In one embodiment, the composition comprises each of a synthetic consensus H antigen, a synthetic consensus N antigen and a synthetic consensus F antigen. The compositions may comprise a plurality of copies of a single nucleic acid molecule such a single plasmid, or a plurality of copies of two or more different nucleic acid molecules such as two or more different plasmids.

Compositions may comprise a single nucleic acid molecule, such as a plasmid, that contains coding sequence for multiple consensus CDV antigens. In one embodiment, the compositions may comprise a single nucleic acid molecule comprising nucleotide sequences that encode at least two of a synthetic consensus H antigen, a synthetic consensus N antigen and a synthetic consensus F antigen. In one embodiment, each coding sequence for each consensus CDV antigen is on a separate plasmid.

Accordingly, compositions that comprise one or more nucleotide sequence that encode multiple consensus CDV antigens may be on a single plasmid. In one embodiment, a composition comprises a single plasmid that encodes at least two of a synthetic consensus H antigen, a synthetic consensus N antigen and a synthetic consensus F antigen under a single promoter. In such an embodiment, the sequence that encodes each of the at least two CDV antigens may be linked by a fusion peptide sequence, for example a furin cleavage sequence.

In one embodiment, an optimized consensus encoded CDV antigen is operably linked to one or more regulatory elements. In one embodiment, a regulatory element is a leader sequence. In one embodiment, the leader sequence is an IgE leader sequence. In one embodiment, the IgE leader sequence has an amino acid sequence as set forth in SEQ ID NO:21. Therefore in one embodiment, the invention relates to an amino acid sequence as set forth in SEQ ID NO:2, SEQ ID NO:8 or SEQ ID NO:14 operably linked to an amino acid sequence as set forth in SEQ ID NO:21. In one embodiment, the invention relates to a nucleotide sequence encoding an amino acid sequence as set forth in SEQ ID NO:2, SEQ ID NO: 8 or SEQ ID NO:14 operably linked to a nucleotide sequence encoding an amino acid sequence as set forth in SEQ ID NO:21.

In one embodiment, a regulatory element is a start codon. Therefore, in one embodiment, the invention relates to a nucleotide sequence as set forth in SEQ ID NO:1, SEQ ID NO:5 or SEQ ID NO:9, or a fragment or homolog thereof, operably linked to a nucleotide sequence comprising a start codon at the 5' terminus. In one embodiment, the invention relates to an amino acid sequence as set forth in SEQ ID NO:2, SEQ ID NO:6 or SEQ ID NO:10 or a fragment or homolog thereof, operably linked to an amino acid encoded by a start codon (e.g., a Methionine) at the N-terminus.

In one embodiment, a regulatory element is at least one stop codon. Therefore, in one embodiment, the invention relates to a nucleotide sequence as set forth in SEQ ID NO:1, SEQ ID NO:5 or SEQ ID NO:9, or a fragment or homolog thereof, operably linked to a nucleotide sequence comprising at least one stop codon at the 3' terminus. In one embodiment, the nucleotide sequence is operably linked to two stop codons to increase the efficiency of translational termination.

In one embodiment, the invention provides compositions comprising a nucleic acid molecule comprising a nucleotide sequence that encodes a synthetic consensus CDV antigen operably linked to a signal peptide or leader sequence. In one embodiment, a nucleotide sequence which encodes a synthetic consensus H antigen operably linked to an IgE leader sequence is provided as SEQ ID NO:3, which encodes SEQ ID NO:4. In one embodiment, a nucleotide sequence which encodes a synthetic consensus N antigen operably linked to an IgE leader sequence is provided as SEQ ID NO:9, which encodes SEQ ID NO:10. In one embodiment, a nucleotide sequence which encodes a synthetic consensus F antigen operably linked to an endo leader sequence is provided as SEQ ID NO:15, which encodes SEQ ID NO:16. In one embodiment, a nucleotide sequence which encodes a synthetic consensus F antigen operably linked to an IgE leader sequence is provided as SEQ ID NO:17, which encodes SEQ ID NO:18.

In one embodiment, the invention provides compositions comprising a nucleic acid molecule comprising a nucleotide sequence that encodes an optimized CDV antigen, wherein the optimization includes a signal peptide or leader sequence at the N terminus of the antigen. In one embodiment, a nucleotide sequence which encodes an optimized H antigen operably linked to an IgE leader sequence is provided as SEQ ID NO:5, which encodes SEQ ID NO:6. In one embodiment, a nucleotide sequence which encodes an optimized N antigen operably linked to an IgE leader sequence is provided as SEQ ID NO:11, which encodes SEQ ID NO:12. In one embodiment, a nucleotide sequence which encodes an optimized F antigen operably linked to an IgE leader sequence is provided as SEQ ID NO:19, which encodes SEQ ID NO:20.

| SEQ ID NO: | Sequence Type | Description |
|---|---|---|
| 1 | Nucleotide | Consensus H |
| 2 | Amino acid | Consensus H |
| 3 | Nucleotide | Consensus H operably linked to IgE leader |
| 4 | Amino acid | Consensus H operably linked to IgE leader |
| 5 | Nucleotide | Optimized H operably linked to IgE leader |
| 6 | Amino acid | Optimized H operably linked to IgE leader |
| 7 | Nucleotide | Consensus N |
| 8 | Amino acid | Consensus N |
| 9 | Nucleotide | Consensus N operably linked to IgE leader |
| 10 | Amino acid | Consensus N operably linked to IgE leader |
| 11 | Nucleotide | Optimized N operably linked to IgE leader |
| 12 | Amino acid | Optimized N operably linked to IgE leader |
| 13 | Nucleotide | Consensus F |
| 14 | Amino acid | Consensus F |
| 15 | Nucleotide | Consensus F operably linked to Endo leader |
| 16 | Amino acid | Consensus F operably linked to Endo leader |
| 17 | Nucleotide | Consensus F operably linked to IgE leader |
| 18 | Amino acid | Consensus F operably linked to IgE leader |
| 19 | Nucleotide | Optimized N operably linked to IgE leader |
| 20 | Amino acid | Optimized N operably linked to IgE leader |

In one embodiment, nucleic acid molecule can encode a peptide having the amino acid sequence set forth in SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18 or SEQ ID NO:20. In one embodiment, the nucleic acid molecule comprises the nucleotide sequence set forth in SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17 or SEQ ID NO:19. In some embodiments, the sequence can be the nucleotide sequence having at least about 80%, 81%, 82%, 83%, 84%, 85%, 86%, 87%, 88%, 89%, 90%, 91%, 92%, 93%, 94%, 95%, 96%, 97%, 98%, 99% or 100% identity over an entire length of the nucleotide sequence set forth in SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17 or SEQ ID NO:19. In other embodiments, sequence can be the nucleotide sequence that encodes the amino acid sequence having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity over an entire length of the amino acid sequence set forth in SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18 or SEQ ID NO:20.

In some embodiments, the nucleic acid molecule comprises an RNA sequence that is a transcript from a DNA sequence having at least about 80%, 81%, 82%, 83%, 84%, 85%, 86%, 87%, 88%, 89%, 90%, 91%, 92%, 93%, 94%, 95%, 96%, 97%, 98%, 99% or 100% identity over an entire length of the nucleotide sequence set forth in SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17 or SEQ ID NO:19. In some embodiments, the nucleic acid molecule comprises an RNA sequence that encodes an amino acid sequence having at least about 80%, 81%, 82%, 83%, 84%, 85%, 86%, 87%, 88%, 89%, 90%, 91%, 92%, 93%, 94%, 95%, 96%, 97%, 98%, 99% or 100% identity over an entire length of the amino acid sequence set forth in SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18 or SEQ ID NO:20.

In some embodiments, the nucleic acid molecule may comprise a nucleotide sequence that encodes a full length optimized CDV antigen. The nucleic acid molecules may comprise a sequence that encodes SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18 or SEQ ID NO:20. The nucleic acid molecules may comprise a nucleotide sequence of SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17 or SEQ ID NO:19. The nucleic acid molecule may optionally comprise coding sequences that encode a signal peptide such as for example an IgE or IgG signal peptide.

In some embodiments, the nucleic acid molecule may comprise a nucleotide sequence that encodes a full length optimized consensus CDV antigen. The nucleic acid molecules may comprise a sequence that encodes SEQ ID NO:2, SEQ ID NO:4, SEQ ID NO:8, SEQ ID NO:10, SEQ ID NO:14, SEQ ID NO:16 or SEQ ID NO:18. The nucleic acid molecules may comprise a nucleotide sequence of SEQ ID NO:1, SEQ ID NO:3, SEQ ID NO:7, SEQ ID NO:9, SEQ ID NO:13, SEQ ID NO:15 or SEQ ID NO:17. The nucleic acid molecule may optionally comprise coding sequences that encode a signal peptide such as for example an IgE or IgG signal peptide.

The optimized CDV antigen can be a peptide having the amino acid sequence set forth in SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18 or SEQ ID NO:20. In some embodiments, the antigen can have an amino acid sequence having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity over an entire length of the amino acid sequence set forth in SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18 or SEQ ID NO:20.

Immunogenic fragments of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18 or SEQ ID NO:20 can be provided. Immunogenic fragments can comprise at least 60%, at least 65%, at least 70%, at least 75%, at least 80%, at least 85%, at least 90%, at least 95%, at least 96%, at least 97%, at least 98% or at least 99% of the full length of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18 or SEQ ID NO:20. In some embodiments, immunogenic fragments include a leader sequence, such as for example an immunoglobulin leader, such as the IgE leader. In some embodiments, immunogenic fragments are free of a leader sequence.

Immunogenic fragments of proteins with amino acid sequences homologous to immunogenic fragments of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18 or SEQ ID NO:20, can be provided. Such immunogenic fragments can comprise at least 60%, at least 65%, at least 70%, at least 75%, at least 80%, at least 85%, at least 90%, at least 95%, at least 96%, at least 97%, at least 98% or at least 99% of proteins that are 95% homologous to SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18 or SEQ ID NO:20. Some embodiments relate to immunogenic fragments that have 96% homology to the immunogenic fragments of consensus protein sequences herein. Some embodiments relate to immunogenic fragments that have 97% homology to the immunogenic fragments of consensus protein sequences herein. Some embodiments relate to immunogenic fragments that have 98% homology to the immunogenic fragments of consensus protein sequences herein. Some embodiments relate to immunogenic fragments that have 99% homology to the immunogenic fragments of consensus protein sequences herein. In some embodiments, immunogenic fragments include a leader sequence, such as for example an immunoglobulin leader, such as the IgE leader. In some embodiments, immunogenic fragments are free of a leader sequence.

In one embodiment, an immunogenic fragment of a nucleic acid molecule encodes at least one immunodominant or sub-immunodominant epitope of a full length optimized consensus CDV antigen.

Some embodiments relate to immunogenic fragments of SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17 or SEQ ID NO:19 comprising at least 60%, at least 65%, at least 70%, at least 75%, at least 80%, at least 85%, at least 90%, at least 95%, at least 96%, at least 97%, at least 98% or at least 99% of the full length of SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17 or SEQ ID NO:19. Immunogenic fragments can be at least 96%, at least 97% at least 98% or at least 99% homologous to fragments of SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17 or SEQ ID NO:19. In some embodiments, immunogenic fragments include sequences that encode a leader sequence, such as for example an immunoglobulin leader, such as the IgE leader. In some embodiments, fragments are free of coding sequences that encode a leader sequence.

In one embodiment, the nucleic acid molecule comprises a sequence at least 90% homologous to SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17 or SEQ ID NO:19.

In one embodiment, the nucleic acid molecule comprises an RNA sequence encoding an optimized CDV antigen sequence described herein. For example, nucleic acids may comprise an RNA sequence encoding one or more of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18 or SEQ ID NO:20, a variant thereof, a fragment thereof or any combination thereof.

In some embodiments, the nucleic acid molecule includes a sequence that encodes for a CDV antigen minus an IgE leader sequence on the N-terminal end of the coding sequence. In some embodiments, the DNA nucleic acid molecule further comprises an IgE leader sequence attached to an N-terminal end of the coding sequence and operably linked to the promoter.

The nucleic acid molecule can further include a polyadenylation sequence attached to the C-terminal end of the coding sequence. In one embodiment, the nucleic acid molecule is codon optimized.

In some embodiments, the H antigen can be the nucleic acid sequence having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity over an entire length of the nucleic acid sequence set forth in the SEQ ID NO:1. In some embodiments, the H antigen can be an RNA encoded by a DNA sequence having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity over an entire length of the nucleic acid sequence set forth in the SEQ ID NO:1. In some embodiments, the H antigen can be an RNA that encodes an amino acid sequence having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity over an entire length of the amino acid sequence set forth in SEQ ID NO:2. In other embodiments, the H antigen can be the nucleic acid sequence that encodes the amino acid sequence having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity over an entire length of the amino acid sequence set forth in one of SEQ ID NO:2. The H antigen can be the amino acid sequence having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity over an entire length of the amino acid sequence set forth in SEQ ID NO:2.

In some embodiments, the N antigen can be the nucleic acid sequence having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity over an entire length of the nucleic acid sequence set forth in the SEQ ID NO:5. In some embodiments, the N antigen can be an RNA encoded by a DNA sequence having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity over an entire length of the nucleic acid sequence set forth in the SEQ ID NO:5. In some embodiments, the N antigen can be an RNA that encodes an amino acid sequence having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity over an entire length of the amino acid sequence set forth in SEQ ID NO:6. In other embodiments, the N antigen can be the nucleic acid sequence that encodes the amino acid sequence having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity over an entire length of the amino acid sequence set forth in one of SEQ ID NO:6. The N antigen can be the amino acid sequence having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity over an entire length of the amino acid sequence set forth in SEQ ID NO:6.

In some embodiments, the F antigen can be the nucleic acid sequence having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity over an entire length of the nucleic acid sequence set forth in the SEQ ID NO:9. In some embodiments, the F antigen can be an RNA encoded by a DNA sequence having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity over an entire length of the nucleic acid sequence set forth in the SEQ ID NO:9. In some embodiments, the F antigen can be an RNA that encodes an amino acid sequence having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity over an entire length of the amino acid sequence set forth in SEQ ID NO:10. In other embodiments, the F antigen can be the nucleic acid sequence that encodes the amino acid sequence having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity over an entire length of the amino acid sequence set forth in one of SEQ ID NO:10. The F antigen can be the amino acid sequence having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity over an entire length of the amino acid sequence set forth in SEQ ID NO:10.

Some embodiments relate to fragments of SEQ ID NO:1, SEQ ID NO:2, SEQ ID NO:3, SEQ ID NO:4, SEQ ID NO:5 or SEQ ID NO:6. Fragments can be at least 10%, at least 15%, at least 20%, at least 25%, at least 30%, at least 35%, at least 40%, at least 45%, at least 50%, at least 55% at least 60%, at least 65%, at least 70%, at least 75%, at least 80%, at least 85%, at least 90%, at least 95%, at least 96%, at least 97%, at least 98% or at least 99% of SEQ ID NO:1. Fragments can be at least 95%, at least 96%, at least 97%, at least 98%, or at least 99% homologous to fragments of SEQ ID NO:1, SEQ ID NO:2, SEQ ID NO:3, SEQ ID NO:4, SEQ ID NO:5 or SEQ ID NO:6. Fragments can be at least 80%, at least 85%, at least 90% at least 91%, at least 92%, at least 93%, at least 94%, at least 95%, at least 96%, at least 97%, at least 98%, or at least 99% identical to fragments of SEQ ID NO:1, SEQ ID NO:2, SEQ ID NO:3, SEQ ID NO:4, SEQ ID NO:5 or SEQ ID NO:6. In some embodiments, fragments include sequences that encode a leader sequence, such as for example, an immunoglobulin leader, such as the IgE leader. In some embodiments, fragments are free of coding sequences that encode a leader sequence. In some embodiments, fragments are free of coding sequences that encode a leader sequence, such as for example, the IgE leader.

Fragments of SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17 or SEQ ID NO:19 may comprise at least 30, 45, 60, 75, 90, 120, 150, 180, 210, 240, 270, 300, 360, 420, 480, 540, 600, 660, 720, 780, 840, 900, 960, 1020, 1080, 1140, 1200, 1260, 1320, 1380, 1440, 1500, 1560, or more nucleotides of SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17 or SEQ ID NO:19. In one embodiment, fragments of SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17 or SEQ ID NO:19 comprise sequences that encode an immunodominant epitope.

Fragments of SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17 or SEQ ID NO:19 may comprise fewer than 60, 75, 90, 120, 150, 180, 210, 240, 270, 300, 360, 420, 480, 540, 600, 660, 720, 780, 840, 900, 960, 1020, 1080, 1140, 1200, 1260, 1320, 1380, 1440, 1500, 1560, or fewer than 1560 nucleotides of SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17 or SEQ ID NO:19.

Fragments of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18 or SEQ ID NO:20 may comprise at least 15, 18, 21, 24, 30, 36, 42, 48, 54, 60, 72, 90, 120, 150, 180, 210, 240, 270, 300, 330, 360, 390, 420, 450, 480, 510, or more amino acids of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18 or SEQ ID NO:20. In some embodiments, fragments of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18 or SEQ ID NO:20 comprise an immunodominant epitope.

Fragments of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18 or SEQ ID NO:20 may comprise fewer than 24, 30, 36, 42, 48, 54, 60, 72, 90, 120, 150, 180, 210, 240, 270, 300, 330, 360, 390, 420, 450, 480, 510, or fewer than 1110 amino acids of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18 or SEQ ID NO:20.

3. VACCINE CONSTRUCTS AND PLASMIDS

The vaccine can comprise nucleic acid constructs or plasmids that encode the above described antigens. The nucleic acid constructs or plasmids can include or contain one or more heterologous nucleic acid sequences. Provided herein are genetic constructs that can comprise a nucleic acid sequence that encodes the above described antigens. The genetic construct can be present in the cell as a functioning extrachromosomal molecule. The genetic construct can be a linear minichromosome including centromere, telomeres or plasmids or cosmids. The genetic constructs can include or contain one or more heterologous nucleic acid sequences.

The genetic constructs can be in the form of plasmids expressing the above described antigens in any order.

The genetic construct can also be part of a genome of a recombinant viral vector, including recombinant adenovirus, recombinant adenovirus associated virus and recombinant vaccinia. The genetic construct can be part of the genetic material in attenuated live microorganisms or recombinant microbial vectors which live in cells.

The genetic constructs can comprise regulatory elements for gene expression of the coding sequences of the nucleic acid. The regulatory elements can be a promoter, an enhancer an initiation codon, a stop codon, or a polyadenylation signal.

The nucleic acid sequences can make up a genetic construct that can be a vector. The vector can be capable of expressing the above described antigens in the cell of a mammal in a quantity effective to elicit an immune response in the mammal. The vector can be recombinant. The vector can comprise heterologous nucleic acid encoding the above described antigens. The vector can be a plasmid. The vector can be useful for transfecting cells with nucleic acid encoding the above described antigens, which the transformed host cell is cultured and maintained under conditions wherein expression of the above described antigens takes place.

Coding sequences can be optimized for stability and high levels of expression. In some instances, codons are selected to reduce secondary structure formation of the RNA such as that formed due to intramolecular bonding.

The vector can comprise heterologous nucleic acid encoding the above described antigens and can further comprise an initiation codon, which can be upstream of the one or more CDV antigen coding sequence(s), and a stop codon, which can be downstream of the coding sequence(s) of the above described antigens. The initiation and termination codon can be in frame with the coding sequence(s) of the above described antigens. The vector can also comprise a promoter that is operably linked to the coding sequence(s) of the above described antigens. The promoter operably linked to the coding sequence(s) of the above described antigens can be a promoter from simian virus 40 (SV40), a mouse mammary tumor virus (MMTV) promoter, a human immunodeficiency virus (HIV) promoter such as the bovine immunodeficiency virus (BIV) long terminal repeat (LTR) promoter, a Moloney virus promoter, an avian leukosis virus (ALV) promoter, a cytomegalovirus (CMV) promoter such as the CMV immediate early promoter, Epstein Barr virus (EBV) promoter, or a Rous sarcoma virus (RSV) promoter. The promoter can also be a promoter from a human gene such as human actin, human myosin, human hemoglobin, human muscle creatine, or human metalothionein. The promoter can also be a tissue specific promoter, such as a muscle or skin specific promoter, natural or synthetic. Examples of such promoters are described in US patent application publication no. US20040175727, the contents of which are incorporated herein in its entirety.

The vector can also comprise a polyadenylation signal, which can be downstream of the coding sequence(s) of the above described antigens. The polyadenylation signal can be a SV40 polyadenylation signal, LTR polyadenylation signal, bovine growth hormone (bGH) polyadenylation signal, human growth hormone (hGH) polyadenylation signal, or human (3-globin polyadenylation signal. The SV40 polyadenylation signal can be a polyadenylation signal from a pCEP4 vector (Invitrogen, San Diego, CA).

The vector can also comprise an enhancer upstream of the above described antigens. The enhancer can be necessary for DNA expression. The enhancer can be human actin, human myosin, human hemoglobin, human muscle creatine or a viral enhancer such as one from CMV, HA, RSV or EBV. Polynucleotide function enhancers are described in U.S. Pat. Nos. 5,593,972, 5,962,428, and WO94/016737, the contents of each are fully incorporated by reference.

The vector can also comprise a mammalian origin of replication in order to maintain the vector extrachromosomally and produce multiple copies of the vector in a cell. The vector can be pVAX1, pCEP4 or pREP4 from Invitrogen (San Diego, CA), which can comprise the Epstein Barr virus origin of replication and nuclear antigen EBNA-1 coding region, which can produce high copy episomal replication without integration. The vector can be pVAX1 or a pVax1 variant with changes such as the variant plasmid described herein. The variant pVax1 plasmid is a 2998 basepair variant of the backbone vector plasmid pVAX1 (Invitrogen, Carlsbad CA). The CMV promoter is located at bases 137-724. The T7 promoter/priming site is at bases 664-683. Multiple cloning sites are at bases 696-811. Bovine GH polyadenylation signal is at bases 829-1053. The Kanamycin resistance gene is at bases 1226-2020. The pUC origin is at bases 2320-2993.

The backbone of the vector can be pAV0242. The vector can be a replication defective adenovirus type 5 (Ad5) vector.

The vector can also comprise a regulatory sequence, which can be well suited for gene expression in a mammalian or canine cell into which the vector is administered. The one or more CDV antigen sequences disclosed herein can comprise a codon, which can allow more efficient transcription of the coding sequence in the host cell.

The vector can be pSE420 (Invitrogen, San Diego, Calif.), which can be used for protein production in *Escherichia coli* (*E. coli*). The vector can also be pYES2 (Invitrogen, San Diego, Calif.), which can be used for protein production in *Saccharomyces cerevisiae* strains of yeast. The vector can also be of the MAXBAC™ complete baculovirus expression system (Invitrogen, San Diego, Calif.), which can be used for protein production in insect cells. The vector can also be pcDNA I or pcDNA3 (Invitrogen, San Diego, Calif.), which may be used for protein production in mammalian cells, such as Chinese hamster ovary (CHO) cells. The vector can be expression vectors or systems to produce protein by routine techniques and readily available starting materials including Sambrook et al., Molecular Cloning and Laboratory Manual, Second Ed., Cold Spring Harbor (1989), which is incorporated fully by reference.

In some embodiments, the vector can comprise one or more of the nucleic acid sequences of SEQ ID NO:1, SEQ ID NO:2 and SEQ ID NO:5, or a fragment or variant thereof.

4. VACCINES AND IMMUNOGENIC COMPOSITIONS

Immunogenic compositions, such as vaccines, are provided comprising an optimized CDV sequence, an optimized consensus CDV antigen, a fragment thereof, a variant thereof, or a combination thereof. The immunogenic composition can significantly induce an immune response of a subject administered with the immunogenic composition against the CDV antigen. The vaccine may comprise a plurality of the nucleic acid molecules, or combinations thereof. The vaccine may be provided to induce a therapeutic or prophylactic immune response.

The immunogenic composition can be a DNA vaccine, an RNA vaccine, a peptide vaccine, or a combination vaccine. The vaccine can include an optimized consensus nucleotide sequence encoding an antigen. The nucleotide sequence can be DNA, RNA, cDNA, a variant thereof, a fragment thereof, or a combination thereof. The nucleotide sequence can also include additional sequences that encode linker, leader, or tag sequences that are linked to the antigen by a peptide bond. The peptide vaccine can include an antigen, a variant thereof, a fragment thereof, or a combination thereof. The combination DNA and peptide vaccine can include the above described optimized CDV nucleotide sequence and the encoded antigen.

The vaccine can be a DNA vaccine. DNA vaccines are disclosed in U.S. Pat. Nos. 5,593,972, 5,739,118, 5,817,637, 5,830,876, 5,962,428, 5,981,505, 5,580,859, 5,703,055, and 5,676,594, which are incorporated herein fully by reference. The DNA vaccine can further comprise elements or reagents that inhibit it from integrating into the chromosome.

The vaccine can be an RNA of the one or more CDV antigens. The RNA vaccine can be introduced into the cell.

The vaccine can be an attenuated live vaccine, a vaccine using recombinant vectors to deliver antigen, subunit vaccines, and glycoprotein vaccines, for example, but not limited, the vaccines described in U.S. Pat. Nos. 4,510,245; 4,797,368; 4,722,848; 4,790,987; 4,920,209; 5,017,487; 5,077,044; 5,110,587; 5,112,749; 5,174,993; 5,223,424; 5,225,336; 5,240,703; 5,242,829; 5,294,441; 5,294,548; 5,310,668; 5,387,744; 5,389,368; 5,424,065; 5,451,499; 5,453,364; 5,462,734; 5,470,734; 5,474,935; 5,482,713; 5,591,439; 5,643,579; 5,650,309; 5,698,202; 5,955,088; 6,034,298; 6,042,836; 6,156,319 and 6,589,529, which are each incorporated herein by reference.

The vaccine of the present invention can have features required of effective vaccines such as being safe so that the vaccine itself does not cause illness or death; being protective against illness; inducing protective T cell responses; and providing ease of administration, few side effects, biological stability, and low cost per dose.

Provided herein is an immunogenic composition capable of generating in a mammal an immune response against CDV. The immunogenic composition may comprise each plasmid as discussed above. The immunogenic composition may comprise a plurality of the plasmids, or combinations thereof. The immunogenic composition may be provided to induce a therapeutic or prophylactic immune response.

Immunogenic compositions may be used to deliver nucleic acid molecules that encode one or more optimized CDV antigen. Immunogenic compositions are preferably compositions comprising plasmids.

The immunogenic composition may further comprise a pharmaceutically acceptable excipient. The pharmaceutically acceptable excipient may be functional molecules as vehicles, adjuvants, carriers, or diluents. The pharmaceutically acceptable excipient may be a transfection facilitating agent, which may include surface active agents, such as immune-stimulating complexes (ISCOMS), Freunds incomplete adjuvant, LPS analog including monophosphoryl lipid A, muramyl peptides, quinone analogs, vesicles such as squalene and squalene, hyaluronic acid, lipids, liposomes, calcium ions, viral proteins, polyanions, polycations, or nanoparticles, or other known transfection facilitating agents.

The transfection facilitating agent is a polyanion, polycation, including poly-L-glutamate (LGS), or lipid. The transfection facilitating agent is poly-L-glutamate, and more preferably, the poly-L-glutamate is present in the immunogenic composition at a concentration less than 6 mg/ml. The transfection facilitating agent may also include surface active agents such as immune-stimulating complexes (ISCOMS), Freunds incomplete adjuvant, LPS analog including monophosphoryl lipid A, muramyl peptides, quinone analogs and vesicles such as squalene and squalene, and hyaluronic acid may also be used administered in conjunction with the genetic construct. In some embodiments, the immunogenic compositions may also include a transfection facilitating agent such as lipids, liposomes, including lecithin liposomes or other liposomes known in the art, as a DNA-liposome mixture (see for example WO9324640), calcium ions, viral proteins, polyanions, polycations, or nanoparticles, or other known transfection facilitating agents. Preferably, the transfection facilitating agent is a polyanion, polycation, including poly-L-glutamate (LGS), or lipid. Concentration of the transfection agent in the immunogenic composition is less than 4 mg/ml, less than 2 mg/ml, less than 1 mg/ml, less than 0.750 mg/ml, less than 0.500 mg/ml, less than 0.250 mg/ml, less than 0.100 mg/ml, less than 0.050 mg/ml, or less than 0.010 mg/ml.

The pharmaceutically acceptable excipient may be one or more adjuvants. An adjuvant may be other genes that are expressed from the same or from an alternative plasmid or are delivered as proteins in combination with the plasmid above in the immunogenic composition. The one or more adjuvants may be proteins and/or nucleic acid molecules that encode proteins selected from the group consisting of: CCL20, α-interferon (IFN-α), β-interferon (IFN-β), γ-interferon, platelet derived growth factor (PDGF), TNFα, TNFβ, GM-CSF, epidermal growth factor (EGF), cutaneous T cell-attracting chemokine (CTACK), epithelial thymus-expressed chemokine (TECK), mucosae-associated epithelial chemokine (MEC), IL-12, IL-15 including IL-15 having the signal sequence or coding sequence that encodes the signal sequence deleted and optionally including a different signal peptide such as that from IgE or coding sequence that encodes a difference signal peptide such as that from IgE, IL-28, MHC, CD80, CD86, IL-1, IL-2, IL-4, IL-5, IL-6, IL-10, IL-18, MCP-1, MIP-1α, MIP-1β, IL-8, L-selectin, P-selectin, E-selectin, CD34, GlyCAM-1, MadCAM-1, LFA-1, VLA-1, Mac-1, p150.95, PECAM, ICAM-1, ICAM-2, ICAM-3, CD2, LFA-3, M-CSF, G-CSF, mutant forms of IL-18, CD40, CD40L, vascular growth factor, fibroblast growth factor, IL-7, nerve growth factor, vascular endothelial growth factor, Fas, TNF receptor, Flt, Apo-1, p55, WSL-1, DR3, TRAMP, Apo-3, AIR, LARD, NGRF, DR4, DR5, KILLER, TRAIL-R2, TRICK2, DR6, Caspase ICE, Fos, c-jun, Sp-1, Ap-1, Ap-2, p38, p65Rel, MyD88, IRAK, TRAF6, IkB, Inactive NIK, SAP K, SAP-1, JNK, interferon response genes, NFkB, Bax, TRAIL, TRAILrec, TRAIL-recDRC5, TRAIL-R3, TRAIL-R4, RANK, RANK LIGAND, Ox40, Ox40 LIGAND, NKG2D, MICA, MICB, NKG2A, NKG2B, NKG2C, NKG2E, NKG2F, TAP1, TAP2 and functional fragments thereof or a combination thereof.

In some embodiments, the adjuvant may be one or more proteins and/or nucleic acid molecules that encode proteins selected from the group consisting of: CCL-20, IL-12, IL-15, IL-28, CTACK, TECK, MEC or RANTES. Examples of IL-12 constructs and sequences are disclosed in PCT application no. PCT/US1997/019502 and corresponding U.S. application Ser. No. 08/956,865, and U.S. Provisional Application Ser. No. 61/569,600 filed Dec. 12, 2011, which are each incorporated herein by reference. Examples of IL-15 constructs and sequences are disclosed in PCT application no. PCT/US04/18962 and corresponding U.S. application Ser. No. 10/560,650, and in PCT application no. PCT/US07/00886 and corresponding U.S. application Ser. No. 12/160,766, and in PCT application no. PCT/US10/048827, which are each incorporated herein by reference. Examples of IL-28 constructs and sequences are disclosed in PCT application no. PCT/US09/039648 and corresponding U.S. application Ser. No. 12/936,192, which are each incorporated herein by reference. Examples of RANTES and other constructs and sequences are disclosed in PCT application no. PCT/US1999/004332 and corresponding U.S. application Ser. No. 09/622,452, which are each incorporated herein by reference. Other examples of RANTES constructs and sequences are disclosed in PCT application no. PCT/US11/024098, which is incorporated herein by reference. Examples of RANTES and other constructs and sequences are disclosed in PCT application no. PCT/US1999/004332 and corresponding U.S. application Ser. No. 09/622,452, which are each incorporated herein by reference. Other examples of RANTES constructs and sequences are disclosed in PCT application no. PCT/US11/024098, which is incorporated herein by reference. Examples of chemokines CTACK, TECK and MEC constructs and sequences are disclosed in PCT application no. PCT/US2005/042231 and corresponding U.S. application Ser. No. 11/719,646, which are each incorporated herein by reference. Examples of OX40 and other immunomodulators are disclosed in U.S. application Ser. No. 10/560,653, which is incorporated herein by reference. Examples of DR5 and other immunomodulators are disclosed in U.S. application Ser. No. 09/622,452, which is incorporated herein by reference.

The immunogenic composition may further comprise a genetic vaccine facilitator agent as described in U.S. Ser. No. 021,579 filed Apr. 1, 1994, which is fully incorporated by reference.

The immunogenic composition may comprise the CDV antigens or plasmids encoding the same at quantities of from about 1 nanogram to 100 milligrams; about 1 microgram to about 10 milligrams; or preferably about 0.1 microgram to about 10 milligrams; or more preferably about 1 milligram to about 2 milligram. In some preferred embodiments, pharmaceutical compositions according to the present invention comprise about 5 nanogram to about 1000 micrograms of DNA. In some preferred embodiments, the pharmaceutical compositions contain about 10 nanograms to about 800 micrograms of DNA. In some preferred embodiments, the pharmaceutical compositions contain about 0.1 to about 500 micrograms of DNA. In some preferred embodiments, the pharmaceutical compositions contain about 1 to about 350 micrograms of DNA. In some preferred embodiments, the pharmaceutical compositions contain about 25 to about 250 micrograms, from about 100 to about 200 microgram, from about 1 nanogram to 100 milligrams; from about 1 microgram to about 10 milligrams; from about 0.1 microgram to about 10 milligrams; from about 1 milligram to about 2 milligram, from about 5 nanogram to about 1000 micrograms, from about 10 nanograms to about 800 micrograms, from about 0.1 to about 500 micrograms, from about 1 to about 350 micrograms, from about 25 to about 250 micrograms, from about 100 to about 200 microgram of the CDV antigen or plasmid thereof.

In some embodiments, pharmaceutical compositions according to the present invention comprise at least 10, 15, 20, 25, 30, 35, 40, 45, 50, 55, 60, 65, 70, 75, 80, 85, 90, 95 or 100 nanograms of a nucleic acid molecule of the invention. In some embodiments, the pharmaceutical compositions can comprise at least 1, 5, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 405, 410, 415, 420, 425, 430, 435, 440, 445, 450, 455, 460, 465, 470, 475, 480, 485, 490, 495, 500, 605, 610, 615, 620, 625, 630, 635, 640, 645, 650, 655, 660, 665, 670, 675, 680, 685, 690, 695, 700, 705, 710, 715, 720, 725, 730, 735, 740, 745, 750, 755, 760, 765, 770, 775, 780, 785, 790, 795, 800, 805, 810, 815, 820, 825, 830, 835, 840, 845, 850, 855, 860, 865, 870, 875, 880, 885, 890, 895. 900, 905, 910, 915, 920, 925, 930, 935, 940, 945, 950, 955, 960, 965, 970, 975, 980, 985, 990, 995 or 1000 micrograms of a nucleic acid molecule of the invention. In some embodiments, the pharmaceutical composition can comprise at least 1.5, 2, 2.5, 3, 3.5, 4, 4.5, 5, 5.5, 6, 6.5, 7, 7.5, 8, 8.5, 9, 9.5 or 10 mg or more of a nucleic acid molecule of the invention.

In other embodiments, the pharmaceutical composition can comprise up to and including 15, 20, 25, 30, 35, 40, 45, 50, 55, 60, 65, 70, 75, 80, 85, 90, 95 or 100 nanograms of a nucleic acid molecule of the invention. In some embodiments, the pharmaceutical composition can comprise up to and including 1, 5, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 405, 410, 415, 420, 425, 430, 435, 440, 445, 450, 455, 460, 465, 470, 475, 480, 485, 490, 495, 500, 605, 610, 615, 620, 625, 630, 635, 640, 645, 650, 655, 660, 665, 670, 675, 680, 685, 690, 695, 700, 705, 710, 715, 720, 725, 730, 735, 740, 745, 750, 755, 760, 765, 770, 775, 780, 785, 790, 795, 800, 805, 810, 815, 820, 825, 830, 835, 840, 845, 850, 855, 860, 865, 870, 875, 880, 885, 890, 895. 900, 905, 910, 915, 920, 925, 930, 935, 940, 945, 950, 955, 960, 965, 970, 975, 980, 985, 990, 995, or 1000 micrograms of a nucleic acid molecule of the invention. In some embodiments, the pharmaceutical composition can comprise up to and including 1.5, 2, 2.5, 3, 3.5, 4, 4.5, 5, 5.5, 6, 6.5, 7, 7.5, 8, 8.5, 9, 9.5 or 10 mg of a nucleic acid molecule of the invention.

The immunogenic composition may be formulated according to the mode of administration to be used. An injectable immunogenic composition pharmaceutical composition may be sterile, pyrogen free and particulate free. An isotonic formulation or solution may be used. Additives for isotonicity may include sodium chloride, dextrose, mannitol, sorbitol, and lactose. The immunogenic composition may comprise a vasoconstriction agent. The isotonic solutions may include phosphate buffered saline. Immunogenic composition may further comprise stabilizers including gelatin and albumin. The stabilizing may allow the formulation to be stable at room or ambient temperature for extended periods of time such as LGS or polycations or polyanions to the immunogenic composition formulation.

The immunogenic composition may be stable at room temperature (25° C.) for more than 1 week, in some embodiments for more than 2 weeks, in some embodiments for more than 3 weeks, in some embodiments for more than 4 weeks, in some embodiments for more than 5 weeks, and in some embodiments for more than 6 weeks. In some embodiments, the vaccine is stable for more than one month, more than 2 months, more than 3 months, more than 4 months, more than 5 months, more than 6 months, more than 7 months, more than 8 months, more than 9 months, more than 10 months, more than 11 months, or more than 12 months. In some embodiments, the vaccine is stable for more than 1 year, more than 2 years, more than years, or more than 5 years. In one embodiment, the immunogenic composition is stable under refrigeration (2-8° C.). Accordingly, in one embodiment, the immunogenic composition does not require frozen cold-chain. An immunogenic composition is stable if it retains its biological activity for a sufficient period to allow its intended use (e.g., to generate an immune response in a subject). For example, for immunogenic compositions that are to be stored, shipped, etc., it may be desired that the immunogenic compositions remain stable for months to years.

5. IMMUNE RESPONSE

The immunogenic composition can induce an immune response in the subject administered the composition. The induced immune response can be specific for a CDV antigen. The induced immune response can be reactive with a CDV antigen related to the optimized CDV antigen. In various embodiments, related antigens include antigens having amino acid sequences having at least 90%, at least 91%, at least 92%, at least 93%, at least 94%, at least 95%, at least 96%, at least 97%, at least 98%, at least 99%, or 100% homology to the amino acid sequence of the optimized CDV antigen. In various embodiments, related antigens include antigens encoded by nucleotide sequences having at least 90%, at least 91%, at least 92%, at least 93%, at least 94%, at least 95%, at least 96%, at least 97%, at least 98%, at least 99%, or 100% homology to the optimized CDV nucleotide sequences disclosed herein.

The immunogenic composition can induce a humoral immune response in the subject administered the immunogenic composition. The induced humoral immune response can be specific for a CDV antigen. The induced humoral immune response can be reactive with the CDV antigen related to the optimized CDV antigen. The humoral immune response can be induced in the subject administered the immunogenic composition by about 1.5-fold to about 16-fold, about 2-fold to about 12-fold, or about 3-fold to about 10-fold. The humoral immune response can be induced in the subject administered the immunogenic composition by at least about 1.5-fold, at least about 2.0-fold, at least about 2.5-fold, at least about 3.0-fold, at least about 3.5-fold, at least about 4.0-fold, at least about 4.5-fold, at least about 5.0-fold, at least about 5.5-fold, at least about 6.0-fold, at least about 6.5-fold, at least about 7.0-fold, at least about 7.5-fold, at least about 8.0-fold, at least about 8.5-fold, at least about 9.0-fold, at least about 9.5-fold, at least about 10.0-fold, at least about 10.5-fold, at least about 11.0-fold, at least about 11.5-fold, at least about 12.0-fold, at least about 12.5-fold, at least about 13.0-fold, at least about 13.5-fold, at least about 14.0-fold, at least about 14.5-fold, at least about 15.0-fold, at least about 15.5-fold, or at least about 16.0-fold as compared to a subject not administered the immunogenic composition or a subject administered a non-optimized CDV antigen.

The humoral immune response induced by the immunogenic composition can include an increased level of IgG antibodies associated with the subject administered the immunogenic composition as compared to a subject not administered the immunogenic composition. These IgG antibodies can be specific for the CDV antigen genetically related to the optimized CDV antigen. These IgG antibodies can be reactive with the CDV antigen genetically related to the optimized CDV antigen. The level of IgG antibody associated with the subject administered the immunogenic composition can be increased by about 1.5-fold to about 16-fold, about 2-fold to about 12-fold, or about 3-fold to about 10-fold as compared to the subject not administered the immunogenic composition. The level of IgG antibody associated with the subject administered the immunogenic composition can be increased by at least about 1.5-fold, at least about 2.0-fold, at least about 2.5-fold, at least about 3.0-fold, at least about 3.5-fold, at least about 4.0-fold, at least about 4.5-fold, at least about 5.0-fold, at least about 5.5-fold, at least about 6.0-fold, at least about 6.5-fold, at least about 7.0-fold, at least about 7.5-fold, at least about 8.0-fold, at least about 8.5-fold, at least about 9.0-fold, at least about 9.5-fold, at least about 10.0-fold, at least about 10.5-fold, at least about 11.0-fold, at least about 11.5-fold, at least about 12.0-fold, at least about 12.5-fold, at least about 13.0-fold, at least about 13.5-fold, at least about 14.0-fold, at least about 14.5-fold, at least about 15.0-fold, at least about 15.5-fold, or at least about 16.0-fold as compared to a subject not administered the immunogenic composition or a subject administered a non-optimized CDV antigen.

The immunogenic composition can induce a cellular immune response in the subject administered the immunogenic composition. The induced cellular immune response can be specific for a CDV antigen related to the optimized CDV antigen. The induced cellular immune response can be reactive to a CDV antigen related to the optimized CDV antigen. The induced cellular immune response can include eliciting a CD8+ T cell response. The elicited CD8+ T cell response can be reactive with a CDV antigen genetically related to the optimized CDV antigen. The elicited CD8+ T cell response can be polyfunctional. The induced cellular immune response can include eliciting a CD8+ T cell response, in which the CD8+ T cells produce interferon-gamma (IFN-γ), tumor necrosis factor alpha (TNF-α), interleukin-2 (IL-2), or a combination of IFN-γ and TNF-α.

The induced cellular immune response can include an increased CD8+ T cell response associated with the subject administered the immunogenic composition as compared to the subject not administered the immunogenic composition. The CD8+ T cell response associated with the subject administered the immunogenic composition can be increased by about 2-fold to about 30-fold, about 3-fold to about 25-fold, or about 4-fold to about 20-fold as compared to the subject not administered the immunogenic composition. The CD8+ T cell response associated with the subject administered the immunogenic composition can be increased by at least about 1.5-fold, at least about 2.0-fold, at least about 3.0-fold, at least about 4.0-fold, at least about 5.0-fold, at least about 6.0-fold, at least about 6.5-fold, at least about 7.0-fold, at least about 7.5-fold, at least about 8.0-fold, at least about 8.5-fold, at least about 9.0-fold, at least about 9.5-fold, at least about 10.0-fold, at least about 10.5-fold, at least about 11.0-fold, at least about 11.5-fold, at least about 12.0-fold, at least about 12.5-fold, at least about 13.0-fold, at least about 13.5-fold, at least about 14.0-fold, at least about 14.5-fold, at least about 15.0-fold, at least about 16.0-fold, at least about 17.0-fold, at least about 18.0-fold, at least about 19.0-fold, at least about 20.0-fold, at least about 21.0-fold, at least about 22.0-fold, at least about 23.0-fold, at least about 24.0-fold, at least about 25.0-fold, at least about 26.0-fold, at least about 27.0-fold, at least about 28.0-fold, at least about 29.0-fold, or at least about 30.0-fold as compared to a subject not administered the immunogenic composition or a subject administered a non-optimized CDV antigen.

The induced cellular immune response can include an increased frequency of CD107a/IFNγ/T-bet triple-positive CD8 T cells that are reactive against the CDV antigen. The frequency of CD107a/IFNγ/T-bet triple-positive CD8 T cells associated with the subject administered the immunogenic composition can be increased by at least about 2-fold, 3-fold, 4-fold, 5-fold, 6-fold, 7-fold, 8-fold, 9-fold, 10-fold, 11-fold, 12-fold, 13-fold, 14-fold, 15-fold, 16-fold, 17-fold, 18-fold, 19-fold, or 20-fold as compared to a subject not administered the immunogenic composition or a subject administered a non-optimized CDV antigen.

The induced cellular immune response can include an increased frequency of CD107a/IFNγ double-positive CD8 T cells that are reactive against the CDV antigen. The frequency of CD107a/IFNγ double-positive CD8 T cells associated with the subject administered the immunogenic composition can be increased by at least about 2-fold, 3-fold, 4-fold, 5-fold, 6-fold, 7-fold, 8-fold, 9-fold, 10-fold, 11-fold, 12-fold, 13-fold, or 14-fold as compared to a subject not administered the immunogenic composition or a subject administered a non-optimized CDV antigen.

The cellular immune response induced by the immunogenic composition can include eliciting a CD4+ T cell response. The elicited CD4+ T cell response can be reactive with a CDV antigen genetically related to the optimized CDV antigen. The elicited CD4+ T cell response can be polyfunctional. The induced cellular immune response can include eliciting a CD4+ T cell response, in which the CD4+ T cells produce IFN-γ, TNF-α, IL-2, or a combination of IFN-γ and TNF-α.

The induced cellular immune response can include an increased frequency of CD4+ T cells that produce IFN-γ. The frequency of CD4+IFN-γ+ T cells associated with the subject administered the immunogenic composition can be increased by at least about 2-fold, 3-fold, 4-fold, 5-fold, 6-fold, 7-fold, 8-fold, 9-fold, 10-fold, 11-fold, 12-fold, 13-fold, 14-fold, 15-fold, 16-fold, 17-fold, 18-fold, 19-fold, or 20-fold as compared to a subject not administered the immunogenic composition or a subject administered a non-optimized CDV antigen.

The induced cellular immune response can include an increased frequency of CD4+ T cells that produce TNF-α. The frequency of CD4+TNF-α+ T cells associated with the subject administered the immunogenic composition can be increased by at least about 2-fold, 3-fold, 4-fold, 5-fold, 6-fold, 7-fold, 8-fold, 9-fold, 10-fold, 11-fold, 12-fold, 13-fold, 14-fold, 15-fold, 16-fold, 17-fold, 18-fold, 19-fold, 20-fold, 21-fold, or 22-fold as compared to a subject not administered the immunogenic composition or a subject administered a non-optimized CDV antigen.

The induced cellular immune response can include an increased frequency of CD4+ T cells that produce both IFN-γ and TNF-α. The frequency of CD4+IFN-γ+TNF-α+ associated with the subject administered the immunogenic composition can be increased by at least about 2-fold, 2.5-fold, 3.0-fold, 3.5-fold, 4.0-fold, 4.5-fold, 5.0-fold, 5.5-fold, 6.0-fold, 6.5-fold, 7.0-fold, 7.5-fold, 8.0-fold, 8.5-fold, 9.0-fold, 9.5-fold, 10.0-fold, 10.5-fold, 11.0-fold, 11.5-fold, 12.0-fold, 12.5-fold, 13.0-fold, 13.5-fold, 14.0-fold, 14.5-fold, 15.0-fold, 15.5-fold, 16.0-fold, 16.5-fold, 17.0-fold, 17.5-fold, 18.0-fold, 18.5-fold, 19.0-fold, 19.5-fold, 20.0-fold, 21-fold, 22-fold, 23-fold 24-fold, 25-fold, 26-fold, 27-fold, 28-fold, 29-fold, 30-fold, 31-fold, 32-fold, 33-fold, 34-fold, or 35-fold as compared to a subject not administered the immunogenic composition or a subject administered a non-optimized CDV antigen.

The immunogenic composition can further induce an immune response when administered to different tissues such as the muscle or skin. The immunogenic composition can further induce an immune response when administered via electroporation, or injection, or subcutaneously, or intramuscularly.

6. VECTOR

The nucleotide construct described above can be placed in one or more vectors. The one or more vectors can contain an origin of replication. The one or more vectors can be a plasmid, bacteriophage, bacterial artificial chromosome or yeast artificial chromosome. The one or more vectors can be either a self-replication extra chromosomal vector, or a vector which integrates into a host genome.

Vectors include, but are not limited to, plasmids, expression vectors, recombinant viruses, any form of recombinant "naked DNA" vector, and the like. A "vector" comprises a nucleic acid which can infect, transfect, transiently or permanently transduce a cell. It will be recognized that a vector can be a naked nucleic acid, or a nucleic acid complexed with protein or lipid. The vector optionally comprises viral or bacterial nucleic acids and/or proteins, and/or membranes (e.g., a cell membrane, a viral lipid envelope, etc.). Vectors include, but are not limited to replicons (e.g., RNA replicons, bacteriophages) to which fragments of DNA may be attached and become replicated. Vectors thus include, but are not limited to RNA, autonomous self-replicating circular or linear DNA or RNA (e.g., plasmids, viruses, and the like, see, e.g., U.S. Pat. No. 5,217,879), and include both the expression and non-expression plasmids. Where a recombinant microorganism or cell culture is described as hosting an "expression vector" this includes both extra-chromosomal circular and linear DNA and DNA that has been incorporated into the host chromosome(s). Where a vector is being maintained by a host cell, the vector may either be stably replicated by the cells during mitosis as an autonomous structure, or is incorporated within the host's genome.

The one or more vectors can be an expression construct, which is generally a plasmid that is used to introduce a specific gene into a target cell. Once the expression vector is inside the cell, the protein that is encoded by the gene is produced by the cellular-transcription and translation machinery ribosomal complexes. The plasmid is frequently engineered to contain regulatory sequences that act as enhancer and promoter regions and lead to efficient transcription of the gene carried on the expression vector. The vectors of the present invention express large amounts of stable messenger RNA, and therefore proteins.

The vectors may have expression signals such as a strong promoter, a strong termination codon, adjustment of the distance between the promoter and the cloned gene, and the insertion of a transcription termination sequence and a PTIS (portable translation initiation sequence).

Expression Vector

The one or more vectors can be a circular plasmid or a linear nucleic acid. The circular plasmid and linear nucleic acid are capable of directing expression of a particular nucleotide sequence in an appropriate subject cell. The one or more vectors comprising the recombinant nucleic acid construct may be chimeric, meaning that at least one of its components is heterologous with respect to at least one of its other components.

Plasmid

The one or more vectors can be a plasmid. The plasmid may be useful for transfecting cells with the recombinant nucleic acid construct. The plasmid may be useful for introducing the recombinant nucleic acid construct into the subject. The plasmid may also comprise a regulatory sequence, which may be well suited for gene expression in a cell into which the plasmid is administered.

The plasmid may also comprise a mammalian origin of replication in order to maintain the plasmid extrachromosomally and produce multiple copies of the plasmid in a cell. The plasmid may be pVAX1, pCEP4 or pREP4 from Invitrogen (San Diego, CA), which may comprise the Epstein Barr virus origin of replication and nuclear antigen EBNA-1 coding region, which may produce high copy episomal replication without integration. The backbone of the plasmid may be pAV0242. The plasmid may be a replication defective adenovirus type 5 (Ad5) plasmid.

The plasmid may be pSE420 (Invitrogen, San Diego, Calif.), which may be used for protein production in *Escherichia coli* (*E. coli*). The plasmid may also be pYES2 (Invitrogen, San Diego, Calif.), which may be used for protein production in *Saccharomyces cerevisiae* strains of yeast. The plasmid may also be of the MAXBAC™ complete baculovirus expression system (Invitrogen, San Diego, Calif.), which may be used for protein production in insect cells. The plasmid may also be pcDNAI or pcDNA3 (Invitrogen, San Diego, Calif.), which may be used for protein production in mammalian cells such as Chinese hamster ovary (CHO) cells.

RNA

In one embodiment, the nucleic acid is an RNA molecule. In one embodiment, the RNA molecule is transcribed from a DNA sequence described herein. For example, in some embodiments, the RNA molecule is encoded by a DNA sequence at least 90% homologous to one of SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17 or SEQ ID NO:19, or a variant thereof or a fragment thereof. In another embodiment, the nucleotide sequence comprises an RNA sequence transcribed by a DNA sequence encoding a polypeptide sequence at least 90% homologous to one of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18 or SEQ ID NO:20 or a variant thereof or a fragment thereof. Accordingly, in one embodiment, the invention provides an RNA molecule encoding one or more of the CDV antigens. The RNA may be plus-stranded. Accordingly, in some embodiments, the RNA molecule can be translated by cells without needing any intervening replication steps such as reverse transcription. A RNA molecule useful with the invention may have a 5' cap (e.g. a 7-methylguanosine). This cap can enhance in vivo translation of the RNA. The 5' nucleotide of a RNA molecule useful with the invention may have a 5' triphosphate group. In a capped RNA this may be linked to a 7-methylguanosine via a 5'-to-5' bridge. A RNA molecule may have a 3' poly-A tail. It may also include a poly-A polymerase recognition sequence (e.g. AAUAAA) near its 3' end. A RNA molecule useful with the invention may be single-stranded. A RNA molecule useful with the invention may comprise synthetic RNA. In some embodiments, the RNA molecule is a naked RNA molecule. In one embodiment, the RNA molecule is comprised within a vector.

In one embodiment, the RNA has 5' and 3' UTRs. In one embodiment, the 5' UTR is between zero and 3000 nucleotides in length. The length of 5' and 3' UTR sequences to be added to the coding region can be altered by different methods, including, but not limited to, designing primers for PCR that anneal to different regions of the UTRs. Using this approach, one of ordinary skill in the art can modify the 5' and 3' UTR lengths required to achieve optimal translation efficiency following transfection of the transcribed RNA.

The 5' and 3' UTRs can be the naturally occurring, endogenous 5' and 3' UTRs for the gene of interest. Alternatively, UTR sequences that are not endogenous to the gene of interest can be added by incorporating the UTR sequences into the forward and reverse primers or by any other modifications of the template. The use of UTR sequences that are not endogenous to the gene of interest can be useful for modifying the stability and/or translation efficiency of the RNA. For example, it is known that AU-rich elements in 3' UTR sequences can decrease the stability of RNA. Therefore, 3' UTRs can be selected or designed to increase the stability of the transcribed RNA based on properties of UTRs that are well known in the art.

In one embodiment, the 5' UTR can contain the Kozak sequence of the endogenous gene. Alternatively, when a 5' UTR that is not endogenous to the gene of interest is being added by PCR as described above, a consensus Kozak sequence can be redesigned by adding the 5' UTR sequence. Kozak sequences can increase the efficiency of translation of some RNA transcripts, but does not appear to be required for all RNAs to enable efficient translation. The requirement for Kozak sequences for many RNAs is known in the art. In other embodiments, the 5' UTR can be derived from an RNA virus whose RNA genome is stable in cells. In other embodiments, various nucleotide analogues can be used in the 3' or 5' UTR to impede exonuclease degradation of the RNA.

In one embodiment, the RNA has both a cap on the 5' end and a 3' poly(A) tail which determine ribosome binding, initiation of translation and stability of RNA in the cell.

In one embodiment, the RNA is a nucleoside-modified RNA. Nucleoside-modified RNA have particular advantages over non-modified RNA, including for example, increased stability, low or absent innate immunogenicity, and enhanced translation.

Circular and Linear Vector

The one or more vectors may be circular plasmid, which may transform a target cell by integration into the cellular genome or exist extrachromosomally (e.g., autonomous replicating plasmid with an origin of replication). The vector can be pVAX, pcDNA3.0, or provax, or any other expression vector capable of expressing the heavy chain polypeptide and/or light chain polypeptide encoded by the recombinant nucleic acid construct.

Also provided herein is a linear nucleic acid, or linear expression cassette ("LEC"), that is capable of being efficiently delivered to a subject via electroporation and expressing the heavy chain polypeptide and/or light chain polypeptide encoded by the recombinant nucleic acid construct. The LEC may be any linear DNA devoid of any phosphate backbone. The LEC may not contain any antibiotic resistance genes and/or a phosphate backbone. The LEC may not contain other nucleotide sequences unrelated to the desired gene expression.

The LEC may be derived from any plasmid capable of being linearized. The plasmid may be capable of expressing the heavy chain polypeptide and/or light chain polypeptide encoded by the recombinant nucleic acid construct. The plasmid can be pNP (Puerto Rico/34) or pM2 (New Caledonia/99). The plasmid may be WLV009, pVAX, pcDNA3.0, or provax, or any other expression vector capable of expressing the heavy chain polypeptide and/or light chain polypeptide encoded by the recombinant nucleic acid construct.

The LEC can be perM2. The LEC can be perNP. perNP and perMR can be derived from pNP (Puerto Rico/34) and pM2 (New Caledonia/99), respectively.

7. VIRAL VECTORS

In one embodiment, viral vectors are provided herein which are capable of delivering a nucleic acid of the invention to a cell. The expression vector may be provided to a cell in the form of a viral vector. Viral vector technology is well known in the art and is described, for example, in Sambrook et al. (2001), and in Ausubel et al. (1997), and in other virology and molecular biology manuals. Viruses, which are useful as vectors include, but are not limited to, retroviruses, adenoviruses, adeno-associated viruses, herpes viruses, and lentiviruses. In general, a suitable vector contains an origin of replication functional in at least one organism, a promoter sequence, convenient restriction endonuclease sites, and one or more selectable markers. (See, e.g., WO 01/96584; WO 01/29058; and U.S. Pat. No. 6,326,193. Viral vectors, and especially retroviral vectors, have become the most widely used method for inserting genes into mammalian, e.g., human cells. Other viral vectors can be derived from lentivirus, poxviruses, herpes simplex virus I, adenoviruses and adeno-associated viruses, and the like. See, for example, U.S. Pat. Nos. 5,350,674 and 5,585,362.

8. METHOD OF PREPARING THE VECTOR

Provided herein is a method for preparing the one or more vectors in which the recombinant nucleic acid construct has been placed. After the final subcloning step, the vector can be used to inoculate a cell culture in a large scale fermentation tank, using known methods in the art.

In other embodiments, after the final subcloning step, the vector can be used with one or more electroporation (EP) devices. The EP devices are described below in more detail.

The one or more vectors can be formulated or manufactured using a combination of known devices and techniques, but preferably they are manufactured using a plasmid manufacturing technique that is described in a licensed, copending U.S. provisional application U.S. Ser. No. 60/939,792, which was filed on May 23, 2007. In some examples, the DNA plasmids described herein can be formulated at concentrations greater than or equal to 10 mg/mL. The manufacturing techniques also include or incorporate various devices and protocols that are commonly known to those of ordinary skill in the art, in addition to those described in U.S. Ser. No. 60/939,792, including those described in a licensed patent, U.S. Pat. No. 7,238,522, which issued on Jul. 3, 2007. The above-referenced application and patent, U.S. Ser. No. 60/939,792 and U.S. Pat. No. 7,238,522, respectively, are hereby incorporated in their entirety.

9. METHODS

Provided herein are methods of treating, protecting against, and/or preventing a CDV associated disease in a subject in need thereof by administering one or more immunogenic composition described herein to the subject. Administration of the immunogenic composition to the subject can induce or elicit an immune response in the subject. The induced immune response can be used to treat, prevent, and/or protect against disease, for example, CDV infection or a disease or disorder associated with CDV infection.

Provided herein is a method for delivering the immunogenic composition for providing genetic constructs and proteins of the CDV antigen which comprise epitopes that make them particular effective against CDV, against which an immune response can be induced. The method of delivering the immunogenic composition or vaccination may be provided to induce a therapeutic and prophylactic immune response. The vaccination process may generate in the mammal an immune response against CDV. The immunogenic composition may be delivered to an individual to modulate the activity of the mammal's immune system and enhance the immune response. The delivery of the immunogenic composition may be the transfection of the CDV antigen as a nucleic acid molecule that is expressed in the cell and delivered to the surface of the cell upon which the immune system recognized and induces a cellular, humoral, or cellular and humoral response. The delivery of the immunogenic composition may be used to induce or elicit and immune response in mammals against CDV by administering to the mammals the immunogenic composition as discussed above.

Upon delivery of the immunogenic composition and plasmid into the cells of the mammal, the transfected cells will express and secrete CDV antigens for each of the plasmids injected from the immunogenic composition. These proteins will be recognized as foreign by the immune system and antibodies will be made against them. These antibodies will be maintained by the immune system and allow for an effective response to subsequent infections by CDV.

The immunogenic composition may be administered to a mammal to elicit an immune response in a mammal. The mammal may be a member of a family in the order Carnivora (e.g. Canidae, Ailuridae, Mustelidae, Procyonidae, Hyaenidae, Ursidae, Viverridae, and Felidae), a Tayassuidae (e.g., a peccary or javelina), a marine mammal, or a mammal that is susceptible to CDV.

The induced immune response can include an induced humoral immune response and/or an induced cellular immune response. The humoral immune response can be induced by about 1.5-fold to about 16-fold, about 2-fold to about 12-fold, or about 3-fold to about 10-fold. The induced cellular immune response can include a CD8+ T cell response, which is induced by about 2-fold to about 30-fold, about 3-fold to about 25-fold, or about 4-fold to about 20-fold.

The immunogenic composition dose can be between 1 μg to 10 mg active component/kg body weight/time, and can be 20 μg to 10 mg component/kg body weight/time. The immunogenic composition can be administered every 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, or 31 days. The number of immunogenic composition doses for effective treatment can be 1, 2, 3, 4, 5, 6, 7, 8, 9, or 10.

The immunogenic composition can be formulated in accordance with standard techniques well known to those skilled in the pharmaceutical art. Such compositions can be administered in dosages and by techniques well known to those skilled in the medical arts taking into consideration such factors as the age, sex, weight, and condition of the particular subject, and the route of administration.

The immunogenic composition can be administered prophylactically or therapeutically. In prophylactic administration, the immunogenic compositions can be administered in an amount sufficient to induce an immune response. In therapeutic applications, the immunogenic compositions are administered to a subject in need thereof in an amount sufficient to elicit a therapeutic effect. An amount adequate to accomplish this is defined as "therapeutically effective dose." Amounts effective for this use will depend on, e.g., the particular composition of the immunogenic composition regimen administered, the manner of administration, the stage and severity of the disease, the general state of health of the subject, and the judgment of the prescribing physician.

The immunogenic composition can be administered by methods well known in the art as described in Donnelly et al. (Ann. Rev. Immunol. 15:617-648 (1997)); Felgner et al. (U.S. Pat. No. 5,580,859, issued Dec. 3, 1996); Felgner (U.S. Pat. No. 5,703,055, issued Dec. 30, 1997); and Carson et al. (U.S. Pat. No. 5,679,647, issued Oct. 21, 1997), the contents of all of which are incorporated herein by reference in their entirety. The DNA of the immunogenic composition can be complexed to particles or beads that can be administered to an individual, for example, using a vaccine gun. One skilled in the art would know that the choice of a pharmaceutically acceptable carrier, including a physiologically acceptable compound, depends, for example, on the route of administration of the expression vector.

The immunogenic composition can be delivered via a variety of routes. Typical delivery routes include parenteral administration, e.g., intradermal, intramuscular or subcutaneous delivery. Other routes include oral administration, intranasal, and intravaginal routes. For the DNA of the immunogenic composition in particular, the immunogenic composition can be delivered to the interstitial spaces of tissues of an individual (Felgner et al., U.S. Pat. Nos. 5,580,859 and 5,703,055, the contents of all of which are incorporated herein by reference in their entirety). The immunogenic composition can also be administered to muscle, or can be administered via intradermal or subcutaneous injections, or transdermally, such as by iontophoresis. Epidermal administration of the immunogenic composition can also be employed. Epidermal administration can involve mechanically or chemically irritating the outermost layer of epidermis to stimulate an immune response to the irritant (Carson et al., U.S. Pat. No. 5,679,647, the contents of which are incorporated herein by reference in its entirety).

The immunogenic composition can also be formulated for administration via the nasal passages. Formulations suitable for nasal administration, wherein the carrier is a solid, can include a coarse powder having a particle size, for example, in the range of about 10 to about 500 microns which is administered in the manner in which snuff is taken, i.e., by rapid inhalation through the nasal passage from a container of the powder held close up to the nose. The formulation can be a nasal spray, nasal drops, or by aerosol administration by nebulizer. The formulation can include aqueous or oily solutions of the immunogenic composition.

The immunogenic composition can be a liquid preparation such as a suspension, syrup or elixir. The immunogenic composition can also be a preparation for parenteral, subcutaneous, intradermal, intramuscular or intravenous administration (e.g., injectable administration), such as a sterile suspension or emulsion.

The immunogenic composition can be incorporated into liposomes, microspheres or other polymer matrices (Felgner et al., U.S. Pat. No. 5,703,055; Gregoriadis, Liposome Technology, Vols. I to III (2nd ed. 1993), the contents of which are incorporated herein by reference in their entirety). Liposomes can consist of phospholipids or other lipids, and can be nontoxic, physiologically acceptable and metabolizable carriers that are relatively simple to make and administer.

The immunogenic composition may be administered by different routes including orally, parenterally, sublingually, transdermally, rectally, transmucosally, topically, via inhalation, via buccal administration, intrapleurally, intravenous, intraarterial, intraperitoneal, subcutaneous, intramuscular, intranasal, intrathecal, and intraarticular or combinations thereof. For veterinary use, the composition may be administered as a suitably acceptable formulation in accordance with normal veterinary practice. The veterinarian can readily determine the dosing regimen and route of administration that is most appropriate for a particular animal. The immunogenic composition may be administered by traditional syringes, needleless injection devices, "microprojectile bombardment gone guns", or other physical methods such as electroporation ("EP"), "hydrodynamic method", or ultrasound.

The plasmid of the immunogenic composition may be delivered to the mammal by several well-known technologies including DNA injection (also referred to as DNA vaccination) with and without in vivo electroporation, liposome mediated, nanoparticle facilitated, recombinant vectors such as recombinant adenovirus, recombinant adenovirus associated virus and recombinant vaccinia. The CDV antigen may be delivered via DNA injection and along with in vivo electroporation.

10. ELECTROPORATION

Administration of the immunogenic composition via electroporation may be accomplished using electroporation devices that can be configured to deliver to a desired tissue of a mammal a pulse of energy effective to cause reversible pores to form in cell membranes, and preferable the pulse of energy is a constant current similar to a preset current input by a user. The electroporation device may comprise an electroporation component and an electrode assembly or handle assembly. The electroporation component may include and incorporate one or more of the various elements of the electroporation devices, including: controller, current waveform generator, impedance tester, waveform logger, input element, status reporting element, communication port, memory component, power source, and power switch. The electroporation may be accomplished using an in vivo electroporation device, for example CELLECTRA EP system (Inovio Pharmaceuticals, Plymouth Meeting, PA) or Elgen electroporator (Inovio Pharmaceuticals, Plymouth Meeting, PA) to facilitate transfection of cells by the plasmid.

The electroporation component may function as one element of the electroporation devices, and the other elements are separate elements (or components) in communication with the electroporation component. The electroporation component may function as more than one element of the electroporation devices, which may be in communication with still other elements of the electroporation devices separate from the electroporation component. The elements of the electroporation devices existing as parts of one electromechanical or mechanical device may not limited as the elements can function as one device or as separate elements in communication with one another. The electroporation component may be capable of delivering the pulse of energy that produces the constant current in the desired tissue, and includes a feedback mechanism. The electrode assembly may include an electrode array having a plurality of electrodes in a spatial arrangement, wherein the electrode assembly receives the pulse of energy from the electroporation component and delivers same to the desired tissue through the electrodes. At least one of the plurality of electrodes is neutral during delivery of the pulse of energy and measures impedance in the desired tissue and communicates the impedance to the electroporation component. The feedback mechanism may receive the measured impedance and can adjust the pulse of energy delivered by the electroporation component to maintain the constant current.

A plurality of electrodes may deliver the pulse of energy in a decentralized pattern. The plurality of electrodes may deliver the pulse of energy in the decentralized pattern through the control of the electrodes under a programmed sequence, and the programmed sequence is input by a user to the electroporation component. The programmed sequence may comprise a plurality of pulses delivered in sequence, wherein each pulse of the plurality of pulses is delivered by at least two active electrodes with one neutral electrode that measures impedance, and wherein a subsequent pulse of the plurality of pulses is delivered by a different one of at least two active electrodes with one neutral electrode that measures impedance.

The feedback mechanism may be performed by either hardware or software. The feedback mechanism may be performed by an analog closed-loop circuit. The feedback occurs every 50 μs, 20 μs, 10 μs or 1 μs, but is preferably a real-time feedback or instantaneous (i.e., substantially instantaneous as determined by available techniques for determining response time). The neutral electrode may measure the impedance in the desired tissue and communicates the impedance to the feedback mechanism, and the feedback mechanism responds to the impedance and adjusts the pulse of energy to maintain the constant current at a value similar to the preset current. The feedback mechanism may maintain the constant current continuously and instantaneously during the delivery of the pulse of energy.

Examples of electroporation devices and electroporation methods that may facilitate delivery of the immunogenic compositions of the present invention, include those described in U.S. Pat. No. 7,245,963 by Draghia-Akli, et al., U.S. Patent Pub. 2005/0052630 submitted by Smith, et al., the contents of which are hereby incorporated by reference in their entirety. Other electroporation devices and electroporation methods that may be used for facilitating delivery of the immunogenic compositions include those provided in co-pending and co-owned U.S. patent application Ser. No. 11/874,072, filed Oct. 17, 2007, which claims the benefit under 35 USC 119(e) to U.S. Provisional Application Ser. No. 60/852,149, filed Oct. 17, 2006, and 60/978,982, filed Oct. 10, 2007, all of which are hereby incorporated in their entirety.

U.S. Pat. No. 7,245,963 by Draghia-Akli, et al. describes modular electrode systems and their use for facilitating the introduction of a biomolecule into cells of a selected tissue in a body or plant. The modular electrode systems may comprise a plurality of needle electrodes; a hypodermic needle; an electrical connector that provides a conductive link from a programmable constant-current pulse controller to the plurality of needle electrodes; and a power source. An operator can grasp the plurality of needle electrodes that are mounted on a support structure and firmly insert them into the selected tissue in a body or plant. The biomolecules are then delivered via the hypodermic needle into the selected tissue. The programmable constant-current pulse controller is activated and constant-current electrical pulse is applied to the plurality of needle electrodes. The applied constant-current electrical pulse facilitates the introduction of the biomolecule into the cell between the plurality of electrodes. The entire content of U.S. Pat. No. 7,245,963 is hereby incorporated by reference.

U.S. Patent Pub. 2005/0052630 submitted by Smith, et al. describes an electroporation device which may be used to effectively facilitate the introduction of a biomolecule into cells of a selected tissue in a body or plant. The electroporation device comprises an electro-kinetic device ("EKD device") whose operation is specified by software or firmware. The EKD device produces a series of programmable constant-current pulse patterns between electrodes in an array based on user control and input of the pulse parameters, and allows the storage and acquisition of current waveform data. The electroporation device also comprises a replaceable electrode disk having an array of needle electrodes, a central injection channel for an injection needle, and a removable guide disk. The entire content of U.S. Patent Pub. 2005/0052630 is hereby incorporated by reference.

The electrode arrays and methods described in U.S. Pat. No. 7,245,963 and U.S. Patent Pub. 2005/0052630 may be adapted for deep penetration into not only tissues such as muscle, but also other tissues or organs. Because of the configuration of the electrode array, the injection needle (to deliver the biomolecule of choice) is also inserted completely into the target organ, and the injection is administered perpendicular to the target issue, in the area that is pre-delineated by the electrodes The electrodes described in U.S. Pat. No. 7,245,963 and U.S. Patent Pub. 2005/005263 are preferably 20 mm long and 21 gauge.

Additionally, contemplated in some embodiments that incorporate electroporation devices and uses thereof, there are electroporation devices that are those described in the following patents: U.S. Pat. No. 5,273,525 issued Dec. 28, 1993, U.S. Pat. No. 6,110,161 issued Aug. 29, 2000, U.S. Pat. No. 6,261,281 issued Jul. 17, 2001, and U.S. Pat. No. 6,958,060 issued Oct. 25, 2005, and U.S. Pat. No. 6,939,862 issued Sep. 6, 2005. Furthermore, patents covering subject matter provided in U.S. Pat. No. 6,697,669 issued Feb. 24, 2004, which concerns delivery of DNA using any of a variety of devices, and U.S. Pat. No. 7,328,064 issued Feb. 5, 2008, drawn to method of injecting DNA are contemplated herein. The above-patents are incorporated by reference in their entirety.

11. GENERATION OF ANTIGENS IN VITRO AND EX VIVO

In one embodiment, the optimized CDV antigen is generated in vitro or ex vivo. For example, in one embodiment, a nucleic acid encoding an optimized CDV antigen can be introduced and expressed in an in vitro or ex vivo cell.

Methods of introducing and expressing genes into a cell are known in the art. In the context of an expression vector, the vector can be readily introduced into a host cell, e.g., mammalian, bacterial, yeast, or insect cell by any method in the art. For example, the expression vector can be transferred into a host cell by physical, chemical, or biological means.

Physical methods for introducing a polynucleotide into a host cell include calcium phosphate precipitation, lipofection, particle bombardment, microinjection, electroporation, and the like. Methods for producing cells comprising vectors and/or exogenous nucleic acids are well-known in the art. See, for example, Sambrook et al. (2012, Molecular Cloning: A Laboratory Manual, Cold Spring Harbor Laboratory, New York). A preferred method for the introduction of a polynucleotide into a host cell is calcium phosphate transfection.

Biological methods for introducing a polynucleotide of interest into a host cell include the use of DNA and RNA vectors. Viral vectors, and especially retroviral vectors, have become the most widely used method for inserting genes into mammalian, e.g., human cells. Other viral vectors can be derived from lentivirus, poxviruses, herpes simplex virus I, adenoviruses and adeno-associated viruses, and the like. See, for example, U.S. Pat. Nos. 5,350,674 and 5,585,362.

Chemical means for introducing a polynucleotide into a host cell include colloidal dispersion systems, such as macromolecule complexes, nanocapsules, microspheres, beads, and lipid-based systems including oil-in-water emulsions, micelles, mixed micelles, and liposomes. An exemplary colloidal system for use as a delivery vehicle in vitro and in vivo is a liposome (e.g., an artificial membrane vesicle).

In the case where a non-viral delivery system is utilized, an exemplary delivery vehicle is a liposome. The use of lipid formulations is contemplated for the introduction of the nucleic acids into a host cell (in vitro, ex vivo or in vivo). In another aspect, the nucleic acid may be associated with a lipid. The nucleic acid associated with a lipid may be encapsulated in the aqueous interior of a liposome, interspersed within the lipid bilayer of a liposome, attached to a liposome via a linking molecule that is associated with both the liposome and the oligonucleotide, entrapped in a liposome, complexed with a liposome, dispersed in a solution containing a lipid, mixed with a lipid, combined with a lipid, contained as a suspension in a lipid, contained or complexed with a micelle, or otherwise associated with a lipid. Lipid, lipid/DNA or lipid/expression vector associated compositions are not limited to any particular structure in solution. For example, they may be present in a bilayer structure, as micelles, or with a "collapsed" structure. They may also simply be interspersed in a solution, possibly forming aggregates that are not uniform in size or shape. Lipids are fatty substances which may be naturally occurring or synthetic lipids. For example, lipids include the fatty droplets that naturally occur in the cytoplasm as well as the class of compounds which contain long-chain aliphatic hydrocarbons and their derivatives, such as fatty acids, alcohols, amines, amino alcohols, and aldehydes.

12. METHOD OF PREPARING THE VACCINE

Provided herein are methods for preparing the DNA plasmids that comprise the vaccines discussed herein. The DNA plasmids, after the final subcloning step into the mammalian expression plasmid, can be used to inoculate a cell culture in a large-scale fermentation tank, using known methods in the art.

The DNA plasmids for use with the EP devices of the present invention can be formulated or manufactured using a combination of known devices and techniques, but preferably they are manufactured using an optimized plasmid manufacturing technique that is described in a US published application no. 20090004716, which was filed on May 23, 2007. In some examples, the DNA plasmids used in these studies can be formulated at concentrations greater than or equal to 10 mg/mL. The manufacturing techniques also include or incorporate various devices and protocols that are commonly known to those of ordinary skill in the art, in addition to those described in U.S. Ser. No. 60/939,792, including those described in a licensed patent, U.S. Pat. No. 7,238,522, which issued on Jul. 3, 2007. The above-referenced application and patent, U.S. Ser. No. 60/939,792 and U.S. Pat. No. 7,238,522, respectively, are hereby incorporated in their entirety.

The present invention has multiple aspects, illustrated by the following non-limiting examples.

13. EXAMPLES

Example 1: Development of a DNA Vaccine for Canine Distemper Virus

Figure 1B:
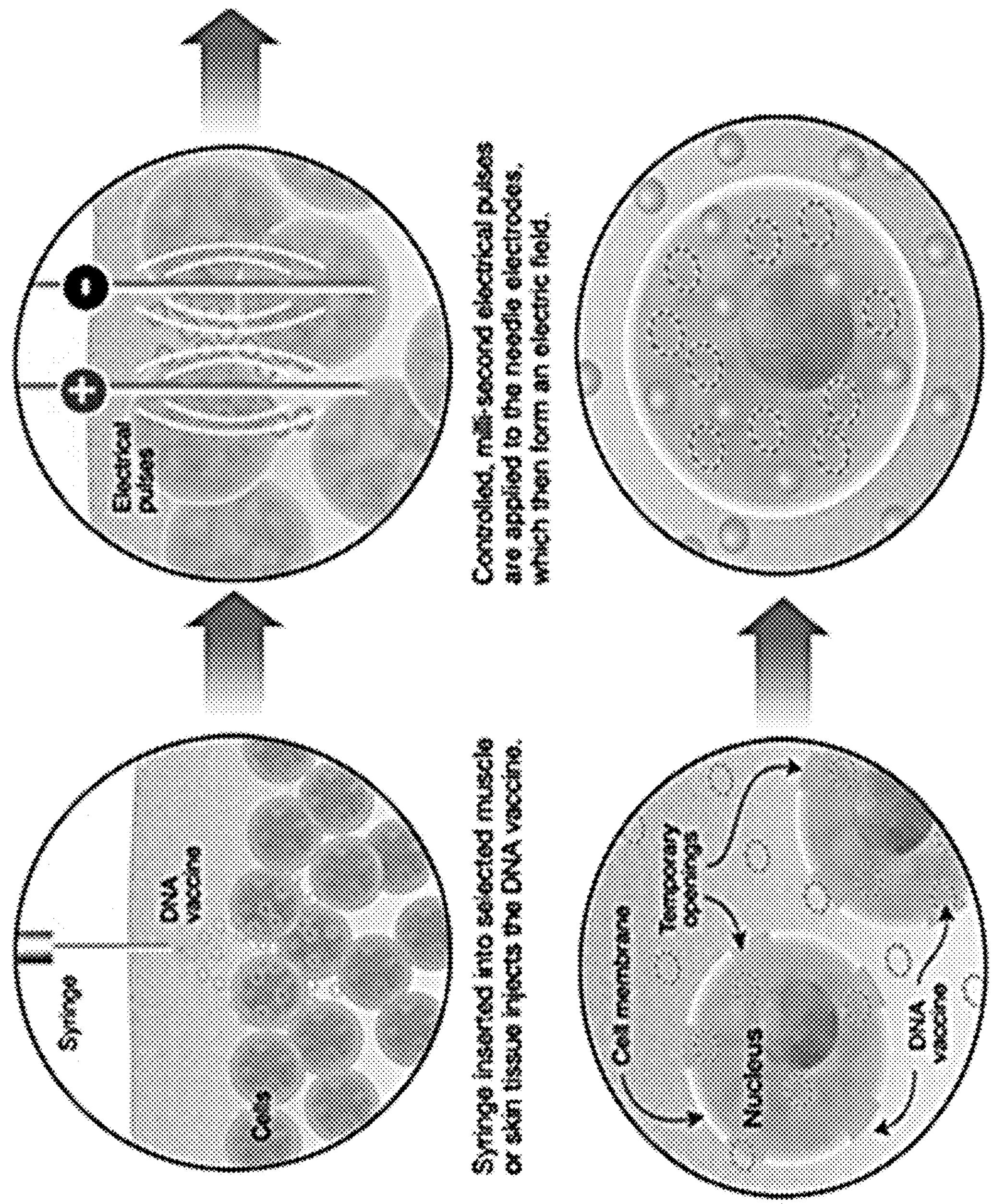
Figure 1B:
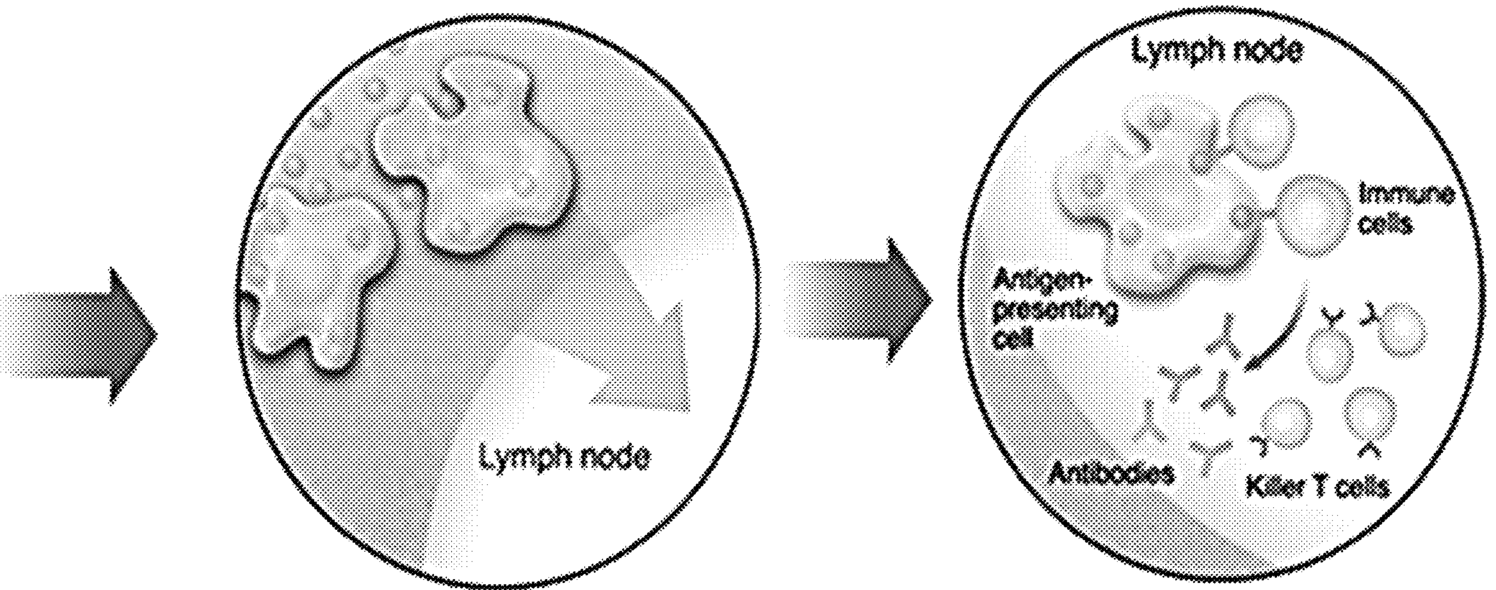
Figure 2:
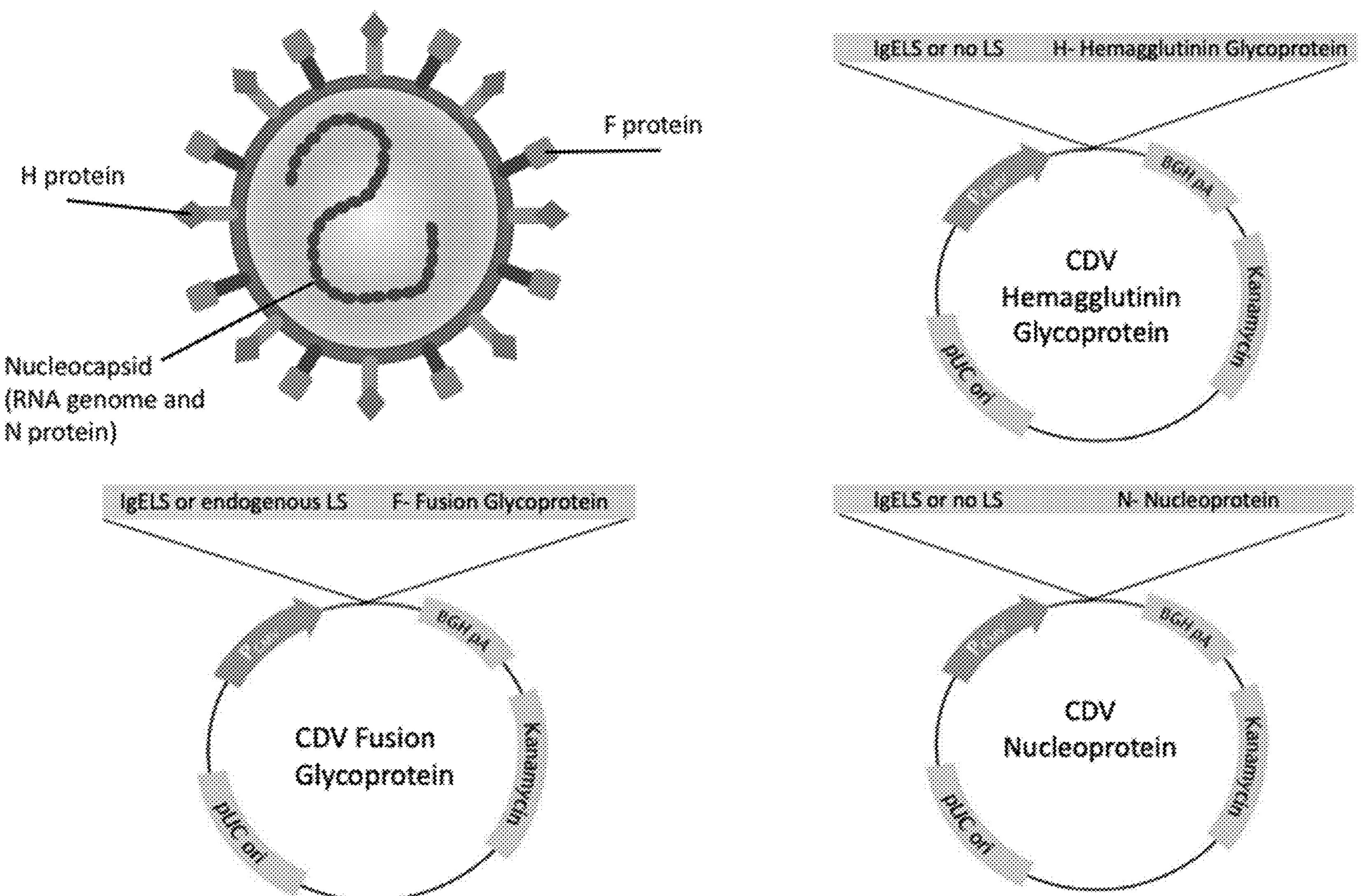
FIG. 2 depicts a diagram of the CDV antigens that were used in the experiments and the plasmid designs for DNA vaccination.
Figures 3A, 3B:
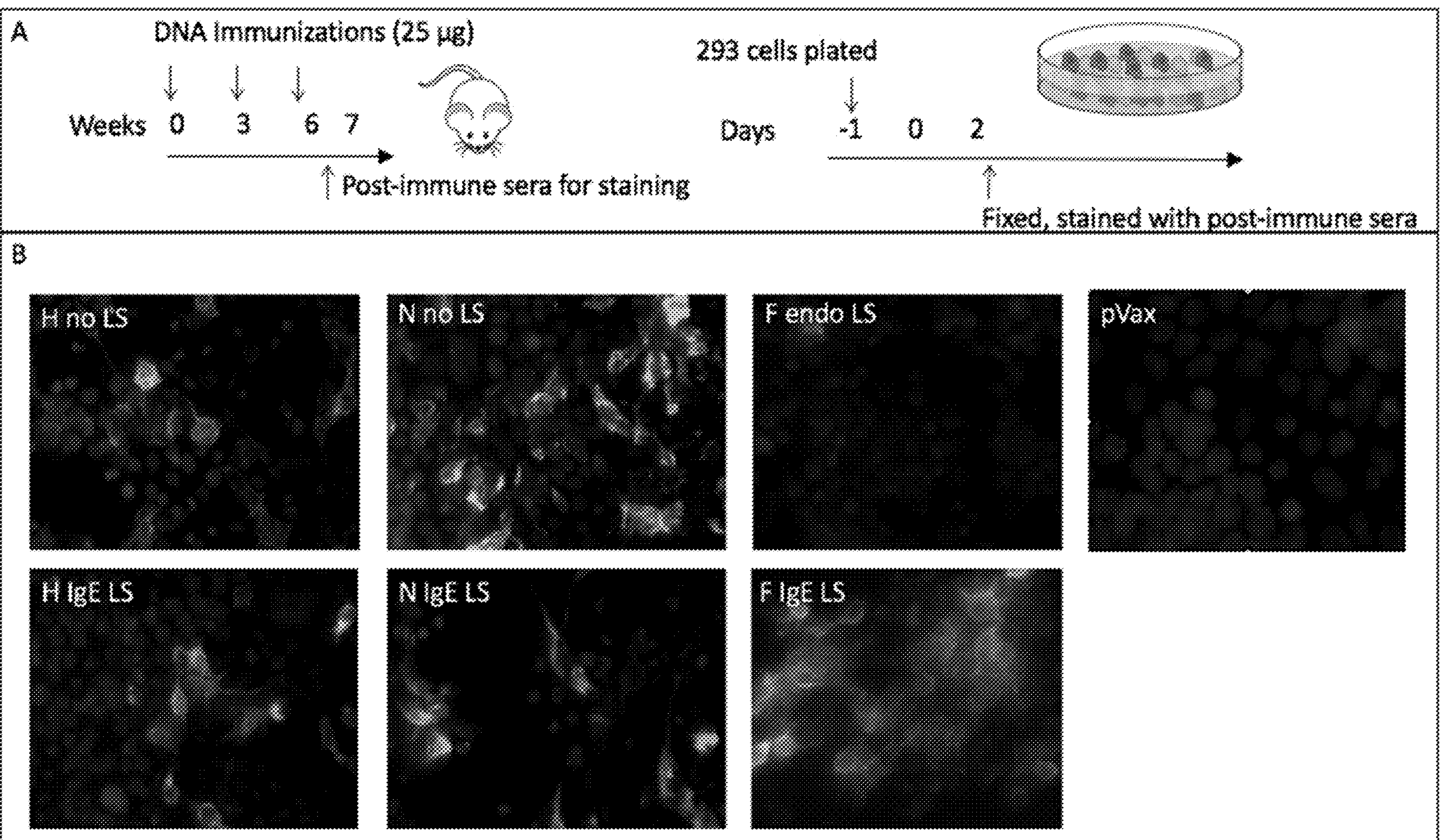
FIG. 3A and FIG. 3B, depicts exemplary experimental results demonstrating that there was a high level of expression of CDV antigens in cells after transfection.
Figure 4:
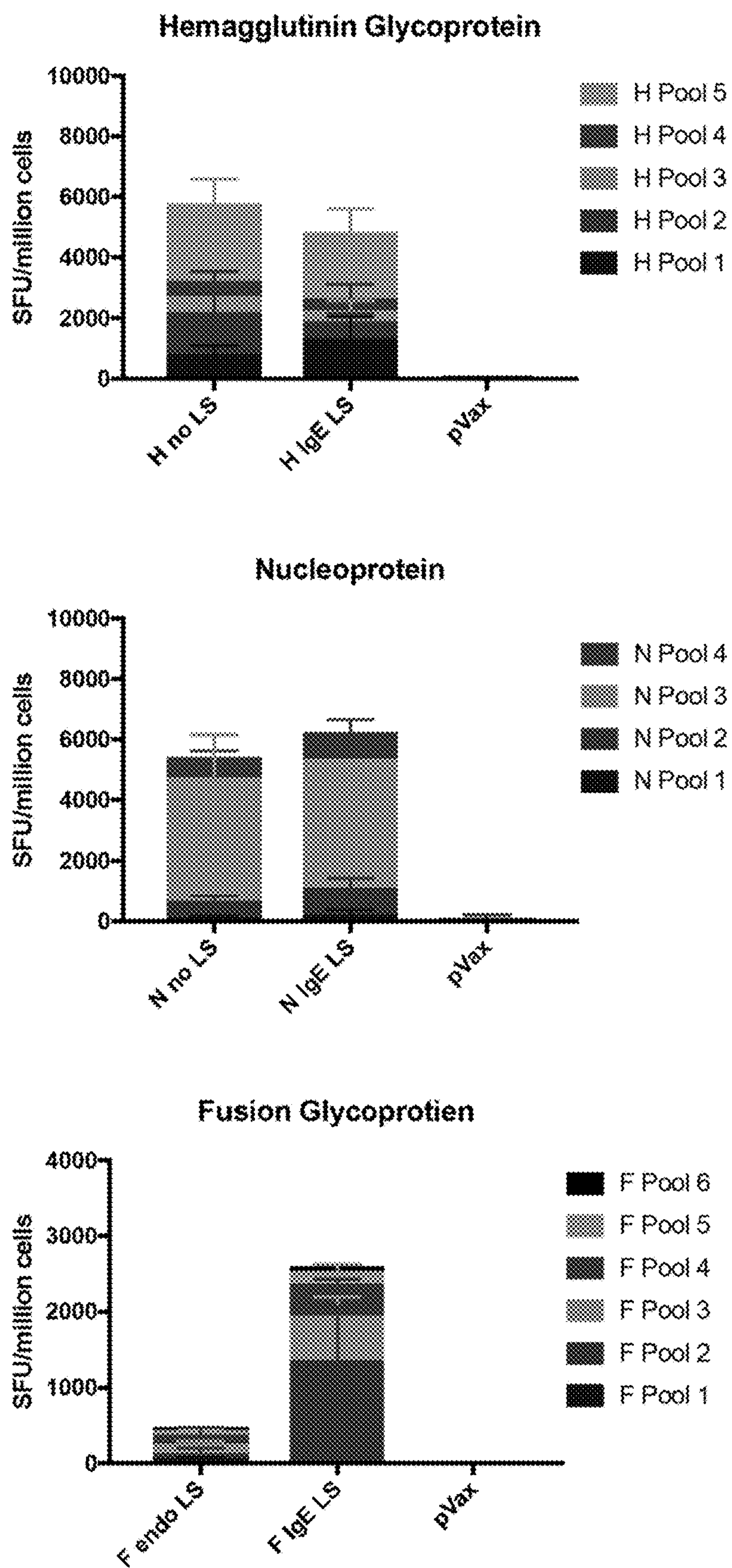
FIG. 4 depicts exemplary experimental results demonstrating that CDV antigens are immunogenic in mice.
Figure 5:
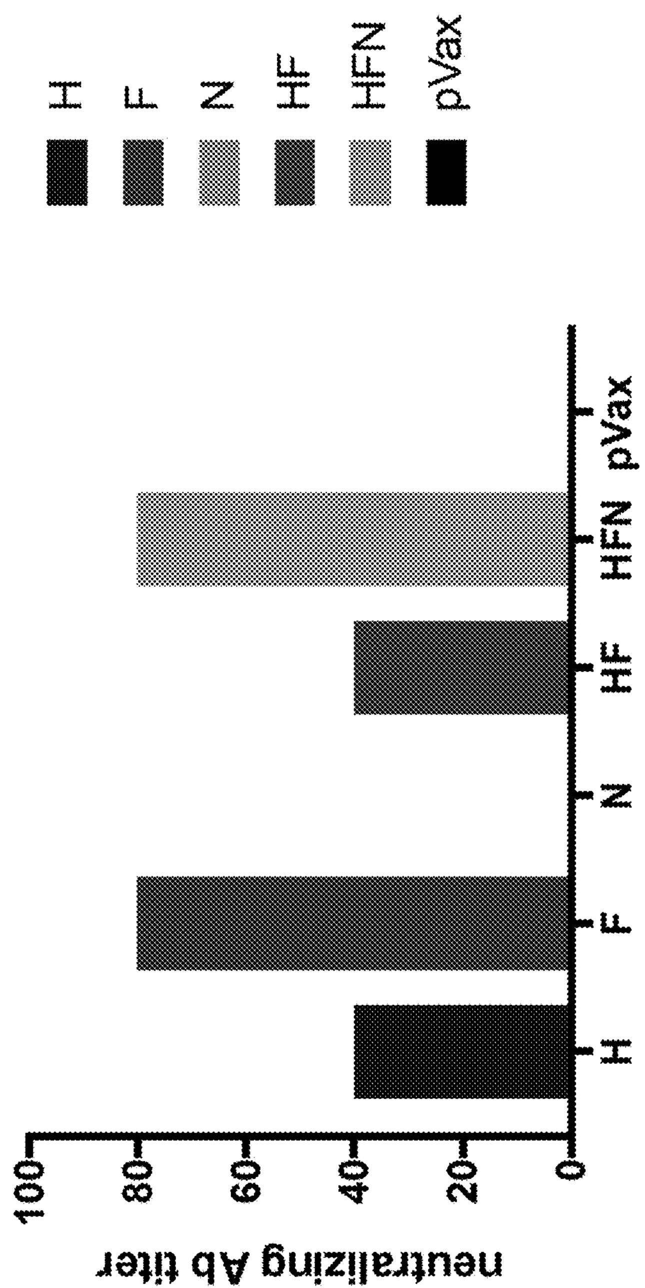
FIG. 5 depicts exemplary experimental results demonstrating that CDV antigens induce neutralizing antibodies.

The goal of this project was to develop an optimized DNA vaccine to provide protection against CDV through induction of an antibody response as well as cell mediated immunity (FIG. 1). Constructs were developed for H, F and N antigens (FIG. 2) and in vitro expression was demonstrated (FIG. 3). Animals were immunized with the constructs, separately and in combination and studied for immune induction. Serum was collected after each immunization and animals were immunized and tissues harvested for immune analysis one week after the final immunization. ELISPOTs and flow cytometry were used to assess the cell mediated immunity elicited by vaccination with anti-CDV constructs (FIG. 4). Microscopy and ELISAs were used to assess antibodies elicited against the H, F, and N constructs. A neutralization test against rCDV$^{RI}$ expressing Venus fluorescent protein (dose: 100 TCID50/well) was performed with sera collected from mice following several doses of the indicated vaccine formulations. Immunization with F alone or with HFN resulted in the highest neutralization, followed by immunization with H alone or with HF. Immunization with N alone did not results in neutralizing antibodies (FIG. 5).

The data presented herein show that a novel synthetic DNA CDV vaccine elicits both a humoral and a cell-mediated immune response against multiple CDV antigens. Further, it is demonstrated that one or two immunizations was sufficient to elicit anti CDV immunity. Functional immune responses are described. The data suggests that a DNA vaccine against Canine Distemper Virus provides a new alternative safe and potent vaccine to protect against Canine Distemper in high risk populations in zoo and conservation settings, as well as possibly in domestic dogs.

SEQ ID NO:1, Consensus H antigen

SEQ ID NO:2, Consensus H antigen

SEQ ID NO:3, Consensus H antigen operably linked to an IgE leader sequence

SEQ ID NO:4, Consensus H antigen operably linked to an IgE leader sequence

SEQ ID NO:5, Optimized H IgE leader sequence

SEQ ID NO:6, Optimized H IgE leader sequence

SEQ ID NO:7, Consensus N antigen, no leader sequence

SEQ ID NO:8, Consensus_N_antigen, no leader sequence

SEQ ID NO:9, Consensus N antigen operably linked to IgE leader sequence

SEQ ID NO:10, Consensus N antigen operably linked to IgE leader sequence

SEQ ID NO:11, Optimized N IgE leader sequence

SEQ ID NO:12, Optimized N IgE leader sequence

SEQ ID NO:13, Consensus F antigen

SEQ ID NO:14, Consensus F antigen

SEQ ID NO:15, Consensus F antigen operably linked to endo leader sequence

SEQ ID NO:16, Consensus F antigen operably linked to endo leader sequence

SEQ ID NO:17, Consensus F antigen operably linked to IgE leader sequence

SEQ ID NO:18, Consensus F antigen operably linked to IgE leader sequence

SEQ ID NO:19, Optimized F with IgE leader sequence

SEQ ID NO:20, Optimized F with IgE leader sequence

SEQ ID NO:21, immunoglobulin E (IgE) leader, amino acid sequence

What is claimed is:

1. An immunogenic composition comprising a nucleic acid molecule encoding at least one Canine Distemper Virus (CDV) antigen, wherein the nucleic acid molecule encodes a peptide comprising an amino acid sequence selected from the group consisting of a) an amino acid sequence having at least 99% identity over an entire length of the amino acid sequence selected from the group consisting of SEQ ID NO:2, SEQ ID NO:4, SEQ ID NO: 6, SEQ ID NO:8, SEQ ID NO: 10, SEQ ID NO: 12, SEQ ID NO: 14, SEQ ID NO: 16, SEQ ID NO: 18 and SEQ ID NO:20, and b) the amino acid sequence selected from the group consisting of SEQ ID NO:2, SEQ ID NO: 4, SEQ ID NO:6, SEQ ID NO:8, SEQ ID NO: 10, SEQ ID NO: 12, SEQ ID NO: 14, SEQ ID NO: 16, SEQ ID NO: 18 and SEQ ID NO:20.

2. The immunogenic composition of claim 1, wherein the nucleic acid molecule is selected from the group consisting of a DNA molecule and a RNA molecule.

3. The immunogenic composition of claim 1, wherein the nucleic acid molecule comprises a nucleotide sequence selected from the group consisting of a) a nucleotide sequence having at least 90% identity over an entire length of a nucleotide sequence selected from the group consisting of SEQ ID NO:1, SEQ ID NO:3, SEQ ID NO:5, SEQ ID NO:7, SEQ ID NO:9, SEQ ID NO:11, SEQ ID NO:13, SEQ ID NO: 15, SEQ ID NO:17 and SEQ ID NO:19, b) an immunogenic fragment selected from the group consisting of a fragment or variant of SEQ ID NO: 1 that encodes over at least 60% of the amino acid sequence at least 99% identical to SEQ ID NO:2, a fragment or variant of SEQ ID NO:3 that encodes over at least 60% of the amino acid sequence at least 99% identical to SEQ ID NO:4, a fragment or variant of SEQ ID NO: 5 that encodes over at least 60% of the amino acid sequence at least 99% identical to SEQ ID NO:6, a fragment or variant of SEQ ID NO:7 that encodes over at least 60% of the amino acid sequence at least 99% identical to SEQ ID NO:8, a fragment or variant of SEQ ID NO: 9 that encodes over at least 60% of the amino acid sequence at least 99% identical to SEQ ID NO: 10, a fragment or variant of SEQ ID NO:11 that encodes over at least 60% of the amino acid sequence at least 99% identical to SEQ ID NO:12, a fragment or variant of SEQ ID NO:13 that encodes over at least 60% of the amino acid sequence at least 99% identical to SEQ ID NO: 14, a fragment or variant of SEQ ID NO: 15 that encodes over at least 60% of the amino acid sequence at least 99% identical to SEQ ID NO: 16, a fragment or variant of SEQ ID NO:17 that encodes over at least 60% of the amino acid sequence at least 99% identical to SEQ ID NO:18 and a fragment or variant of SEQ ID NO: 19 that encodes over at least 60% of the amino acid sequence at least 99% identical to SEQ ID NO:20, c) a nucleotide sequence selected from the group consisting of SEQ ID NO:1, SEQ ID NO: 3, SEQ ID NO:5, SEQ ID NO:7, SEQ ID NO:9, SEQ ID NO: 11, SEQ ID NO: 13, SEQ ID NO: 15, SEQ ID NO:17 and SEQ ID NO:19, and d) an immunogenic fragment of a nucleotide sequence selected from the group consisting of a fragment of SEQ ID NO: 1 that encodes at least 60% of SEQ ID NO:2, a fragment or variant of SEQ ID NO:3 that encodes over at least 60% of the amino acid sequence at least 99% identical to SEQ ID NO:4, a fragment or variant of SEQ ID NO:5 that encodes over at least 60% of the amino acid sequence at least 99% identical to SEQ ID NO:6, a fragment or variant of SEQ ID NO: 7 that encodes over at least 60% of the amino acid sequence at least 99% identical to SEQ ID NO:8, a fragment or variant of SEQ ID NO:9 that encodes over at least 60% of the amino acid sequence at least 99% identical to SEQ ID NO:10, a fragment or variant of SEQ ID NO: 11 that encodes over at least 60% of the amino acid sequence at least 99% identical to SEQ ID NO: 12, a fragment or variant of SEQ ID NO:13 that encodes over at least 60% of the amino acid sequence at least 99% identical to SEQ ID NO:14, a fragment or variant of SEQ ID NO:15 that encodes over at least 60% of the amino acid sequence at least 99% identical to SEQ ID NO: 16, a fragment or variant of SEQ ID NO:17 that encodes over at least 60% of the amino acid sequence at least 99% identical to SEQ ID NO:18 and a fragment or variant of SEQ ID NO:19 that encodes over at least 60% of the amino acid sequence at least 99% identical to SEQ ID NO: 20.

4. The immunogenic composition of claim 1, wherein the nucleic acid molecule comprises an expression vector.

5. The immunogenic composition of claim 1, wherein the nucleic acid molecule is incorporated into a viral particle.

6. The immunogenic composition of claim 1, further comprising a pharmaceutically acceptable excipient.

7. The immunogenic composition of claim 1, further comprising an adjuvant.

8. A nucleic acid molecule encoding a peptide comprising an amino acid sequence selected from the group consisting of a) an amino acid sequence having at least 99% identity over an entire length of the amino acid sequence selected from the group consisting of SEQ ID NO:2, SEQ ID NO:4, SEQ ID NO: 6, SEQ ID NO:8, SEQ ID NO: 10, SEQ ID NO: 12, SEQ ID NO: 14, SEQ ID NO: 16, SEQ ID NO: 18 and SEQ ID NO:20, and b) the amino acid sequence selected from the group consisting of SEQ ID NO:2, SEQ ID NO: 4, SEQ ID NO:6, SEQ ID NO:8, SEQ ID NO: 10, SEQ ID NO: 12, SEQ ID NO: 14, SEQ ID NO: 16, SEQ ID NO: 18 and SEQ ID NO:20.

9. The nucleic acid molecule of claim 8, wherein the nucleic acid molecule is selected from the group consisting of a DNA molecule and an RNA molecule.

10. The nucleic acid molecule of claim 8, wherein the nucleic acid molecule comprises a nucleotide sequence selected from the group consisting of a) a nucleotide sequence having at least 90% identity over an entire length of a nucleotide sequence selected from the group consisting of SEQ ID NO:1, SEQ ID NO:3, SEQ ID NO:5, SEQ ID NO:7, SEQ ID NO:9, SEQ ID NO: 11, SEQ ID NO: 13, SEQ ID NO: 15, SEQ ID NO:17 and SEQ ID NO:19, b) an immunogenic fragment selected from the group consisting of a fragment or variant of SEQ ID NO: 1 that encodes over at least 60% of the amino acid sequence at least 99% identical to SEQ ID NO:2, a fragment or variant of SEQ ID NO:3 that encodes over at least 60% of the amino acid sequence at least 99% identical to SEQ ID NO:4, a fragment or variant of SEQ ID NO: 5 that encodes over at least 60% of the amino acid sequence at least 99% identical to SEQ ID NO:6, a fragment or variant of SEQ ID NO:7 that encodes over at least 60% of the amino acid sequence at least 99% identical to SEQ ID NO:8, a fragment or variant of SEQ ID NO: 9 that encodes over at least 60% of the amino acid sequence at least 99% identical to SEQ ID NO: 10, a fragment or variant of SEQ ID NO:11 that encodes over at least 60% of the amino acid sequence at least 99% identical to SEQ ID NO:12, a fragment or variant of SEQ ID NO:13 that encodes over at least 60% of the amino acid sequence at least 99% identical to SEQ ID NO: 14, a fragment or variant of SEQ ID NO: 15 that encodes over at least 60% of the amino acid sequence at least 99% identical to SEQ ID NO: 16, a fragment or variant of SEQ ID NO:17 that encodes over at least 60% of the amino acid sequence at least 99% identical to SEQ ID NO:18 and a fragment or variant of SEQ ID NO:19 that encodes over at least 60% of the amino acid sequence at least 99% identical to SEQ ID NO:20, c) a nucleotide sequence selected from the group consisting of SEQ ID NO:1, SEQ ID NO: 3, SEQ ID NO:5, SEQ ID NO:7, SEQ ID NO:9, SEQ ID NO:11, SEQ ID NO: 13, SEQ ID NO: 15, SEQ ID NO:17 and SEQ ID NO:19, and d) an immunogenic fragment of a nucleotide sequence selected from the group consisting of a fragment of SEQ ID NO: 1 that encodes at least 60% of SEQ ID NO:2, a fragment or variant of SEQ ID NO:3 that encodes over at least 60% of the amino acid sequence at least 99% identical to SEQ ID NO:4, a fragment or variant of SEQ ID NO:5 that encodes over at least 60% of the amino acid sequence at least 99% identical to SEQ ID NO:6, a fragment or variant of SEQ ID NO: 7 that encodes over at least 60% of the amino acid sequence at least 99% identical to SEQ ID NO:8, a fragment or variant of SEQ ID NO:9 that encodes over at least 60% of the amino acid sequence at least 99% identical to SEQ ID NO: 10, a fragment or variant of SEQ ID NO: 11 that encodes over at least 60% of the amino acid sequence at least 99% identical to SEQ ID NO: 12, a fragment or variant of SEQ ID NO:13 that encodes over at least 60% of the amino acid sequence at least 99% identical to SEQ ID NO:14, a fragment or variant of SEQ ID NO:15 that encodes over at least 60% of the amino acid sequence at least 99% identical to SEQ ID NO: 16, a fragment or variant of SEQ ID NO:17 that encodes over at least 60% of the amino acid sequence at least 99% identical to SEQ ID NO:18 and a fragment or variant of SEQ ID NO:19 that encodes over at least 60% of the amino acid sequence at least 99% identical to SEQ ID NO: 20.

11. The nucleic acid molecule of claim 8, wherein the encoded peptide is operably linked to at least one regulatory sequence selected from the group consisting of a start codon, an IgE leader sequence and a stop codon.

12. The nucleic acid molecule of claim 8, wherein the nucleic acid molecule comprises an expression vector.

13. The nucleic acid molecule of claim 8, wherein the nucleic acid molecule comprises a viral particle.

14. An immunogenic composition comprising the peptide of claim 8.

15. A peptide comprising an amino acid sequence selected from the group consisting of a) an amino acid sequence having at least 99% identity over an entire length of the amino acid sequence selected from the group consisting of SEQ ID NO:2, SEQ ID NO:4, SEQ ID NO: 6, SEQ ID NO:8, SEQ ID NO: 10, SEQ ID NO: 12, SEQ ID NO: 14, SEQ ID NO: 16, SEQ ID NO: 18 and SEQ ID NO:20, and b) the amino acid sequence selected from the group consisting of SEQ ID NO:2, SEQ ID NO: 4, SEQ ID NO:6, SEQ ID NO:8, SEQ ID NO:10, SEQ ID NO: 12, SEQ ID NO: 14, SEQ ID NO: 16, SEQ ID NO: 18 and SEQ ID NO:20.

16. A method of inducing an immune response against a CDV antigen in a subject in need thereof, the method comprising administering an immunogenic composition of claim 1 to the subject.

17. The method of claim 16, wherein administering includes at least one of electroporation and injection.

18. A method of treating CDV infection or preventing disease associated with CDV infection in subject in need thereof, the method comprising administering an immunogenic composition of claim 1 to the subject.

19. The method of claim 18, wherein administering includes at least one of electroporation and injection.

20. The method of claim 18, wherein the subject is a member of a family selected from the group consisting of Canidae, Ailuridae, Mustelidae, Procyonidae, Hyaenidae, Ursidae, Viverridae, Felidae, and Tayassuidae.

* * * * *